United States Patent
Bettle, III et al.

(10) Patent No.: US 12,186,347 B2
(45) Date of Patent: *Jan. 7, 2025

(54) TOPICAL COMPOSITION COMPRISED OF COD LIVER OIL FOR TREATING WOUNDS AND SKIN DISORDERS

(71) Applicant: Omeza Holdings, Inc., Sarasota, FL (US)

(72) Inventors: Griscom Bettle, III, Sarasota, FL (US); John Harlin, Sarasota, FL (US); Thomas Gardner, Sarasota, FL (US)

(73) Assignee: Omeza Holdings, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/327,278

(22) Filed: Jun. 1, 2023

(65) Prior Publication Data

US 2024/0024374 A1 Jan. 25, 2024

Related U.S. Application Data

(63) Continuation of application No. 17/047,332, filed as application No. PCT/US2019/027396 on Apr. 12, 2019, now Pat. No. 11,903,977.

(Continued)

(51) Int. Cl.
*A61K 35/60* (2006.01)
*A61K 9/00* (2006.01)
(Continued)

(52) U.S. Cl.
CPC ............ *A61K 35/60* (2013.01); *A61K 9/0014* (2013.01); *A61K 31/14* (2013.01); *A61K 31/167* (2013.01); *A61K 36/185* (2013.01); *A61K 47/14* (2013.01); *A61K 47/22* (2013.01); *A61K 47/38* (2013.01); *A61K 47/44* (2013.01)

(58) Field of Classification Search
None
See application file for complete search history.

(56) References Cited

U.S. PATENT DOCUMENTS 7,297,668 B2  11/2007  Johansson et al.
8,628,796 B2  1/2014  Kottayil et al.
(Continued)

FOREIGN PATENT DOCUMENTS

WO  2009125117 A2  10/2009

OTHER PUBLICATIONS

Callaway, "Hempseed as a nutritional resource: An overview", Euphytica 140:65-72, 2004. (Year: 2004).*

(Continued)

*Primary Examiner* — Kyung S Chang
(74) *Attorney, Agent, or Firm* — Owen G. Behrens; Smith & Hopen, P.A.

(57) ABSTRACT

Disclosed is a topical anhydrous, homogenous pharmaceutical composition for treating skin disorder and wounds comprising cod liver oil, hempseed oil, monolaurin, medium chain triglycerides ("MCT"), free fatty acids, sea salt, and vegetable oil selected from the group consisting of red palm concentrate, coconut oil, and red palm oil and combination thereof and optionally fish collagen, ascorbyl palmitate, thickening agent, such as beeswax, red palm concentrate and cetyl ester.

14 Claims, 5 Drawing Sheets

Related U.S. Application Data

(60) Provisional application No. 62/776,258, filed on Dec. 6, 2018, provisional application No. 62/761,951, filed on Apr. 13, 2018.

(51) Int. Cl.
| | | |
|---|---|---|
| *A61K 31/14* | (2006.01) |
| *A61K 31/167* | (2006.01) |
| *A61K 36/185* | (2006.01) |
| *A61K 47/14* | (2017.01) |
| *A61K 47/22* | (2006.01) |
| *A61K 47/38* | (2006.01) |
| *A61K 47/44* | (2017.01) |

(56) References Cited

U.S. PATENT DOCUMENTS

| | | | |
|---|---|---|---|
| 9,415,082 B1 * | 8/2016 | Davis | ................... A61K 36/61 |
| 10,463,699 B2 | 11/2019 | Bettle, III | |
| 2010/0074963 A1 | 3/2010 | Bettle | |
| 2012/0016026 A1 | 1/2012 | Bromley et al. | |
| 2015/0374595 A1 | 12/2015 | Albrecht | |
| 2017/0189323 A1 | 7/2017 | Ballenas | |

OTHER PUBLICATIONS

Extended European Search Report dated Feb. 7, 2022 from related EP 19784767.6.

Anonymous, "Calming Face Cream", Jul. 3, 2017, pp. 1-7, Mintel, Database GNPD (online), www.gnpd.com.

Callaway, "Hempseed as a nutritional resource: An overview", Jan. 1, 2004, pp. 65-72, vol. 140, No. 102, Euphytica, Kluwer Academic Publishers, Netherlands.

Office Action dated Dec. 27, 2022 received in U.S. Appl. No. 17/047,332.

Decision of Rejection issued by Japanese Patent Office on Oct. 31, 2023 for corresponding Japanese Patent Application No. 2021-505627.

* cited by examiner

TOPICAL COMPOSITION COMPRISED OF COD LIVER OIL FOR TREATING WOUNDS AND SKIN DISORDERS

CROSS REFERENCE TO RELATED APPLICATIONS

The present application is a continuation of U.S. Ser. No. 17/047,332, filed in the USPTO on Oct. 13, 2020, which is a '371 of PCT/U2019/027396, filed on Apr. 12, 2019, which is claiming benefit of U.S. Ser. No. 62/761,951, filed on Apr. 13, 2018 and U.S. Ser. No. 62/776,258, filed on Dec. 6, 2018, the contents of all of which are incorporated by reference.

FIELD OF THE DISCLOSURE

The present disclosure relates to a topical composition comprised of fish oil containing omega-3 fatty acids, e.g., cod fish liver oil, hempseed oil, medium chain triglycerides ("MCT"), and vegetable oil selected from the group consisting of red palm concentrate, coconut oil, and red palm olein and combination thereof and optionally fish collagen, free fatty acids (FFA"), sea salt, ascorbyl palmitate, monolaurin, cetyl esters and thickening agents, such as beeswax, for treating wounds and skin disorders. Inherent in the composition are omega-6 fatty acids.

BACKGROUND OF THE DISCLOSURE

Fish oil, including cod liver oil, contains, among other components, omega 3-fatty acids. Omega-3 (n–3) fatty acids have a variety of anti-inflammatory and immune-modulating effects that may be of relevance to diseases and conditions where inflammation is an underlying cause. Inflammation is the body's attempt at self-protection where the aim is to remove harmful stimuli and start the healing process. Inflammation may be divided into acute and chronic inflammation where the acute inflammation starts rapidly and quickly becomes severe. Examples of acute inflammation may e.g. be acute bronchitis or acute appendicitis. Chronic inflammation may e.g. be failure to eliminate the causing agent, an autoimmune response to a self antigen or a chronic irritant of low intensity that persists. Chronic inflammation may however, mature into severe diseases such as chronic obstructive pulmonary disease (COPD), cancer, atherosclerosis, Alzheimer's disease (AD), amyotrophic lateral sclerosis (ALS) etc.

The omega-3 fatty acids are essential to life at any stage, even before birth. They are essential building blocks of the membrane of every cell in the body and their presence are a necessity for maintaining an adequate cell membrane. They do also contribute in the regulation of most biological functions.

The richest dietary source of very long-chain omega-3 polyunsaturated fatty acids (PUFA) comes from fish oil. Fatty acids are the building blocks of dietary fats, and are stored substantially in the form of triglycerides. The body cannot however, produce these fatty acids and must obtain them from food sources or from supplements. Four fatty acids compose the omega-3 family: alpha-linolenic acid (ALA: C18:2 (n3)), Stearidonic acid (SDA: C18:4 (n3), eicosapentaenoic acid (EPA: C20:5 (n3)) and docosahexaenoic acid (DHA: C22:6 (n3)). ALA and SDA are found in e.g. walnuts, some types of beans, hempseed oil, flax and olive oils. EPA and DHA are found in fish, including fish oil and supplements.

Resolvins and protectins are oxygenated metabolites derived from EPA and DHA, and a part of the molecular mechanisms contributing to removal of inflammatory cells and restoration of tissue once the need for inflammatory response is over. It has been shown that aspirin treatment enhances the conversion of EPA and DHA to resolvins which carry potent anti-inflammatory signals. The mechanisms by which their effects are exerted are still a matter of controversy, but it seems likely that said oxygenated metabolites play a significant role as they have potent anti-inflammatory and immunoregulatory actions even in concentrations in the nanomolar and picomolar range. As tissues return to normal, resolvins and protectins together with further oxygenated metabolites as lipoids and mare sins promote resolution of the inflammation through removal of leucocytes and cellular debris.

A recent study at Brigham and Women's Hospital in Boston revealed that omega-3s actually convert into compounds that are 10,000 times more potent than the original fatty acids themselves. These compounds include resolvins, which help bring an inflammatory response in the body to an end.

However, one of the problems associated with the use of fish oil is the strong fishy odor associated therewith that lingers and lingers. Because of the long-lasting fish odor, many topical compositions do not contain fish oil as an active ingredient. Moreover, even if fish oil is contained in topical compositions, consumers are reluctant to use those compositions because of the long-lasting odor. However, the present inventors have found a formulation that substantially eliminates the fishy smell.

The present invention also solves another problem, especially with compositions containing fish collagens and vegetable oils and seed oils. Mixtures of edible oils and powdered collagen have an inherent flaw. Powdered collagen is spray dried and extremely porous (sp. gr.=0.3). Molten oil/wax mixtures can penetrate the pores and form gels upon cooling. The problem with these mixtures is that when a cooled paste is pumped into, for example, a filling machine, the oil is expressed by external pump pressure on the pores. The paste separates into free oil and an immovable solid of collagen, wax and some oils. The net result is these thick pastes cannot be filled into useful packages.

The present invention solves these problems. More specifically, the topical compositions described herein are effective pharmaceutical and pharmaceutical devices for treating skin disorders and wounds, while simultaneously moisturizing the skin. In addition, the topical formulations described herein eliminate or substantially reduce the fishy smell of the fish oil. Further, the present formulations described herein do not separate into different phases; for example, with compositions containing collagen, the formulations described herein do not separate into free oil and an immovable solid of collagen, wax and some oils under conditions for filling these vials and other useful pharmaceutical packaging and are readily dispensed from the vials or other pharmaceutical packaging without any of the oils from seeping into the walls of the vial or packaging during storage.

SUMMARY OF THE DISCLOSURE

The present disclosure describes a pharmaceutical topical composition which comprises cod liver oil, hempseed oil, medium chain triglycerides ("MCT"), and vegetable oil selected from the group consisting of red palm concentrate, coconut oil, and palm oil, such as red palm oil, RBD palm oil, and the like and combinations thereof, and optionally monolaurin, C8/C10 free fatty acids ("free fatty acids" or "FFA"), fish collagen and thickening agents, such as beeswax, sea salt cetyl ester, hydrocalloid, such as carboxymethylcellulose, and analgesics, said composition being anhydrous and homogenous. In an embodiment, the cod liver oil is present in an amount ranging from about 5 wt % to about 30 wt %, hemp oil is present in an amount ranging from about 5 wt % to about 30 wt %, and the vegetable oil, as defined hereinabove, being present in an amount ranging from about 10 wt % to about 50 wt %, and MCT ranging from about 5 wt % to about 45 wt %, said weight ratio of MCT and FFA, when present, ranging from about 4:1 to about 140:1, sea salt, when present, ranging from about 0.2 wt % to about 1.0 wt %, said sea salt is typically ground to an average size of less than about 200 Tyler Mesh Screen, that is less than about 74 microns, wherein the weight ratio of monolaurin to cetyl esters, when present, ranging from about 0.3:1 to about 2.5:1 and the cetyl esters, when present, being present in an amount ranging from about 0.8 wt % to a maximum of 3 wt %, wherein the sum of the cod liver oil, hempseed oil, monolaurin, sea salt, MCT, free fatty acid, and vegetable oil ranging from about 40 wt % to about 100 wt % of the composition. In another embodiment, the cod liver oil is present in an amount ranging from about 5 wt % to about 30 wt %, hemp oil is present in an amount ranging from about 5 wt % to about 30 wt %, and the vegetable oil, as defined hereinabove, being present in an amount ranging from about 10 wt % to about 30 wt %, said weight ratio of MCT and FFA ranging from about 4:1 to about 140:1, sea salt, when present, ranging from about 0.2 wt % to about 1.0 wt %, said sea salt is typically ground to an average size of less than about 200 Tyler Mesh Screen, that is about 74 microns or less, wherein the weight ratio of monolaurin to cetyl esters, when present, ranging from about 0.3:1 to about 2.5:1 and the cetyl esters, when present, being present in an amount ranging from about 0.8 wt % to a maximum of 3 wt %, wherein the sum of the cod liver oil, hempseed oil, monolaurin, sea salt, MCT, free fatty acid, and vegetable oil ranging from about 40 wt % to about 100 wt % of the composition. In another embodiment, the weight ratio of MCT to oleic acid (primarily from palm oil), when present, is greater than 1. In a further embodiment, in compositions described herein, in the hydrocolloid composition and skin protectant compositions, described herein, e.g., skin protectant A and skin protectant B, the weight ratio of MCT to the sum of the weights of the total unsaturated triglycerides (from other vegetable oils and the cod liver oil) present in the composition of the present disclosure is greater than 0.8 and in another embodiment, greater than 1. In other compositions described herein especially in the collagen containing composition and compositions containing analgesics, the weight ratio of MCT to total unsaturated triglycerides present in the disclosure is less than 0.8. In a further embodiment, the weight ratio of MCT to oleic acid being greater than the weight ratio of the MCT relative to the sum of the weights of the total mono-unsaturated triglycerides 1, and the difference between the former and the latter being greater than 0.3. In an embodiment, the weight ratio of hempseed oil to cod liver oil ranges from about 2:1 to about 1:1 and in another embodiment, it is about 1:1. In another embodiment, the high-oleic red palm oil is replaced by coconut oil alone or coconut oil in combination with red palm concentrate, a carotenoid-rich, vitamin-rich fraction extracted from red palm oil. The red palm concentrate is present in a range of about 0.1 wt % to about 2 wt %. With respect to all of the formulations described herein, since hemp oil and cod liver oil contain omega-6 fatty acids, omega-6 fatty acid is present in all of the formulations described herein. Moreover, in an embodiment, the weight ratio of omega-6 fatty acids to omega 3 fatty acids is 1.0 to 3.0 and in another embodiment, ranges from about 1.2 to about 2.5 and in a further embodiment, from about 1.5 to about 2.0.

In an embodiment, the composition of the present disclosure does not contain any collagen, including any fish collagen, the composition being anhydrous and homogenous and a monophasic liquid. When the composition does not contain collagen, the composition comprises cod liver oil, hemp oil, MCT and vegetable oil, as defined hereinabove and optionally FFA, monolaurin, and cetyl ester. In an embodiment, the cod liver oil is present in an amount ranging from about 5 wt % to about 40 wt % and in another embodiment, from about 8 wt % to about 35 wt % and in another embodiment, from about 20% to about 30 wt %, and hemp oil is present in an amount ranging from about 8 wt % to about 35 wt % and in another embodiment, from about 20 wt % to about 30 wt %, the vegetable oil, as defined hereinabove, being present in an amount ranging from about 10 wt % to about 40 wt % and in another embodiment, from about 10 wt % to about 30 wt %, and wherein the sum of the weights of cod liver oil, hempseed oil, MCT, and vegetable oil ranging from about 80 wt % to about 100 wt % of the composition. In another embodiment, the weight ratio of MCT and FFA, when FFA is present, ranging from about 70:1 to about 140:1, and in another embodiment, the weight ratio of monolaurin to cetyl esters, when both are present, ranging from about 0.3 to about 1:1 and the cetyl esters, when present, are present in an amount ranging from about 0.8 wt % to a maximum of 3 wt %. In an embodiment, the weight ratio of MCT to oleic acid is greater than 1 and the weight ratio of MCT to the total monounsaturated triglycerides present in the composition of the present disclosure is greater than 1, with the weight ratio of the former being greater than the weight ratio of the latter, and the difference between the former and the latter being greater than 0.3. In another embodiment, when free fatty acids are present, the sum of the weights of cod liver oil, hempseed oil, monolaurin, MCT, free fatty acid, and vegetable oil ranges from about 80 wt % to about 100 wt % of the composition.

In another embodiment, fish collagen is present. In this embodiment, the pharmaceutical composition comprises an oily solution having a viscosity ranging from about 10 cP to about 100 cP and a surface tension ranging from about 20 mN/m to about 35 mN/m, the composition being comprised of cod liver oil, hempseed oil, monolaurin, medium chain triglycerides ("MCT"), free fatty acids, cetyl esters and vegetable oil selected from the group consisting of red palm concentrate, coconut oil, and palm oil, including red palm oil and RBD palm oil and combinations thereof and optionally sea salt and optionally thickener, e.g., beeswax said composition being anhydrous and homogenous. In an embodiment, the cod liver oil is present in an amount ranging from about 5 wt % to about 15 wt %, hemp oil is present in an amount ranging from about 15 wt % to about 10 wt %, MCT is present in an amount from about 6 wt % to about 12 wt %, free fatty acid being present in an amount ranging from about 0.5 wt % to about 1.5 wt %, the fish collagen is present in an amount ranging from about 35 wt % to about 50 wt % and the vegetable oil, as defined hereinabove, being present in an amount ranging from about 8 wt % to about 30 wt %, wherein the sum of the cod liver oil, hempseed oil, fish collagen, monolaurin, sea salt, MCT, free fatty acid, and vegetable oil ranging from about 80 wt % to about 100 wt % of the composition. In an embodiment, the weight ratio of MCT and FFA ranging from about 5:1 to about 15:1, sea salt ranging from about 0.2% to about 1.0 wt %, weight ratio of monolaurin to cetyl esters, when cetyl esters are present, ranging from about 0.8:1 to about 2.5:1 and the cetyl esters being present in an amount ranging from about 0.8 wt % to a maximum of 3 wt %. In another embodiment, the weight ratio of the weight of MCT to the weight of oleic acid is greater than 1 and the weight ratio of the weight of MCT to the weight of the total sum of unsaturated triglycerides present in the composition is less than 1, with the weight ratio of the former being greater than the weight ratio of the latter. Further, in an embodiment, the difference between the former and the latter is greater than 0.3. The composition comprised of collagen has a minimum of two melting points, a lower and a higher melting point, which is at least more than 5° C. apart. Further, in an embodiment, said weight ratio of all of the triglycerides (both saturated and unsaturated) to fish collagen ranges from about 0.9:1 to about 1.1:1, and in another embodiment, about 1:1. In an embodiment, the composition is an eutectic composition. In another embodiment, the weight ratio of hempseed oil to cod liver oil ranges from about 2:1 to about 1:1 and in another embodiment, it is about 1:1. Moreover, in an embodiment, the weight ratio of omega-6 fatty acids to omega 3 fatty acids ranges from about 1.0 to about 3.0 and in another embodiment, ranges from about 1.2 to about 2.5 and in a further embodiment, from about 1.5 to about 2.0.

Another aspect of the present disclosure is directed to substantially removing the rancid fish smell from a topical pharmaceutical composition comprising cod liver oil and fish collagen, said method comprising adding to said composition cetyl esters, monolaurin and hempseed oil so that the weight ratio of hempseed oil to cod liver oil in said composition ranges from about 1:1 to about 2:1 and the weight ratio of fish collagen to monolaurin ranges from about 9:1 to about 12:1, and the cetyl esters being present in an amount ranging from about 1% by weight to about 3% by weight, with the ratio of the sum of the weights of monolaurin and hempseed oil and cetyl ester to the weight of codfish liver oil ranges from about 1:2 to about 2:1. In another embodiment, the present disclosure is directed to a method for removing the rancid fish smell from a topical pharmaceutical composition comprising cod liver oil in the absence of fish collagen or other collagen, said method comprises adding hempseed oil and monolaurin and cetyl esters so that the weight ratio of hempseed oil to cod liver oil ranges from about 2:1 to about 1:1 and the weight ratio of cod liver oil to monolaurin ranges from about 2:1 to about 20:1, the amount of cetyl esters ranges from about 1% by weight to about 3% by weight and the weight ratio of the sum of the weights of the cetyl ester, red palm concentrate, monolaurin and hempseed oil to cod liver oil ranges from about 1:2 about 2:1.

In another aspect, the composition of the present disclosure is a drug carrier for oil soluble drugs including pain killers, such as lidocaine. In an embodiment, the amount of drug present in the composition of the present disclosure as a carrier ranges from about 0.5% to about 4% of the composition.

In addition, an aspect of the present disclosure is directed to treating a skin disorder or wound on a subject by topically applying an effective amount of any of the compositions described herein.

BRIEF DESCRIPTION OF THE DRAWINGS

The objects, features and advantages will become apparent to one ordinary skill in the art, in view of the following detailed description taken in combination with the attached drawings, in which

FIG. 3 depicts the stacking of collagen (1) in a formulation of the present disclosure. FIG. 4 depicts the effect of coarse cubic salt crystals (2) on the interstices of the collagen (1). FIG. 5 depicts the effect of ground salt (3) on the interstices of collagen (1). FIG. 6 depicts the effect of a low concentration of salt (2) on the interstices of collagen (1). FIG. 7 depicts the effect of a high concentration of salt (2) on the in interstices of the collagen (1).

Figure 1:
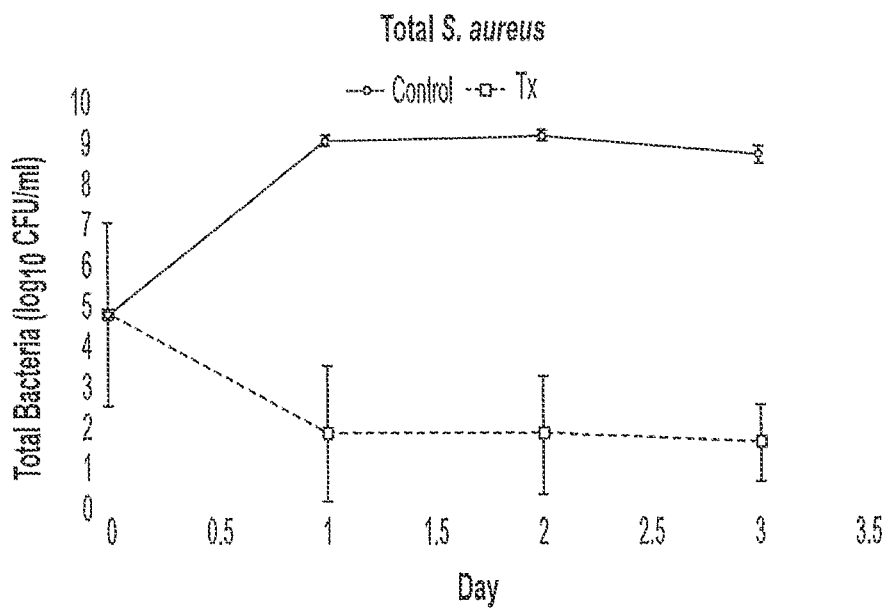
FIG. 1 is a graphical depiction of the effectiveness of a topical composition of Example 11, on killing bacteria on an ex vivo porcine skin wound biofilm model inoculated with S. aureus which was allowed to mature for four days. In this example, the vegetable oil is red palm concentrate and coconut oil in the absence of palm oil.

These figures help illustrate the subject matter of the disclosure of the present application, but the disclosure in the present application is not be construed as being so limited.

DETAILED DESCRIPTION OF THE DISCLOSURE

As described hereinabove, a useful component obtained from cod liver oil, is the very long (e.g. greater than C18) omega-3 fatty acids. The omega-3 fatty acids can be isolated from various marine life. For example, they are found in fish oil, algae and krill oil. As defined herein, "cod liver oil" refers to the oil extracted from the liver of codfish. Nutritionally important omega-3 fatty acids include α-linolenic acid (ALA) (18 carbon poly unsaturated fatty acid), Stearidonic acid (SDA) (18carbon poly unsaturated fatty acid) Eicosapentaenoic acid (EPA) (20 carbon in poly unsaturated fat) and docosahexaenoic acid (DHA) (22 carbon poly unsaturated fatty acid).

As defined herein, the terms "mixture of C8/C10 fatty acids", "C8/C10 fatty acid" and "C8/C10 fatty acids" or "free fatty acids" or "FFA", which are interchangeable, refer to a free C8 fatty acid or free C10 fatty acid or a mixture thereof. As used herein, the fatty acids are caprylic acid (C8 fatty acid), capric acid (C10 fatty acid) or a mixture thereof. In an embodiment, the free fatty acids are a mixture of caprylic and capric acid. In an embodiment, in a mixture of C8 fatty acid and C10 fatty acid, the amount of C8 fatty acid present by weight is greater than the amount of C10 fatty acid present by weight. For example, in an embodiment, the weight ratio of C8 fatty acid to C10 fatty acid ranges from about 1.8 to about 1.1, while in another embodiment it ranges from about 1.6 to about 1.3. Capric/caprylic fatty acid is typically a natural product derived from coconut oil. Commercial product ranges from about 53% to about 63% C8 and about 47% to about 37% by weight C10. Thus, in an embodiment, the weight ratio of C8 fatty acid to C10 fatty acid ranges from about 53:47 to about 63:37, which is a ratio ranging from about 1.13 to about 1.71.

The term "medium-chain triglyceride(s) of C8/C10 fatty acid", "medium-chain triglyceride(s) of C8/C10 fatty acids", "medium-chain triglycerides of a mixture of C8 and C10 fatty acids", "C8/C10 triglycerides", or "C8/C10 MCT" or "MCT" are interchangeable and refer to a triglyceride of C8 fatty acids, a triglyceride of C10 fatty acids or a triglyceride of a C12 fatty acid or a mixture thereof. In addition, the term C8 triglyceride refers to a triglyceride of a C8 fatty acid, and the term C10 triglyceride refers to a triglyceride of a C10 fatty acid. In an embodiment, it is a mixture of triglycerides of C8 and C10 fatty acids, wherein the amount by weight of triglycerides of C8 fatty acids present is greater than the amount by weight of triglycerides C10 present. It is to be understood that a MCT comprises additional triglycerides besides C8 and C10 triglycerides. An MCT comprises a triglyceride backbone having attached thereto three fatty acid chains that are generally from about C6 to C12 in length, although shorter or longer chains may be included within the term in differing contexts, as understood by those having skill in the art; but these longer and shorter chains are present in negligible amounts, for example, usually less than 3% by weight. The three medium chain fatty acids that are attached to the triglyceride backbone of the MCT may be, but need not be, identical. The medium chain fatty acids can be either saturated or unsaturated, but are preferably saturated. Examples of medium chain fatty acids that comprise the medium chain triglycerides of the invention include C6 (caproic fatty acid), C8 (caprylic fatty acid), C10 (capric fatty acid), and C12 (lauric fatty acid), as well as mixtures thereof. In an embodiment, the MCTs comprise a mixture of from about 60% C8 triglyceride and about 40% C10 triglyceride to a mixture of about 70% C8 triglyceride and about 30% triglyceride C10. In another embodiment, it comprises a mixture of about 51% C8 triglycerides and about 49% C10 triglycerides to about 70% C8 triglycerides to about 30% C10 triglycerides by weight; in another embodiment, it comprises about 55% C8 triglycerides and about 45% C10 triglycerides to about 65% C8 triglycerides to about 35% C10 triglycerides by weight. Further, as indicated hereinabove, the MCTs of the present disclosure may include minor amounts of triglycerides of short or long chain fatty acids, such as C6 or C4 fatty acids or C12 or C14 or C16 fatty acids, but the short or long fatty acids are present in minor amounts, e.g., less than about 3% by weight. In another embodiment, the MCT contains no triglyceride of a C12 fatty acid.

The medium-chain triglyceride(s) of C8/C10 fatty acids are prepared by chemical techniques known in the art by esterifying the fatty acid with glycerol.

As used herein, the terms "palm olein" is synonymous with the term "palm oil" and are used interchangeably. The term "palm oil" is the liquid portion which is separated from the semi-solid palm oil by fractionation. As used herein, the term includes red palm olein, and super red palm olein. The liquid portion is sold as cooking oils and the solid portion is known as "palm stearin." When palm olein is fractionated again to get a more liquid fraction, such as by chilling and removing the solid fraction of C18:0 (saturated C18 fatty acids) and some C16:0 (saturated C16 fatty acids), it is known as "super palm olein" or "CP6" (Cloud Point 6° C., meaning the separation took place at 6 C). Palm super olein is capable of withstanding colder temperature in comparison with palm olein after which they turn into solid. Palm olein is commonly used as cooking oil in the tropical countries. But the problem in temperate climate countries is that due to cold weather it tends to get cloudy and crystallize. To overcome this problem, palm olein is blended with more unsaturated vegetable oils. This blended form can be used in a wide range of climates and has a better cold stability. These blends are also cheaper than non-blended forms. The vegetable oils from rice bran, groundnuts and rapeseed are blended with palm olein to get a superior form in terms of quality and stability.

Red palm oil and palm oil are obtained from the endocarp of the palm fruit (the soft flesh); palm kernel oil is obtained from the seed (palm kernel oil). The oils are very much different. Red palm oil has the highest level of antioxidants of any seed crop. The carotenoids (the beta-carotene fraction is a Vitamin A precursors), tocopherols and tocotrienols (Vitamin E) present therein give red palm oil its distinctive color. The carotenoids are bright red; the tocopherols and tocotrienols are yellow; together they make red palm oil orange/red colored. These highly colored compounds are not readily absorbed by the skin and stain the skin surface and any clothing or bedding surface with which it comes in contact. When palm oil is refined, the carotenoids (primarily beta-carotene and lycopene) are removed and remaining palm oil which is RBD (refined, bleached, deodorized) palm oil is yellow colored because the Vitamin E remains and the carotenoids are removed. It is understood that the term palm oil includes RBD palm oil and red palm oil, but the terms "red palm oil" and "red palm olein" does not include RBD palm oil. Moreover, the term "RBD" palm oil does not include red palm oil.

In an embodiment, the palm oil, the red palm olein, and the super red palm olein and RBD palm oil contains a low amount of saturated C18 fatty acid. By low amount, it means less than 0.5% by weight.

Monolaurin, as used herein, is also known as glycerol monolaurate, glyceryl laurate or 1-Lauroyl-glycerol. It is a monoglyceride. It is the mono-ester formed from glycerol and lauric acid. Its chemical formula is $C_{15}H_{30}O_4$.

The term cetyl esters, as defined herein, is an unbranched ester formed from cetyl alcohol and a C14, C16 or C18 fatty acid. The fatty acids may be saturated or unsaturated. As used herein, cetyl ester refers to esters of C14, C16, or C18 fatty acid or mixtures thereof and cetyl alcohol. Cetyl Esters is a synthetic wax that has similar composition and chemical properties to a natural wax which is found in the blubber of whales. The esters that are found in Cetyl Esters include cetyl palmitate, cetyl stearate, myristyl myristate, myristyl stearate, cetyl myristate, and stearyl stearate. In an embodiment, cetyl ester is Cetyl Ester NF, CAS 540-10-3, 2598-99-4, EINECS 208-736, 220-000-6, typically sourced from Rita Corporation, Crystal Lake, IL Sea salt, as used herein, is the salt produced from the evaporation of seawater. The sea salt used herein may be refined or unrefined. The colors and variety of flavors in sea salt are due to local clays and algae found in the waters from which the salt is harvested. For example, some boutique salts from Korea and France are pinkish gray, some from India are black. The chemical composition of sea salt is typically the same as the ions dissolved in seawater. In an embodiment, the following ions are present by dry weight percent: Sodium, 30.8; Potassium, 1.1; Magnesium, 3.7; Calcium, 1.2; Chloride, 55.5; Sulfate, 7.7. Thus, the sea salt used herein contains, as a minimum, those aforesaid ions. However, a study found the amount of trace elements, such as titanium, silver, cobalt, and lead in synthetic sea salt are much higher than those in sea water. The magnitude of the difference can be as large as 104 times. Unrefined sea salt contains small amounts of magnesium and calcium halides and sulphates, traces of algal products, salt-resistant bacteria and sediment particles. The calcium and magnesium salts confer a faintly bitter overtone, and they make unrefined sea salt hygroscopic (i.e., it gradually absorbs moisture from air if stored uncovered). Algal products contribute a mild "sea-air" smell, the latter from organobromine compounds. Sediments, the proportion of which varies with the source, give the salt a dull grey appearance. However, in an embodiment it is ground sea salt, ground to pass through a 200 Tyler Mesh Screen.

Collagen is a main protein component constituting connective tissue in animals and is characterized by having a collagen triple helical structure. A total of not less than 30 types of collagens have been reported which are respectively termed Type I, Type II, and so on. Type I collagen is the primary component of the derma, ligaments, tendons, bones, and the like; and Type II collagen is the primary component of articular cartilage. Further, Type IV collagen is mainly contained in a basal membrane, which is the undercoat of all epithelial tissues. Type I collagen is the most abundant collagen in the body.

In the present disclosure, the fish collagen used is a collagen hydrolysate (hereinafter sometimes referred to as collagen peptide) and it refers to a low molecular weight collagen obtained by hydrolyzing collagen from fish skins with an acid, alkali or enzyme. For example, a fish collagen hydrolysate can be obtained by immersing skins of fish in an acid or alkali solution to extract gelatin and treating the extracted gelatin with an enzyme or acid. The gelatin refers to the collagen pre-treated with an acid or alkali and then solubilized by heat hydrolysis. In an embodiment, the collagen is derived from marine life, such as cold-water fish. Cold water fish come from unpolluted water and do not have the diseases associated with land animals.

The collagen used in the present disclosure has a $T_g$ (glass transition temperature)<37° C. (normal body temperature). Practically this means that any marine collagen from a cold-water source is acceptable. An example is fish collagen, such as collagen from cod fish. On the other hand, bovine, hog, horse collagen are not useful and are not included in the definition of collagen used herein.

The term "oils," when used alone, refers to the combination of fish oil, C8/C10 triglyceride, and/vegetable oil and mixtures thereof.

As used herein, the term "coconut oil" is a generic term that includes crude coconut oil and coconut oil that has been refined. Coconut oil is the raw minimally processed oil from coconuts, and as used herein, is "crude coconut oil." Refined coconut oil is coconut oil that has been refined, bleached and deodorized, and is referred to herein as refined or RBD coconut oil." Refined coconut oil has a higher melting point than crude coconut oil. Unless indicated to the contrary, the term "coconut oil" includes both crude coconut oil and refined coconut oil.

The terms "hempseed oil" and "hemp oil," as used herein, are synonymous. It is prepared by pressing hemp seeds, especially hemp seeds that are cold-pressed. Unrefined hemp oil is dark to clear light green in color with a nutty flavor. However, in an embodiment, the hemp oil used herein is refined so that it is substantially free of tetrahydrocannabinol. It is manufactured from varieties of *Cannabis sativa* that are substantially free of tetrahydrocannabinol (THC). In the manufacturing process, THC is removed prior to pressing of the seed oil. In an embodiment, the hemp oil contains at most 1% by weight of THC and in another embodiment, less than or equal to 0.1% by weight THC, and in still further embodiment less than 0.01% by weight, if any, of THC. In another embodiment, the THC is not detectable, for example, less than 10 ppm. It contains gamma-linolenic acid, which is an omega-6 fatty acid, as well as alpha-linolenic acid, which is an omega-3 fatty acid.

The term "anhydrous," as used herein refers to the water content of the composition of the present disclosure. As defined herein, the water content of the present composition refers to free water, that is, water not chemically bound to a substrate. As defined, the composition contains less than about 0.5 wt % free water. For example, fish collagen may have bound water up to 8 wt % as a byproduct of spray drying. In an embodiment, if there were 40% fish collagen @ 8% bound moisture, the total moisture of the composition would be 3.2% bound water, but the free water content is negligible, e.g., below 0.5 wt %.

As defined herein the term "homogenous," as it relates to a composition described herein means that the components in the composition are substantially uniformly distributed throughout the composition at room temperature and following freeze/thaw abuse.

The term "eutectic composition" is a mixture of chemical compounds or elements that has a single chemical composition that melts at a lower temperature than any other composition made up of the same ingredients. A composition comprising a eutectic is known as the eutectic composition and its melting temperature is known as the eutectic temperature.

Cod liver oil comes from cod fish, e.g., Atlantic cod (*Gadus morhua*) or from Pacific cod (*Gadus microcephalus*). Both cod liver oils are acceptable, but Pacific cod oil is preferred because the Bering Sea water is pristine with very little heavy metals. Pacific cod liver oil is obtained from line-caught cod. The immediately eviscerated liver is frozen on board to retain its nutrients. Frozen livers are transferred to a shore-side processing plant, rendered and pressed into commercial cod liver oil with almost no odor. As used herein, the term "cod liver oil": refers to the oil that comes from codfish.

The term "melting" point, as used herein, is used in three senses. It has the usual meaning, in one sense, i.e. the temperature at which when a solid melts and form a liquid. However, with many of the oily compositions described herein, it is difficult to determine or measure the specific melting point. In those cases, one of the following definitions is applicable, dependent upon the specific compositions. In some cases, such as, for example, for oily compositions comprised of hemp oil in the absence of fish collagen, the melting point is defined when the oily composition turns cloudy as the temperature is lowered. In other instances such as compositions wherein the oily composition comprises hemp oil and collagen, it is defined when there is a visible change in viscosity when the temperature is raised. All three definitions are potentially applicable, but the term melting point with respect to the compositions discussed herein, for purposes of this application, is the lowest temperature in which the composition either melts, as in the traditional definition, or turns cloudy or where there is a visible change in viscosity.

As defined herein, there are various ranges of numbers or ratios provided herein. It is to be understood that the ranges include not only the endpoints (plus or minus 5% when modified by the term about), but also all of the integral numbers and fractions therebetween. Thus, for example, if the range is defined as ranging from 5 wt % to 10 wt %, it is understood that the values include the endpoints 5 wt % and 10 wt %, but also all the integers and fractional numbers and real numbers therebetween and each one of those values are described herein, for purposes of the teaching of the disclosure described herein.

Unless indicated to the contrary, the terms "compositions" and "formulations" alone or in combination with other terms, such as for example, topical, are synonymous and can be used interchangeably.

Unless indicated to the contrary, the terms "drugs" and "medicament" are synonymous.

The term "burn" refers to an injury to tissues caused by contact with heat, flame, chemicals, electricity or radiation. First degree burns show redness, second degree burns show vesication (a blistered spot); third degree burns show necrosis (cell death through the entire skin).

Treatment" or "treating," as used herein refers to complete elimination as well as to any clinically or quantitatively measurable healing or alleviation of the symptoms of the wound or skin condition.

A "therapeutically effective amount" means the amount of a composition that, when administered to a subject for treating a wound, is sufficient to effect a desirable treatment for the wound, burn or skin condition. The "therapeutically effective amount" will vary depending on the particular composition, the condition and its type and severity, and the age, weight, etc., of the subject to be treated. The actual amount which comprises the "effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts. The skilled medical practitioner can readily determine the treatment regimen and the number of applications of each of the compositions described herein.

The term "topical" refers to administration or delivery of the composition described herein by application of the composition to a surface of a body part. For example, a composition can be topically administered by applying it to the skin, to the surface of a wound, burn, or skin condition, within the skin or within the mucous membrane.

"Patient" or "subject" refers to animals, and can include any mammal, such as humans, rats, mice, cats, dogs, goats, sheep, horses, monkeys, apes, rabbits, cattle, sea lions etc. The mammalian subject can be in any stage of development including adults, children, infants, and neonates.

The term "pharmaceutically acceptable carrier" as used herein describes a material that does not cause significant irritation to an organism and does not abrogate the biological activity and properties of the peptide of the composition of the described invention. Carriers must be of sufficiently high purity and of sufficiently low toxicity to render them suitable for administration to the mammal being treated. The carrier can be inert, or it can possess pharmaceutical benefits. The terms "excipient," "carrier," or "vehicle" are used interchangeably to refer to carrier materials suitable for formulation and administration of pharmaceutically acceptable compositions described herein. Carriers and vehicles useful herein include any such materials known in the art which are nontoxic and do not interact with other components. All of the compositions described hereinbelow may optionally contain a pharmaceutically acceptable carrier.

Unless indicated to the contrary, percentages are by weight and ratios are weight ratios.

The term "about," as used herein, when used before a number or numerical ranges, in an embodiment herein refers to an amount ±5% of that value of the number or range. For example, when referring to a range of about 9 to about 11, it is understood to range from 8.65-11.55.

As used herein, the singular forms "a," "an" and "the" include plural referents unless the context clearly dictates otherwise.

The term "granulation" refers to a process whereby small red, grain-like prominences form on a raw surface in the process of healing.

Furthermore, as used herein, the terms "components" and "ingredients" are synonymous, and are used interchangeably. In addition, the terms "thickener" and "thickening agent" are synonymous, and are used interchangeably.

The term, "collagen composition," as used herein, refers to any composition described hereinbelow, which contains collagen as described herein and optionally with a pharmaceutically acceptable carrier thereof. The term "hydrocolloid composition," refers to a composition that comprises a hydrocolloid as described herein and optionally with a pharmaceutically acceptable carrier. As used herein, the term "hydrocolloid" refers to either suitably naturally occurring hydrocolloids, or semi synthetic hydrocolloids, or combination of one or more hydrocolloids. Examples of hydrophobic water insoluble hydrocolloids include but not limited to as gum tragacanth, ethyl cellulose (e.g., ethyl cellulose 100), ethylhydroxyethyl cellulose, ethylmethyl cellulose, methyl cellulose, hydroxyethyl cellulose, hydroxyethylmethyl cellulose (e.g., K100LV, K4M, K15M), hydroxypropyl cellulose, poly(hydroxyethyl methacrylate), cellulose acetate (e.g. cellulose acetate CA-398-10 NF), cellulose acetate phthalate, cellulose acetate propionate, cellulose acetate butyrate, hydroxypropyl methyl cellulose acetate succinate, hydroxypropyl methyl cellulose phthalate, cellulose butyrate, cellulose nitrate, oxypolygelatin, pectin and the like. Suitably the hydrocolloids are in the form of particles, but can be rolled into a flat sheet for application to cover a wound surface.

An embodiment of the present disclosure is directed to a topical composition and optionally a pharmaceutically acceptable carrier therefore that does not contain collagen, including fish collagen. The topical pharmaceutical composition in this embodiment comprises cod liver oil, MCT, hemp oil and vegetable oil, and optionally C8/C10 free fatty acids, monolaurin, and cetyl esters and optionally, a pharmaceutically acceptable carrier may be present. In an embodiment, the cod liver oil is present in an amount ranging from about 5 wt % to about 35 wt % (for example from about 10 wt % to about 35 wt %), MCT is present in an amount ranging from about 20 to about 50 wt %, e.g., from about 20 wt % to about 40 wt %), C8/C10 fatty acid, when present, is present in an amount ranging from about 0.1 to about 2.0 wt %, hemp oil is present in an amount ranging from about 5 wt % to about 45 wt %, (for example, from about 10 wt % to about 35 wt %) monolaurin when present, is present in an amount ranging from about 0.3 to about 2.0 wt %, vegetable oil being present in an amount ranging from about 10 wt % to about 45 wt %, such as, for example, from about 10 wt % to about 30 wt %, and cetyl esters, when present, are present in an amount ranging from about 0.5 to about 2.5 wt %. In another embodiment, the cod liver oil is present in an amount ranging from about 20 to about 30 wt %, MCT is present in an amount ranging from about 25 to about 35 wt %, C8/C10 fatty acid, when present, is present in an amount ranging from about 0.3 to about 1.2 wt %, hemp oil is present in an amount ranging from about 20 to about 30 wt %, monolaurin, when present, is present in an amount ranging from about 0.5 to about 1.0 wt %, vegetable oil is present in an amount ranging from about 10 wt % to about 40 wt %, and cetyl ester, when present, is present in an amount ranging from about 0.75 to about 1.5 wt.

In an embodiment when fish collagen is not present, the cod liver oil is present in an amount ranging from about 5 to about 35 wt % of the composition, in another embodiment, from about 7 to about 30 wt % of the composition and in another embodiment, from about 8 wt % to about 28% of the composition.

Further, in an embodiment where fish collagen is not present, the C8/C10 free fatty acids, when present are present in an amount ranging from about 0.15 wt % to about 1.00 wt % and in another embodiment from about 0.20 wt % to about 0.50 wt % and in another embodiment from about 0.25 wt % to about 0.35 wt %.

In another embodiment, where fish collagen is not present, the MCT is present in an amount ranging from about 20 wt % to about 45 wt %.

Further, in an embodiment, where fish collagen is not present, the weight ratio of MCT to C8/C10 free fatty acid, when present, ranges from about 8:1 to about 140:1.

The hemp oil, in an embodiment in the absence of collagen, including fish collagen, is present in an amount ranging from about 5 wt % to about 35 wt % of the composition, in another embodiment, about 8 wt % to about 30 wt % of the composition and in another embodiment, from about 8.5 wt % to about 28% of the composition.

In an embodiment, when fish collagen is not present, the hemp oil and the cod liver oil is present in a weight ratio of about 1:1 to about 2:1, respectively; and in another embodiment, in a weight ratio of about 1:1 to about 1.5:1 and, in still another embodiment, they are both present in about equal weight amounts, i.e., about 1:1 by weight.

The function of the monolaurin, when present, in the formulations described herein with and without fish collagen, is to help reduce the undesirable rancid smell of the cod liver oil. However, without wishing to be bound, it performs this function with the presence of hemp oil and cetyl ester. In an embodiment, in the absence of fish collagen, monolaurin, when present, is present in amounts of less than 1% by weight of the composition. In another embodiment, in the absence of fish collagen, monolaurin when present, is present in an amount ranging from about 0.3 wt % to about 0.99% by weight, and in another embodiment, in the absence of fish collagen, from about 0.5 wt % to about 0.75 wt % of the composition and a still further embodiment from about 0.55 wt % to about 0.65 wt % of the composition.

In addition, the present inventors have also found that another ingredient that helps remove the fishy odor in compositions described herein in the presence and absence of fish collagen is cetyl esters. In an embodiment, in the absence of fish collagen, the cetyl esters, when present, are present in an amount ranging from about 0.5% to 3% by weight. In another embodiment, in the absence of fish collagen, the cetyl esters are present in an amount ranging from about 1% to 3% by weight of the composition.

In an embodiment which does not contain fish collagen, when both components are present, the weight ratio of cetyl esters to monolaurin is greater than 1:1. In an embodiment where fish collagen is not present, when both components are present, the weight ratio of cetyl ester to monolaurin ranges from about 1:0.5 to about 1:0.7, and in a further embodiment where fish collagen is not present, in about a weight ratio of about 5:3.

The present inventors have found that another means of reducing the rancid fish oil in compositions described herein containing fish collagen or in the absence of fish collagen is to use less of the cod liver oil. This is effected by utilizing hemp oil. Hemp oil is a source of omega-3 fatty acids. Fish oil provides very long chain omega-3 fatty acids (C>18); hemp oil provides long chain omega-3 fatty acids (C=18). The body enzymatically takes omega-3 fatty acids and either shortens or lengthens the chain length to make, for example prostaglandins. If the omega-3 fatty acid is C18, the elongation process produces inflammatory and anti-inflammatory compounds. If the omega-3 fatty acid is already C>20, then the produced products are all anti-inflammatory. Wounds need some inflammatory compounds for example to control bleeding, as well as anti-inflammatory compounds, for example, to increase blood flow by reducing resistance to blood drainage.

In compositions of the present disclosure containing fish collagen and in the absence of fish collagen, the present inventors have found that it is advantageous to use hemp seed oil in addition to cod liver oil. This combination provides the most effective ratios of C18+C20 omega 3-fatty acids. However, there is also the trade-off between inflammatory byproducts and anti-inflammatory products with odor control. Nevertheless, in compositions comprised of fish collagen and in the absence of fish collagen described herein, the combination of C18+C20 omega 3-fatty acids lowers the foul fish odor smell. Thus, by using a greater amount of hemp oil, less cod fish liver oil is necessary. Accordingly, as described hereinabove, by utilizing more hemp oil relative to cod liver oil, the present formulations containing fish collagen and in the absence of fish collagen reduce the rancid smell of cod liver oil. With respect to the remaining cod liver oil in the compositions of the present disclosure containing fish collagen and/or in the absence of fish collagen, as long as the ratio of monolaurin and cetyl ester is in the weight ratio described above, the remaining rancid fish smell of the cod liver oil is considerably reduced or eliminated. Thus, for example, for formulations which do not contain fish collagen, the weight ratio of the cod liver oil to the sum of the weights of the monolaurin and the cetyl ester ranges from about 20:1 to about 10:1, and in another embodiment, from about 18:1 to about 14:1, and in another embodiment, at about 16:1. The amount of these components present depends upon whether collagen is present or not. In the absence of collagen, monolaurin is mixed in a weight ratio of cod liver oil to monolaurin ranging from about 50:1 to about 40:1, and in another embodiment, from about 46:1 to about 42:1. If the level of monolaurin in compositions containing fish collagen or in the absence of fish collagen is low, the desired odor effect is not realized. If the level of monolaurin in compositions containing fish collagen or in the absence of fish collagen is high, a syrupy gel forms that makes a two-phase sticky fluid. However, there is a maximum amount of monolaurin that can be present in the pharmaceutical composition containing fish collagen or in the absence of fish collagen; the monolaurin may not exceed 2% by weight of the oil composition comprised of cod liver oil. Above this amount, the monolaurin forms an unstable gel. In an embodiment in compositions containing fish collagen or in the absence of fish collagen, the monolaurin does not exceed 2% by weight, and in another embodiment, it does not exceed 1% by weight of the composition. However, when present, the monolaurin should be present in the composition contain fish collagen or in the absence of fish collagen in an amount greater than 0.5 wt %.

An embodiment of the present disclosure, both in the presence and absence of fish collagen is the reduction or elimination of the rancid fish smell associated with cod liver oil when used in a topical composition, while moisturizing the skin. It has been found that the addition of hemp oil, cetyl esters and MCT and monolaurin to the fish oil composition reduces or eliminates completely the rancid fish odor, and when the composition is applied to the skin of a patient, the wound or skin disorder is reduced in size and the skin of the patient is moisturized. The amount of these components added depends upon whether collagen is present or not.

In addition, the present inventors have also found that another ingredient that helps remove the fishy odor, whether fish collagen is present or not, is cetyl esters. In an embodiment, in the presence or absence of fish collagen, the cetyl ester, when present, are present in an amount ranging from about 0.5% to 3% by weight. In another embodiment, the cetyl esters, whether fish collagen is present or not, if present, cetyl esters are present in an amount ranging from about 1% to about 2.5% by weight of the composition. In an embodiment, which includes formulations where collagen is not present, the topical composition comprises cod liver oil in an amount ranging from about 20% by weight to about 35% by weight, monolaurin is present in an amount ranging from about 0.5% to about 2% by weight, and cetyl esters present in an amount ranging from about 1% to about 2.5% by weight. In the formulation without collagen, the amount of cetyl esters present by weight is greater than the amount present of monolaurin by weight.

Although cetyl esters also reduces the fishy smell, when used in combination with monolaurin in a topical cod liver oil composition that does not contain collagen there is a synergistic effect in reducing rancid fish smell. In an embodiment not containing collagen, per gram of fish oil, the weight ratio of cetyl esters to monolaurin ranges from about 1:1 to about 2:1; in another embodiment, from about 1.3:1 to about 1.8:1; and in a further embodiment, from about 1.6:1 to about 1.7:1 Nevertheless, the combination is more effective in removing the fishy smell than monolaurin or cetyl esters alone. Further, adding cetyl esters to the formulation created a silky smooth skin surface (finish) that is very pleasant to the touch.

Without wishing to be bound, it is believed for compositions comprised of cod liver oil described herein which contain collagen and do not contain collagen that monolaurin acts as a process aid as it affects gelation. The monolaurin helps the cod liver oil be absorbed by unbroken skin. It is believed that the faster the cod liver oil is absorbed, the less oxidation odor is generated.

With respect to the formulations described hereinbelow, wherein collagen is not present or is present, without wishing to be bound, it is believed that the monolaurin helps drive the Omega-3 fats into the stratum corneum, leaving only a small residual of potentially oxidizable fat on the skin surface. The Cetyl Ester wax provides a late-drying odor-occlusive layer over any potentially oxidizable fat and over the free fatty acid (FFA). The net result is no odor after about 30 seconds.

The pharmaceutical composition not containing collagen described herein comprises a vegetable oil selected from the group consisting of palm oil, including red palm oil and RBD palm oil, coconut oil, including refined coconut oil and red palm concentrate and a combination thereof. The amount of this vegetable oil present in these compositions ranges from about 10 wt % to about 45 wt %, and in another embodiment, from about 12 wt % to about 40 wt %.

In an embodiment in the composition that does not contain collagen, coconut oil may be the only vegetable oil present or it may be present in combination with the red palm concentrate but in the absence of palm oil. This combination reduces the amount of oleic fatty acid (from the palm oil) and replaces it with lauric acid (C12:0 from the crude coconut oil). Lauric triglyceride is a better skin moisturizer than oleic triglyceride. Replacing palm oil with its inherent high concentration of Vitamin E with coconut oil which has no Vitamin E is counter intuitive because Vitamin E is widely regarded as an essential vitamin for robust skin health. What has been found is that replacing palm oil with coconut oil and red palm concentrate changes the homogenous oil from a skin moisturizer into an oil that disrupts pathogen growth, best executed in wound healing products.

In another embodiment, in the compositions where collagen is not present, the vegetable oil comprises RBD palm oil, which is present in the amounts indicated hereinabove. In some embodiments, vegetable oil may only comprise RBD palm oil. As described herein, or red palm concentrate contains carotenoids. Without wishing to be bound, it is believed that carotenoids can act as both antioxidants and pro-oxidants under different conditions. The antioxidant property of carotenoids is well-known. It is further believed that carotenoids can switch from anti-oxidant to pro-oxidant behavior as a function of oxygen concentration. Thus, carotenoids in a composition in an oxygen-barrier package will behave as antioxidants and protect the fish oil. Then when the composition is spread over a wound exposed to air, the carotenoids can become pro-oxidants. Some of the oxidized carotenoids become Reactive Oxygen Species (ROS). The ROS, a free radical antimicrobial compound, in turn help reduce the pathogen concentration in infected wounds as shown in FIG. 1. The carotenoids act as both an anti-oxidant and pro-oxidant when the composition is a mixture of fast absorbing compounds, like MCT, and slow absorbing compounds like cod liver oil. As the MCT is absorbed, the carotenoid and cod liver oil concentrate on the skin surface, increasing the micro concentration of the carotenoids at the site of infection. What is observed is faster wound bed granulation and faster wound closure.

It is thought that the addition of different antioxidants, for example, Vitamin E and Ascorbyl Palmitate, increase the antioxidant capacity of the composition because each has its own mechanism of action. Thus, replacing Vitamin E-rich palm oil with nil Vitamin E coconut oil which does not contain significant concentration of Vitamin E and adding red palm concentrate increases the in vitro antioxidant capacity (in combination with oxygen barrier packaging) but decreases the in vivo antioxidant capacity and increases the pro-oxidation ROS sufficiently that infection is controlled without a negative effect on the healing rate. Adding MCT to the crude coconut oil and carotenoids accelerates the healing process by concentrating the ROS on the surface where there can be infection. It is counterintuitive to use the same composition to be an antioxidant during storage and distribution and a source of pro-oxidant, antimicrobial ROS when the composition is applied to the wound, as in the present formulation.

When palm oil is used with red palm concentrate, the palm oil Vitamin E and the carotenoids work together to keep the carotenoids in the anti-oxidant mode. The Vitamin E absorbs the ROS before any killing takes place and terminates free radical propagation. Thus, bacterial kill is not observed. But, when coconut oil replaces palm oil, there is no vitamin E in the mixture. The carotenoids are antioxidants in an oxygen barrier package and then are pro-oxidants when applied to skin and exposed to air. There is little vitamin E, so the carotenoid-produced ROS is not quenched and goes on to kill bacteria. Multi-log bacterial kill is observed.

In an embodiment, where coconut oil is present, the red palm concentrate is present in less than 1% by weight. In an embodiment, it is present in an amount ranging from about 0.5 wt % to about 0.1 wt %, and in another embodiment, about 0.26 wt %.

In another embodiment, in a composition without collagen, the vegetable oil is RBD palm oil, without red palm oil or red palm concentrate. In this embodiment, the RBD palm oil is present in about ranging from about 18 wt % to about 10 wt %, and in another embodiment, from about 16 wt % to about 12 wt %, and in another embodiment, from about 15 wt % to about 13 wt %. This embodiment is indicated for use on intact skin. The Vitamin E in the palm oil is advantageously used on intact skin; any red/orange residual color on the skin from the application of red palm concentrate on the skin is perceived by consumers as a defect. The previously described rapid absorption with an odor-occlusive silky-smooth film makes this a consumer-acceptable composition to bring topical omega-3 fatty acids from the cod liver oil and hemp seed oil to intact skin.

Compositions of the present invention not containing collagen, including fish collagen, are comprised of MCT, Crude Coconut Oil, cod liver oil, hemp oil and a hydrocolloid, as defined herein and optionally a pharmaceutically acceptable carrier. In an embodiment, the hydrocolloid that can be used is carboxymethylcellulose or any of the hydrocolloids listed herein. The weight % numbers are based only on the 100% oil fraction (which is added at about 12% of the finished bandage weight) of the finished hydrocolloid bandage. In an embodiment, this composition comprises cod liver oil in an amount ranging from about 7 to 15 wt %, hemp oil in an amount ranging from about 7 to 15 wt %, wherein the ratio of hemp oil to cod liver oil is as defined herein, MCT in an amount of about 30 wt % to about 45 wt %, crude coconut oil in an amount of about 30 wt % to about 45 wt %; wherein the weight ratio of MCT to crude coconut oil ranges from about 0.8:1 to 1.2:1 and in another embodiment, at about 1:1. The blended oil mixture is then added at about 12 wt % to the hydrocolloid mixture to make 100% of the hydrocolloid bandage. After processing the finished, extruded, rolled and chilled hydrocolloid is a flexible sheet laminated with a plastic film over the sticky side and then inserted into a sealed pouch. The user opens the pouch and retrieves the bandage, then peels off the film and sticks the hydrocolloid composition over the wound and surrounding periwound or the situs of the burn or skin condition and the intact skin area adjacent thereto. The hydrocolloid is now a protective cover over the wound, burn or skin condition, and the surrounding periwound. Since the hydrocolloid is a protective cover, no further dressing is required. The patient continues normal activities. Periodically, as determined by the physician, such as, for example, after 7 days, the hydrocolloid is peeled off the side of the wound, burn or skin condition and discarded. If additional treatment is required, as determined by the physician, another hydrocolloid composition, in accordance with the present invention, is used. The finished bandage is a mixture of oil, the hydrocolloid, tackifiers, process aids, water and other ingredients typically used to make the hydrocolloid adhere to the skin, such as the periwound and various process aids. The hydrocolloid is present in an amount ranging from about 10 wt % to about 50 wt %. wherein the sum of the coconut oil, MCT, hydrocolloid, hemp oil and cod liver oil ranges from about 5 wt % to about 15 wt % of the finished hydrocolloid dressing. In another embodiment, the MCT oil is present in an amount ranging from about 35 wt % to about 42 wt %, crude coconut oil is present in an amount ranging from 35 wt % to about 42 wt %, hemp oil is present in an amount from about 8 wt % to about 12 wt %, cod liver oil is present in an amount ranging from about 8 wt % to about 12 wt % of the oil fraction and the hydrocolloid, such as carboxymethylcellulose is present in an amount of about 15 wt % to about 40 wt % of the finished hydrocolloid dressing. It is to be understood that the composition comprised of hydrocolloid is also known as the hydrocolloid composition.

In an embodiment, the hemp oil and the cod liver oil are present in a weight ratio of about 1:1 to about 2:1, respectively, and in another embodiment, in a weight ratio of about 1:1 to about 1.5:1, and in still another embodiment, they are both present in about equal amounts, i.e., about 1:1 by weight.

Other compositions of the present invention which does not contain collagen, such as fish collagen, are comprised of an oil soluble analgesic, such as lidocaine. By oil soluble analgesic, it is meant to be a drug which is a pain-reliever that is completely soluble or substantially completely soluble in the pharmaceutical composition described herein. Examples of oil soluble drugs include lidocaine, benzocaine and narcotic opioids, In an embodiment, the analgesic composition comprises MCT oil, FFA, monolaurin, cetyl esters, hydrophobic analgesic, such as lidocaine, vegetable oils, such as RBD palm oil, red palm concentrate and the like, hemp oil and cod liver oil and optionally a pharmaceutically acceptable carrier. In an embodiment, hemp oil is present in an amount ranging from about 8 wt % to about 35 wt %, cod liver oil is present in an amount ranging from about 8 wt % to about 35 wt %, hydrophobic analgesic is present in an amount ranging from 0.6 wt % to about 1.2 wt %, MCT oil is present in an amount ranging from about 20 to about 40 wt %, C8/C10 fatty acid is present in an amount ranging from about 0.1 to about 1.0 wt %, monolaurin, when present, is present in an amount ranging from about 0.3 to about 2.0 wt %, vegetable oil is present in an amount ranging from about 10 wt % to about 30 wt %, such as, for example, from about 10 wt % to about 30 wt %, and cetyl esters, when present, are present in an amount ranging from about 0.5 to about 2.5 wt %, wherein the sum of the MCT oil, FFA, monolaurin, cetyl esters, hydrophobic analgesic, vegetable oil such as RBD palm oil, red palm concentrate, hemp oil and cod liver oil ranges from about 80 wt % to about 100 wt % of the composition.

The hemp oil, in an embodiment, is present in an amount ranging from about 20 wt % to about 35 wt % of the composition, in another embodiment, from about 22 wt % to about 30 wt % of the composition and in another embodiment, from about 24 wt % to about 28% of the composition.

The cod liver oil, in an embodiment, is present in an amount ranging from about 20 wt % to about 35 wt % of the composition, in another embodiment, about 22 wt % to about 30 wt % of the composition and in another embodiment, from about 24 wt % to about 28% of the composition.

In an embodiment, the hemp oil and the cod liver oil is present in a weight ratio of about 1:1 to about 2:1, respectively; and in another embodiment, in a weight ratio of about 1:1 to about 1.5:1 and, in still another embodiment, they are both present in about equal weight amounts, i.e., about 1:1 by weight.

Further, in an embodiment, the C8/C10 free fatty acids, when present are present in an amount ranging from about 0.15 wt % to about 1.00 wt % and in another embodiment from about 0.20 wt % to about 0.50 wt % and in another embodiment from about 0.25 wt % to about 0.35 wt %.

In another embodiment, the MCT is present in an amount ranging from about 20 wt % to about 40 wt %.

Further, in an embodiment, the weight ratio of MCT to C8/C10 free fatty acid, ranges from about 90:1 to about 140:1, and in another embodiment, from about 100:1 to about 120:1.

In an embodiment, monolaurin is present in amounts of less than 1% by weight of the composition. In another embodiment it is present in an amount ranging from about 0.3 wt % to about 0.99% by weight, and in another embodiment, from about 0.5 wt % to about 0.75 wt % of the composition and a still further embodiment from about 0.55 wt % to about 0.65 wt % of the composition.

In an embodiment, cetyl esters are present in an amount ranging from about 0.5% to 3% by weight. In another embodiment, the cetyl esters are present in an amount ranging from about 1% to 3% by weight of the composition.

In an embodiment, the weight ratio of cetyl esters to monolaurin is greater than 1:1. In an embodiment, the weight ratio of cetyl ester to monolaurin ranges from about 1:0.5 to about 1:0.7, and in a further embodiment, in about a weight ratio of about 5:3.

The amount of vegetable oil present ranges from about 10 wt % to about 20 wt %, and in another embodiment, from about 12 wt % to about 17 wt % and in another embodiment, from about 14 wt % to about 16 wt %.

As defined herein, the analgesic composition does not contain any collagen or hydrocolloid, and the hydrocolloid composition does not contain any analgesic or collagen.

Another composition of the present disclosure which does not contain collagen is a skin protectant, and will be referred to herein as skin protectant composition. The skin protectant composition does not contain any hydrocolloid, analgesic or collagen. However, it may optionally additionally comprise a pharmaceutically acceptable carrier.

There are two skin protectant compositions. One skin protectant composition is identified as skin protectant B. In an embodiment, the hemp oil is present in an amount ranging from about 5 wt % to about 15 wt %, cod liver oil is present in an amount ranging from about 5 wt % to about 15 wt % hemp oil, MCT oil is present in an amount ranging from about 30 to about 50 wt %, C8/C10 fatty acid is present in an amount ranging from about 0.1 to about 1.0 wt %, monolaurin is present in an amount ranging from about 0.3 to about 2.0 wt %, vegetable oil is present in an amount ranging from about 30 wt % to about 50 wt %, and cetyl esters, are present in an amount ranging from about 0.5 to about 2.5 wt %, wherein the sum of the MCT oil, FFA, monolaurin, cetyl esters, vegetable oil such as RBD palm oil, coconut oil and hemp oil and cod liver oil ranges from about 80 wt % to about 100 wt % of the composition.

The hemp oil, in an embodiment, is present in an amount ranging from about 7 wt % to about 13 wt % of the composition, in another embodiment, about 9 wt % to about 11 wt % of the composition and in another embodiment, at about 10 wt % of the composition.

The cod liver oil, in an embodiment, is present in an amount ranging from about 7 wt % to about 13 wt % of the composition, in another embodiment, about 9 wt % to about 11 wt % of the composition and in another embodiment, at about 10 wt % of the composition.

In an embodiment, the hemp oil and the cod liver oil is present in a weight ratio of about 1:1 to about 2:1, respectively; and in another embodiment, in a weight ratio of about 1:1 to about 1.5:1 and, in still another embodiment, they are both present in about equal weight amounts, i.e., about 1:1 by weight.

Further, in an embodiment, the C8/C10 free fatty acids are present in an amount ranging from about 0.15 wt % to about 1.00 wt % and in another embodiment from about 0.20 wt % to about 0.50 wt % and in another embodiment from about 0.25 wt % to about 0.35 wt %.

In another embodiment, the MCT is present in an amount ranging from about 30 wt % to about 50 wt %, and in another embodiment form about 35 wt % to about 45 wt %, and in another embodiment, at about 40 wt %.

Further, in an embodiment, the weight ratio of MCT to C8/C10 free fatty acid, ranges from about 90:1 to about 140:1, and in another embodiment, from about 100:1 to about 120:1.

In an embodiment, monolaurin is present in amounts of less than 1% by weight of the composition. In another embodiment it is present in an amount ranging from about 0.3 wt % to about 0.99% by weight, and in another embodiment, from about 0.5 wt % to about 0.75 wt % of the composition and a still further embodiment from about 0.55 wt % to about 0.65 wt % of the composition.

In an embodiment, cetyl esters are present in an amount ranging from about 0.5% to 3% by weight. In another embodiment, the cetyl esters are present in an amount ranging from about 1% to 3% by weight of the composition.

In an embodiment, the weight ratio of cetyl esters to monolaurin is greater than 1:1 the weight ratio of cetyl ester to monolaurin ranges from about 1:0.5 to about 1:0.7, and in a further embodiment, in about a weight ratio of about 5:3.

The amount of vegetable oil present ranges from about 30 wt % to about 50 wt %, and in another embodiment, from about 35 wt % to about 45 wt % and in another embodiment, from about 36 wt % to about 40 wt %. In this skin protectant, the amount of crude coconut oil is present in greater amounts than RBD palm oil, wherein the weight ratio of crude coconut oil to RBD palm oil ranges from about 0.55 to about 0.45 and in another embodiment, from about 0.52 to about 0.48 and in another embodiment at about 1:1.

The other skin protectant composition is identified as skin protectant A. The major difference between skin protectant B and in skin protectant A is that skin protectant A additionally comprises red palm concentrate besides crude coconut oil and RBD palm oil as the vegetable oil. In addition, the weight ratio of crude coconut oil and are RBD palm oil is reversed. as explained hereinbelow.

In an embodiment, the hemp oil is present in an amount ranging from about 5 wt % to about 15 wt %, cod liver oil is present in an amount ranging from about 5 wt % to about 15 wt % hemp oil, MCT oil is present in an amount ranging from about 30 to about 50 wt %, C8/C10 fatty acid is present in an amount ranging from about 0.1 to about 1.0 wt %, monolaurin is present in an amount ranging from about 0.3 to about 2.0 wt %, vegetable oil is present in an amount ranging from about 30 wt % to about 50 wt %, and cetyl esters are present in an amount ranging from about 0.5 to about 2.5 wt %, wherein the sum of the MCT oil, FFA, monolaurin, cetyl esters, vegetable oil such as RBD palm oil, coconut oil and red palm concentrate, hemp oil and cod liver oil ranges from about 80 wt % to about 100 wt % of the composition.

The hemp oil, in an embodiment, is present in an amount ranging from about 7 wt % to about 13 wt % of the composition, in another embodiment, about 9 wt % to about 11 wt % of the composition and in another embodiment, at about 10 wt % of the composition.

The cod liver oil, in an embodiment, is present in an amount ranging from about 7 wt % to about 13 wt % of the composition, in another embodiment, about 9 wt % to about 11 wt % of the composition and in another embodiment, at about 10 wt % of the composition In an embodiment, the hemp oil and the cod liver oil are present in a weight ratio of about 1:1 to about 2:1, respectively; and in another embodiment, in a weight ratio of about 1:1 to about 1.5:1 and, in still another embodiment, they are both present in about equal weight amounts, i.e., about 1:1 by weight.

Further, in an embodiment, the C8/C10 free fatty acids are present in an amount ranging from about 0.15 wt % to about 1.00 wt % and in another embodiment from about 0.20 wt % to about 0.50 wt % and in another embodiment from about 0.25 wt % to about 0.35 wt %.

In another embodiment, the MCT is present in an amount ranging from about 30 wt % to about 50 wt %, and in another embodiment form about 35 wt % to about 45 wt %, and in another embodiment, at about 40 wt %.

Further, in an embodiment, the weight ratio of MCT to C8/C10 free fatty acid, ranges from about 90:1 to about 140:1, and in another embodiment, from about 100:1 to about 120:1.

In an embodiment, monolaurin is present in amounts of less than 1% by weight of the composition. In another embodiment it is present in an amount ranging from about 0.3 wt % to about 0.99% by weight, and in another embodiment, from about 0.5 wt % to about 0.75 wt % of the composition and a still further embodiment from about 0.55 wt % to about 0.65 wt % of the composition.

In an embodiment, cetyl esters are present in an amount ranging from about 0.5% to 3% by weight. In another embodiment, the cetyl esters are present in an amount ranging from about 1% to 3% by weight of the composition.

In an embodiment, the weight ratio of cetyl esters to monolaurin is greater than 1:1. In another embodiment, the weight ratio of cetyl ester to monolaurin ranges from about 1:0.5 to about 1:0.7, and in a further embodiment, in a weight ratio of about 5:3.

The amount of vegetable oil present ranges from about 30 wt % to about 50 wt %, and in another embodiment, from about 35 wt % to about 45 wt % and in another embodiment, from about 36 wt % to about 40 wt %. In this skin protectant, the amount of RBD palm oil is present in greater amounts than crude coconut oil, wherein the weight ratio of RBD palm oil to crude coconut oil ranges from about 0.55 to about 0.45 and in another embodiment, from about 0.52 to about 0.48 and in another embodiment at about 1:1.

In addition, skin protectant A also comprises red palm concentrate. It is present in an amount ranging from about 0.01 wt % to about 0.20 wt %, and in another embodiment from 0.05 wt % to about 0.15 wt % and in another embodiment, from about 0.08 wt % to about 0.12 wt % of the composition.

The topical compositions described herein without collagen is prepared by art recognized techniques. For example, they are prepared by thoroughly mixing the components described hereinabove with heating optionally in the presence of inert gases at temperatures ranging from about 40° C. to about 80° C. in a vessel until the cetyl ester and monolaurin if present have melted. The heating time should be minimal to prevent vitamin destruction. The headspace in the mixing vessel should be an inert gas, such as argon, helium, and nitrogen and the like. In an embodiment, argon is used. Argon has the advantage of being heavier than air and helps prevent oxygen ingress into the mixing vessel headspace. Once the melt is achieved, the composition is cooled to room temperature. The order of addition is not critical because the mixture is a single-phase fluid once the room temperature solids melt. A homogenous oil is formed. This first topical formulation does not exhibit a rancid fishy oil smell.

The compositions of the present invention that do not contain collagen are single phase anhydrous oils. The turbidity is less than 10 NTU. It ranges from about 10 NTU, such as 9.9, to about 5, and in another embodiment, from about 4 NTU to about 2 NTU. Further, the viscosity of the compositions of the present disclosure in compositions in the absence of collagen is less than 30 cP. It ranges from about 20 to about 40 cP.

The above formulations may contain additional components described hereinbelow, such as fragrances or perfume. For example, if fragrances or perfumes are present, they are present in about 0.01 wt % to about 1.5 wt %.

In an embodiment, the viscosity of the compositions of the present disclosure in which collagen is not present ranges from about 15 to about 30 centipoises at 25° C., in another embodiment from about from about 24 to about 29 centipoise and in a further embodiment about 27.5 centipoise.

All of the compositions described hereinabove contain omega-6 fatty acids, such as linoleic acid. In all of the compositions described hereinabove, the weight ratio of omega 6 fatty acid to omega 3 fatty acid ranges from about 1.0 to about 3.0, and in another embodiment, from about 1.2 to about 2.5 and in a further embodiment, from about 1.4 to about 2.0 and in a further embodiment, from about 1.5 to about 1.9.

In a further embodiment, in the compositions described herein in which collagen is not present, the weight ratio of MCT to the sum of the weights of the total unsaturated triglycerides (from other vegetable oils and the cod liver oil) present in the composition of the present disclosure is either greater than or less than 0.8 and in another embodiment, greater than or less than 1. For compositions containing the hydrophobic analgesic composition and the hydrocolloid composition the aforesaid weight ratio is less than 0.8, for example, from about 0.4 to about 0.7. On the other hand, the hydrocolloid and the skin protectants, have the weight ratio greater than 0.8, such as 1.0 or greater, such as about 1.0 to about 2.2.

Most of the discussion hereinabove relates to compositions that do not contain fish collagen. Another formulation of the present disclosure is those that contain collagen.

A second type of topical formulation comprises collagen in addition to the cod liver oil and monolaurin, MCT and C8/C10 free fatty acids and hemp oil and optionally a pharmaceutically acceptable carrier. Since collagen is one of the larger ingredients, the amount of each of the other ingredient also changes relative to compositions when collagen is not present. In an embodiment, the cod liver oil is present in an amount ranging from about 10 wt % to about 14 wt %, the collagen is present in an amount ranging from about 35% to about 50 wt %, monolaurin is present in an amount ranging from about 2 to about 5 wt %, MCT is present in an amount ranging from about 6 to about 10 wt %, the C8/C10 free fatty acids are present in an amount ranging from about 0.5 to about 1.5 wt % and the hemp oil is present in an amount ranging from about 14 to about 10 wt %. In another embodiment, the cod liver oil is present in an amount ranging from about 11 wt % to about 13 wt %, the collagen is present in an amount ranging from about 40 to about 45 wt %, monolaurin is present in an amount ranging from about 3.8 to about 4.4 wt %, MCT is present in an amount ranging from about 7 to about 9 wt %, the C8/C10 free fatty acids are present in an amount ranging from about 0.8 to about 1.5 wt % and the hemp oil is present in an amount ranging from about 13 to about 11 wt %.

In embodiments, where both fish collagen and cod liver oil are present in the composition, the sum of the cod liver oil and fish collagen is greater than 50% by weight of the composition. In an embodiment, the sum of the cod liver fish oil and the fish collagen ranges from about 50% to about 65 wt % and in other embodiment from about 52% to about 60 wt %. In addition, the weight ratio of fish collagen to cod liver fish oil ranges from about 2.5 to about 5.5 and in another embodiment, from about 3 to about 5 and in a further embodiment from about 3.5 to about 4.4 and in a further embodiment, at about 3.6 to about 3.7.

In an embodiment, where collagen is present, it is present in an amount ranging from about 35 wt % to about 50 wt %, and in another embodiment from about 40 wt % to about 45 wt %.

In an embodiment, where collagen is present, the cod liver oil is present in an amount ranging from about 5 wt % to about 15 wt %, and in another embodiment, from about 8 wt % to about 13 wt %, and in another embodiment, at about 11 wt % to about 12 wt %.

Further, in an embodiment where fish collagen is present, the C8/C10 free fatty acids are present in an amount ranging from about 0.5 wt % to about 1.5 wt %, and in another embodiment, from about 0.8 wt % to about 1.4 wt %.

In another embodiment, where fish collagen is present, MCT is present in an amount from about 6 wt % to about 12 wt %, and in another embodiment from about 7 wt % to about 9 wt %. Without wishing to be bound, it is believed that the role of the MCT is to solubilize the very long triglycerides of the present formulation, and allow them to flow into the collagen pores.

Further, in an embodiment, where fish collagen is present, the weight ratio of MCT to C8/C10 free fatty acid ranges from about 10:1 to about 6:1.

In an embodiment, when fish collagen is present, red palm concentrate is also present. Red Palm concentrate (obtained, for example from ExcelVite, Edison NJ) is a reddish vegetable oil suspension of naturally occurring mixture of tocotrienols/tocopherol complex (Vitamin E) and multi-carotenoids. It consists predominantly of alpha-tocotrienol, beta-tocotrienol, gamma-tocotrienol, delta-tocotrienol, alpha-carotene and beta-carotene. Red palm concentrate is 100 times more concentrated than regular red palm oil. The ratio of total Vitamin E (tocotrienols and tocopherols) to total mixed carotenes (2:1) is exactly the same as found naturally in red palm oil. Red palm concentrate also contains a mixture of other phytonutrients such as gamma-carotene, lycopene, natural plant squalene and phytosterols that are naturally found in red palm oil (*Elaeis guineensis*). Red palm concentrate is viscous, bright red/orange and stains human skin.

Carotenoids are antioxidants in a low oxygen environment and prooxidants in a high oxygen environment. This dual action can be turned into a surprising biofilm disruption technology when optionally combined with omega oil, For example, carotenoids on the surface of skin can partially oxidize and form carotenoid free radicals. Skilled artisans recognize that produced Reactive Oxygen Species (ROS) are among Nature's most active species and are devastatingly effective at inactivating bacteria, including pathogens. Traditionally, ROS are unwanted as they can lead to all kinds of molecular disruption and unexpected events, but on the outside surface of breached skin, the present inventors have found that they may be desirable to help control pathogens in a wound dressing.

The objective is to prevent ROS from entering the skin but leave the external pathogen control mechanism intact. This is what the present inventors have accomplished.

In fact, when present, without wishing to be bound, in both compositions comprising fish collagen and those not containing fish collagen, it is believed that red palm concentrate enters the skin at concentrations up to 0.12% ("max %"). At concentrations greater than 0.12%, red palm concentrate visibly stains the outer skin orange, suggesting that the maximum concentration of red palm concentrate entered the skin and the residual was rejected and deposited on the skin surface.

Without wishing to be bound, it is believed that the rejected concentrate is susceptible to ROS formation on the surface while max % is an antioxidant just below the skin surface. Then one would expect surface ROS to disrupt biofilm and kill pathogens in a wound dressing, but if any ROS enters the skin, then the antioxidant max*% would terminate the ROS and thus prevent ROS-enabled tissue damage. This unexpected benefit would convert red palm concentrate into an impactful ingredient at very low levels (>0.12% w/w). For example, the composition indicated in the examples identified as "Lidocaine Lavage" has red palm concentration 0.1 wt % to 0.4 wt %, such as 0.26 wt % and shows a 3-7 log kill in an in vitro porcine biofilm test. Moreover, skin color is visibly orange-stained. Further, Skin Protectant E has 0.1% red palm concentrate and does not show any log kill activity, and does not show any skin color change.

In the composition of the present invention, when present in the collagen compositions, red palm concentrate is present in amounts greater than 0.12% by weight, and in another embodiment, in at least 0.20 wt %, but no more than 0.4 wt %. At these concentrations, the collagen composition of the present invention does not show any indication of bacterial growth in the wound dressing or of pathogenic activity as deployed in real wounds, although the skin color is slightly orange.

Without wishing to be bound, with respect to the collagen containing formulations containing red palm concentrate present in amounts of 0.12 wt % or greater, it is believed that Vitamins A, C, D & E, which are well known antioxidants migrate throughout the body whether ingested or topical. This suggests that lipid-soluble antioxidant molecules, topically applied, will migrate through the dermis and away from the surface. Unsaturated triglycerides are also well-known antioxidant compounds, particularly PUFA (polyunsaturated fatty acid) oils. These compounds include Essential Fatty Acids (EFA) that the body enzymatically converts into other compounds, e.g. prostaglandins. Other unsaturated triglycerides are simply metabolized by cells and consumed, indirectly moving topical fats away from the skin surface. The net effect of an antioxidant-rich anhydrous lipid mixture is to enter the dermis, be consumed or converted to leave an antioxidant-lean zone just below the surface of the skin. Red palm concentrates >0.12% in an anhydrous lipid base, with an immobile carotenoid fraction, uniquely inhabit the immediate subsurface and skin surface simultaneously. The dual antioxidant/prooxidant nature creates external ROS to disrupt unwanted surface pathogenic biofilms and internal ROS-terminators to prevent ROS disruption of sub-surface, viable tissue. This accelerates wound healing in broken-surface skin.

Formulating red palm concentrate is not straightforward because the blended oil has to penetrate the skin without odor. Red palm oil is well known in skin formulations, but the right amount of carotenoid along with skin penetration is different from the natural concentration. So yellow palm oil (RBD) and crude coconut oil are blended with less red palm concentrate (than in natural red palm oil) for intact skin (where pathogen control is less of an issue), more red palm concentrate in breached skin (where pathogenic biofilm control is a major issue) and an intermediate level of red palm concentrate (and no palm oil) in a slow-release collagen matrix.

In an embodiment where fish collagen is present, the hemp oil is present in an amount ranging from about 15 to about 10 wt %, in another embodiment, hemp oil is present in an amount ranging from about 14 to about 12 wt % and in a further embodiment, hemp oil is present in an amount about 12 wt %.

Where fish collagen is present, in an embodiment, sea salt is present in amounts ranging from about 0.7 to about 1.2 wt %, and in another embodiment, it is present in amounts ranging from about 0.8 to about 1.0 wt %, and in still another embodiment, about 0.9 wt %. The sea salt is a process aid in an anhydrous matrix. In the present formulation, it is added as ground sea salt. The average size of the sea alt crystal is less than about 0.74 microns, and an another embodiment, the average size is less than about 37 microns. As described hereinbelow, the ground sea salt is added after the collagen is mixed with the oil/wax mixture and cooled to room temperature. Sea salt is added during a nitrogen-blanketed whipping. Sea salt acts to make the dry collagen/oil/nitrogen gas mix into freeze/thaw-stable extruded putty. This flow capability is important in treating non-healing wounds. Non-healing wounds have unpredictable crevices and fissures. An anhydrous mixture that can flow into and onto all the wound surfaces is particularly advantageous for wound healing.

In embodiments where fish collagen is present, monolaurin is present in an amount ranging from about 2 to about 6 wt %; in another embodiment, from about 3 to about 5 wt %, and in still further embodiment, about 4 wt %. The actual formulation is interactive with the monolaurin concentration. The monolaurin gels (@≥about 3.5%) to form a structure to make a metastable matrix. Once the gel forms, the ideal amount of collagen is a function of ease of kneading and ease of extrusion.

When the monolaurin is mixed with the fish collagen, the undesirable gelling in the neat oil becomes a benefit in helping to bind oil to the collagen in an anhydrous base.

As with the compositions where fish collagen is absent, in compositions where fish collagen is present, the cetyl esters are optionally present. Thus, in embodiments of the present disclosure in the compositions containing collagen, cetyl ester is optionally present, that is, it is present in 0% by weight to 3% by weight. In embodiments where it is present, it is present in amounts ranging from about 0.5% to about 2.5% by weight. In another embodiment, the cetyl esters are present in an amount ranging from about 1% to about 2.5% by weight of the composition.

As with the formulation in which fish collagen is not present, the topical compositions where fish collagen is present with the cod liver fish oil do not have the rancid fish smell. The addition of the monolaurin, hemp oil and cetyl esters help reduce the malodorous fish smell for the same reasons given hereinabove when discussing the formulations where collagen is not present, the contents of which are incorporated by reference. Thus, in an embodiment, the present disclosure is directed to a method of reducing the fish smell in a pharmaceutical composition comprised of fish collagen and cod liver oil, the method comprises adding monolaurin, hemp oil and optionally, but preferably, cetyl esters in combination in effective amounts to the composition. In an embodiment, when the composition contains fish collagen, the amount of monolaurin present ranges from about 0.06 to about 0.08, the amount of hemp oil ranges from about 0.2 to about 0.3 and the amount of cetyl ester ranges from about 0.02 to about 0.04 per gram of the sum of fish collagen and cod liver oil in the pharmaceutical composition. In another embodiment, the amount of monolaurin present is about 0.07, the amount of hemp oil is about 0.22 and the amount of cetyl ester is about 0.037 per gram of the sum of fish collagen and cod liver oil of the pharmaceutical composition.

In the embodiments where fish collagen is present, the sum of the fish liver oil, the fish collagen, C8/C10 fatty acids, MCT, ranges from about 80 wt % to 100 wt % of the composition.

In an embodiment, in the collagen containing composition, additional component of the topical composition of the present disclosure is a thickener, such as beeswax, candeilla wax, carnauba wax, ceresine wax, microcrystalline wax, zocerite wax, paraffin wax, laurel wax, rice bran wax, vegerite wax and other high melting point waxes, is also present. The presence of these thickener waxes aid in creating compositions having at least two melting points that are separated by more than 5 degrees Celsius in the collagen containing compositions. In an embodiment, the thickener is beeswax. The thickener, such as beeswax, is present in an amount ranging from about 2 wt % to about 6 wt %, and in another embodiment is present in an amount ranging from about 3 wt % to about 4 wt % and in a further embodiment, it is present in an amount ranging from about 3 wt % to about 4 wt %.

The objective of the composition containing collagen is to make a product that can be pumped into useful packages, stored and shipped and then easily extruded into a wound bed. The thickening agent, such as beeswax, makes an already thick product thicker. Unexpectedly, the mixture of cetyl esters, beeswax and monolaurin create two different melting point temperatures in the compositions, which in an embodiment, are eutectic temperatures. The higher temperature along with the lower temperature melting points plugs the collagen pores and prevents oil egress during distribution. The lower melting point temperature allows the composition to soften in the wound and mold to the wound surfaces.

In another embodiment of the collagen containing composition, ascorbyl palmitate ("AP") is additionally present. It is an adhesive. As described hereinbelow. In the collagen containing compositions, ascorbyl palmitate is present in about 0.3 to about 0.6 wt % of the composition, and in another embodiment, it is present at about 0.5 wt %. The Ascorbyl palmitate has a much higher melting point relative to thickening agents such as beeswax. It has a large head group such that when the Ascorbyl palmitate freezes, steric hindrance prevents it from entering deep into the collagen pores. Instead, the Ascorbyl palmitate and the oils form a dense gel. The gel does not penetrate the collagen pores. Without wishing to be bound, it is believed that this gel coats the outside of the collagen pores instead, acting like an adhesive. When the oil/wax mixture is trapped in the pores, the spherical spray-dried collagen is "glued together." The filled-pores are attached together to give the appearance of a uniform paste.

In addition, without wishing to be bound, it is believed that the ascorbyl palmitate stops or retards long-term oil seepage from the collagen matrix. The AP mixture clarifies @160° F. (71.1° C.). When fish collagen is added, the mixture is quenched below the AP freezing point. AP is shaped like a "Tootsie Pop," so it is sterically hindered from entering the collagen pores. Instead, it is believed that the AP fatty esters coat (precipitate on) the outside of each collagen granule. When beeswax or other thickening agents and the other linear esters precipitate, they are mobile greases and penetrate the interior pores of the collagen granule, displacing air, before the AP freezes and plugs the pore holes.

In addition, the sea salt plays a role in preventing oil seepage from the collagen pores. Without wishing to be bound, it is believed that adding Sea Salt in the amounts described herein mechanically helps prevent seepage, but only in combination with AP. It is believed that finely ground salt fits into the interstices between adjacent collagen spheres and "plugs the hole." The salt sticks in the interstices because of the AP sticking to the collagen surfaces, and also stops the seepage. Without the AP, the salt traverses down through the matrix to the bottom; as a result, seeping occurs. The presence of AP prevents this. However, too little salt (less than 0.3 wt %) allows the oil to seep through, while too much salt (greater than 1.8 wt %) allows the oil to seep through. In an embodiment, the salt concentration is about 0.9±0.3 wt %. Without wishing to be bound, it is believed that if there is too little salt, the "holes" are not completely plugged. If there is too much salt, the holes are "stretched," and new pathways are created between adjacent spheres. At 0.9±0.3 wt %, the holes plug, and pathways are not stretched; the AP keeps the salt crystal glued in place.

Thus, AP and sea salt are mechanical process aids that indirectly make heat-stressed collagen matrix stable. Whipping small batches (@ 0.8 kg/3.5 quarts—about 25% of the mixing bowl volume) intimately mixes sea salt and frozen, room temperature matrix, allowing time and added energy for interstice-plugging to occur.

In addition, the sea salt should be ground. The average size of the salt crystal ranges from about 200 Tyler Mesh Screen (about 74 microns) to about 300 Tyler Mesh Screen (about 37 microns). Salt particles within this size range also plug the interstices in the collagen matrix. Larger salt particles migrate to the bottom of packaging containers during storage and distribution, and prevent extrusion emptying of the single use vial.

In an embodiment, another component of the collagen containing composition optionally present is the vegetable oil. As in the compositions not containing fish collagen, the vegetable oil is comprised of palm oil, including red palm oil and RBD palm oil, coconut oil, including crude or refined coconut oil and red palm concentrate and a combination thereto, present ranges from about 7 wt % to about 30 wt %, and in another embodiment, from about 8 wt % to about 20 wt % and in a further embodiment, from about 8.5 wt % to about 15 wt %.

In an embodiment in the composition that contains collagen, coconut oil is present in combination with the red palm concentrate but in the absence of palm oil. In this embodiment, coconut oil is present in an amount ranging from about 7 to about 13 wt %, and in another embodiment, it is present in an amount ranging from about 9 wt % to about 11 wt %, and in another embodiment, it is present in an amount of about 10 wt %. The red palm concentrate in these embodiments is present in an amount ranging from about 0.05 wt % to about 1 wt % and in another embodiment, from about 0.08 wt % to about 0.25 wt % and in another embodiment about 0.2 wt %. This combination of coconut oil and red palm concentrate reduces the amount of oleic fatty acid (from the palm oil) and replaces it with lauric acid (C12:0 from the crude coconut oil). Lauric triglyceride is a better skin moisturizer than oleic triglyceride. Replacing palm oil with its inherent high concentration of Vitamin E with coconut oil which has no Vitamin E is counter intuitive because Vitamin E is widely regarded as an essential vitamin for robust skin health. What has been found is that replacing palm oil with coconut oil and red palm concentrate changes the homogenous oil from a skin moisturizer into an oil that disrupts pathogen growth, best executed in wound healing products.

Without wishing to be bound, it is believed that carotenoids which are present in palm oil concentrate can act as both antioxidants and pro-oxidants under different conditions. The antioxidant property of carotenoids is well-known. It is further believed that carotenoids can switch from anti-oxidant to pro-oxidant behavior as a function of oxygen concentration. Thus, carotenoids in a composition in an oxygen-barrier package will behave as antioxidants and protect the fish oil. Then when the composition is spread over a wound exposed to air, the carotenoids can become pro-oxidants. Some of the oxidized carotenoids become Reactive Oxygen Species (ROS). The ROS, a free radical antimicrobial compound, in turn help reduce the pathogen concentration in infected wounds as shown in FIG. 1. The carotenoids act as both an anti-oxidant and pro-oxidant when the composition is a mixture of fast absorbing compounds, like MCT, and slow absorbing compounds like cod liver oil. As the MCT is absorbed, the carotenoid and cod liver oil concentrate on the skin surface, increasing the microconcentration of the carotenoids at the site of infection. What is observed is faster wound bed granulation and faster wound closure.

It is thought that the addition of different antioxidants, for example, Vitamin E and Ascorbyl Palmitate, increase the antioxidant capacity of the composition because each has its own mechanism of action. Thus, replacing Vitamin E-rich palm oil with nil Vitamin E coconut oil which does not contain significant concentration of Vitamin E and adding red palm concentrate increases the in vitro antioxidant capacity (in combination with oxygen barrier packaging) but decreases the in vivo antioxidant capacity and increases the pro-oxidation ROS sufficiently that infection is controlled without a negative effect on the healing rate. Adding MCT to the crude coconut oil and carotenoids accelerates the healing process by concentrating the ROS on the surface where there can be infection. It is counterintuitive to use the same composition to be an antioxidant during storage and distribution and a source of pro-oxidant, antimicrobial ROS when the composition is applied to the wound, as in the present formulation.

When palm oil is used with red palm concentrate, the palm oil Vitamin E and the carotenoids work together to keep the carotenoids in the anti-oxidant mode. The Vitamin E absorbs the ROS before any killing takes place and terminates free radical propagation. Thus, bacterial kill is not observed. But, when coconut oil replaces palm oil, there is less vitamin E in the mixture. The carotenoids are anti-oxidants in an oxygen barrier package and then are pro-oxidants when applied to skin and exposed to air. There is little vitamin E, so the carotenoid-produced ROS is not quenched and goes on to kill bacteria. Multi-log bacterial kill is observed.

In an embodiment, coconut oil is the only vegetable oil present in the compositions comprised of fish collagen described herein. In an embodiment, when it is the only vegetable oil present, it is present in an amount ranging from about 7 to about 13 wt %, and in another embodiment, it is present in an amount ranging from about 9 wt % to about 11 wt %, and in another embodiment, it is present in an amount of about 10 wt %. Coconut oil essentially contains saturated medium chain length triglycerides. The melting point of coconut oil is close to room temperature. When cooled, coconut oil freezes slowly. This melting point allows coconut oil and fish collagen/wax mixtures to be whipped into a stable "whipped butter." When whipped under an inert gas blanket, the specific gravity drops from about 0.81 to about 0.78. This small change reduces the ambient viscosity from "hard fudge" (cannot be extruded with thumb and forefinger pressure) to about 65,000 cP, thick but extrudable with thumb and forefinger pressure.

The oil fraction compositions of the present disclosure having fish collagen present have a surface tension of less than 35 mN/m at 25° C. In an embodiment of the present disclosure, the surface tension ranges from about 30 mN/m to about 40 mN/m at 25° C. For example, in an embodiment, the surface tension is about 31.7 mN/m at 25° C. Low surface tension is critical for the oil wax mixtures to percolate into the pores and completely displace the original air. During high temperature mixing, the collagen pore specific gravity increases from about 0.3 to about 0.81 and then is steady, indicating that all the gas has been displaced. If residual pore air were permitted to remain, it would oxidize the fish oil and make it rancid during distribution, making it unacceptable for wound healing because the triglyceride would become an epoxide or other oxidized product. Thus, in the compositions containing collagen, the air is substantially removed therefrom, that is, air is present in less than 0.1 wt % of the compositions, and in another embodiment less than 0.01 wt %, and in a further embodiment, less than 0.001 wt % of the composition.

In the embodiments where fish collagen is present, in the composition of the present disclosure, the weight ratio of MCT relative to the amount of oleic acid present ranges from about 2:1 to about 0.2:1, and in another embodiment, from about 1.5:1 to about 0.5:1. Another ratio that is important is the weight ratio of C8/10 MCT (from manufactured C8/10 and natural C8/10 in crude coconut oil (~14%) and sum of the weights of amount of all unsaturated triglycerides present. In other words, the sum of C8:0+C10:0 (MCT) is less than the sum of all unsaturated triglycerides (mono+PUFA). As described herein above, the weight ratio of MCT relative to the sum of all unsaturated triglycerides is less than 0.8.

When the difference between these two ratios (sums) is greater than 1, the resulting composition has at least two melting points which can be exploited for purposes of packing the oil into vials.

The compositions of the present disclosure containing collagen are turbid pastes. They are very difficult to work with. However, a property of the collagen containing compositions of the present disclosure that can be exploited is that the compositions of the present disclosure having at least two melting points that are separated by at least 5° C. and that the lower melting point is less than 37° C. and the upper melting point is above 37° C.

Without wishing to be bound, it is believed that when the difference between these two ratios are greater than about 1, the resulting composition has two different melting points that are separated by more than 10° C. In embodiments, these compositions are eutectic compositions having at least two eutectic melting points. This property of having at least two melting points makes the compositions of the present invention very useful as a pharmaceutical.

Compositions of the present disclosure containing collagen are not porous pastes. When porous pastes are sheared by pumping through filling machines, the pores are compressed, and entrapped oils can be extruded from each pore. The result is a two-phase "reduced-oil concrete" and free oil. Consistent vial filling cannot be achieved, and FDA-compliant processing is infeasible. On the other hand, the dual freezing points in compositions of the present disclosure containing fish collagen in combination with high melting point Ascorbyl palmitate, MCT, and low surface tension oil makes an oil wax mixture that will completely fill pores during high temperature processing. Without wishing to be bound, it is believed that as the temperature is lowered, the oil/wax mixture freezes, plugging the collagen pores with entrapped oil. The oil content overfills the pores. The MCT leaves the pores and is absorbed directly into the fish collagen mass, reducing the amount of free oil held in the pores. In an embodiment the sum of the weight of the total triglycerides (saturated and unsaturated triglycerides) to collagen ranges from about 0.9 to about 1.1, and in another embodiment it is about 1:1. When this weight ratio is in the range herein, especially at about 1:1, the pores are filled and MCT is absorbed into the fish collagen mass. Meanwhile the Ascorbyl palmitate/oil mixture coats the spherical, pore-filled collagen granules and glues them together to make a hard, ambient solid. This solid cannot be processed in a commercial filling machine, but it will not seep oil. The coconut oil allows the cooled hard solid to be whipped under an inert gas blanket in a typical Hobart-type whisk mixer. The hard solid is now interspersed with stable inert gas pockets. The gassy viscosity is still thick, ~65,000 cP, but it can be pumped with commercially available paste, drum-emptying systems such as Muller GMBH, Rheinfelden Germany into single use vials. Thus, the unexpected combination of dual melting point oil/wax mixture (for example beeswax, coconut oil, monolaurin and cetyl esters NF), MCT and ascorbyl palmitate allows whipping, pumping, extrusion and flowability in the wound bed without oil seepage.

A second melting point (lower melting point) becomes important as the product is used. The practitioner dispenses the paste at 25° C. into a wound bed or on the skin disorder at 37° C., above the second melting point. At 37° C., the composition containing fish collagen melts, and the paste becomes more fluid. Fluid paste is extruded as "stripes" of paste. Without wishing to be bound, it is believed that the now-body-temperature stripes relax and flow into the interstices and irregularities of actual wound beds. But reality is still more complex in that packed product can experience high temperature excursions during distribution. If the temperature rises to ~45° C., some of the whipped-in inert gas is lost and the product re-thickens. But the thickening is not so much that it cannot be extruded from the already-filled vial. The combination of a composition comprised of fish collagen and triglycerides within the ratio range described herein have at least two melting points separated by at least 5° C. between the high melting temperature and the low melting point temperature. Ascorbyl palmitate and MCT allows machine processing, distribution stability and practitioner-friendly dispensing and finally complete wound bed coverage.

Thus the oil/wax/collagen mixture of the present disclosure has at least two melting point temperatures, for example, at least two eutectic temperatures, separated by at least 10° C. such that the higher melting point is above 37° C. and a lower melting point is below 37° C. Moreover, in the compositions of the present disclosure containing fish collagen, the lower melting point is separated from the upper melting point by at least 5° C., in another embodiment, by at least 10° C. and in another embodiment, by at least 13° C.

The collagen containing composition of the present invention is an oily composition. At 25° C., the surface tension of the oil/wax mixture is less than 35 mN/m. In an embodiment, the surface tension of the composition described herein comprised of fish collagen have a surface tension at 25° C. range from about 29 mN/m to about 33 mN/m, and in a still further embodiment, from about 31 mN/m to about 32 mN/m.

In an embodiment, as an anhydrous oil, there are no emulsifiers present in the fish collagen compositions of the present disclosure. However, but there are process aids that help further separate the melting point temperatures. Examples of these process aids are ethyl linoleate and triethyl citrate. When present, they are typically present each at from about 1 to about 3 wt % and in an embodiment are each at about 2%. Skilled artisans will recognize that the composition with collagen is carefully balanced to exclude air from the pores, keep oil in the pores during processing and distribution, seal the pores for long term stability, allow easy thumb/forefinger extrusion and then have the composition mold over wound bed irregularities to ensure complete coverage of the wound bed.

In both the compositions wherein the collagen is present and collagen is absent, the hempseed oil, crude coconut oil and palm oil provide a smooth texture when applied to the skin of the patient. However, when collagen is present in the composition, there is also an additional advantage. When present in the amounts indicated herein, there is also no weeping observed. Without wishing to be bound, it is believed that that the C8-C22 triglycerides of these oils enter into the collagen pores and remains there (in the absence of pump shear.) The long chain triglycerides (C18-C22) are stored in the collagen pores and are stable (in the absence of pump shear). The room temperature saturated liquids (C6-C10) do not remain in the pores but are absorbed directly into the fish collagen mass itself. The monounsaturated triglycerides, for example, oleic triglycerides (C18:1) remain in the pores. This distinction is important because oils absorbed into the fish collagen mass do not weep out; room temperature unsaturated liquids do leak out. The solution was to replace palm oil (35 to 50% C18:1) with crude coconut oil (6.5% C18:1). This increased the MCT-to-C18:1 ratio and eliminated ~90% of the seepage. Adding Ascorbyl palmitate eliminated the remaining seepage. Increasing the weight ratio of the total triglyceride (saturated and unsaturated) to-fish collagen to the weight ratio described herein, such as about 1:1 weight ratio, and inert gas whipping allowed the product to flow in the wound bed or on the skin condition.

Fish collagen is the active ingredient, so the formulation objective is to maximize the fish collagen wt %. The oils make the fish collagen flow. The waxes, sea salt, whipping and process aids are necessary to prevent seepage and to help control wound bed pH and inhibit pathogens. In an embodiment, the ideal weight ratio of triglycerides to fish collagen is about 1:1. Mixing and matching various triglycerides does not materially affect the collagen delivery. In an embodiment, the ratio of triglycerides to fish collagen ranges from 1.1 to 1.2 and in a commercial embodiment, the ratio is about 1:1.01. In other words, having the weight ratio of the total triglyceride to collagen being in the range describe herein, such as about a 1:1 triglyceride to fish collagen weight ratio is beneficial but it takes a complex series of process aids to make the product manufacturable and user-friendly.

In addition, the viscosity of the collagen containing composition ranges from about 60,000 cP to about 85,000 cP at 25° C., and in another embodiment, from about 65,000 cP to about 80,000 cP and in a further embodiment, from about 70,000 cP to about 75,000 cP.

All of the compositions described hereinabove containing fish collagen contain omega-6 fatty acids such as linoleic acid. In all of the compositions described hereinabove comprised of collagen, the weight ratio of omega 6 fatty acid to omega 3 fatty acid ranges from about 1.0 to about 3.0, and in another embodiment, from about 1.2 to about 2.5 and in a further embodiment, from about 1.4 to about 2.0 and in a further embodiment, from about 1.5 to about 1.9.

All of the compositions described hereinabove comprised of fish collagen, the weight ratio of MCT to the sum of the weights of the total monounsaturated triglycerides (from other vegetable oils and the cod liver oil) present in the composition of the present disclosure is less than 1.0 and in another embodiment, less than 0.8.

In an embodiment, the compositions of the present disclosure containing fish collagen are prepared by art recognized procedures. For example, all of the components except the collagen and sea salt and any fragrances are mixed together with stirring at a temperature sufficient to homogenously melt the components and form a homogenous paste. Typically, the composition is heated at temperatures ranging from about 130° F. to about 200° F., in an embodiment, and in another embodiment from about 150° F. to about 170° F. and in another embodiment at about 140° F. Collagen is added at temperatures at greater than 130° F., for, example at temperatures at about 150° F. to about 170° F. and the collagen is mixed in with the other components. When substantially homogenous, when the pores of the collagen is filled with oils, which takes about ten to about twenty minutes, the composition is cooled to room temperature. The composition ground sea salt is added at ambient temperatures. In an embodiment, it is added in an inert atmosphere, such as in the presence of an inert gas, such as nitrogen, and the composition is again mixed until the composition is substantially homogenous.

It is well known that free fatty acid is a skin irritant. Prior art formulations use triglycerides in which the free fatty acid is neutralized and removed. The skin, however, produces free fatty acids and sebum, a wax, as a first line of defense against pathogenic infections. In an embodiment, when collagen is present the weight ratio of cetyl esters to C8/C10 fatty acid is about 3:1. In this weight ratio, the C8/C10 fatty is not irritating. At lower ratios (example 1:1), the composition creates a tingling skin sensation, an indicator of future irritation. At a higher ratio (example 4:1), there was no antimicrobial benefit. The weight ratio of about 3:1 retained the silky smooth finish without odor and without skin irritation. Thus the free fatty acid reinforces the acid mantle of the skin without harm. In another embodiment, the weight ratio is about 2:1. Excess monolaurin is added to increase the wax concentration in the collagen matrix for phase stability. Excess monolaurin is added to the collagen matrix (a leave-on product) because monolaurin is a well-known, but controversial antimicrobial agent. Monolaurin is the antimicrobial agent in Mother's milk, for example. The controversy is that the activity is not rapid and it does not kill everything and therefore does not meet current FDA definitions of antimicrobial activity. However, in a wound care environment, slow effectiveness is a major benefit Monolaurin "tilts" the bacterial "playing field" such that commensal bacteria thrive while pathogens are inhibited.

Cetyl esters are also process aids. The collagen matrix is a metastable mixture in that it is not inherently stable @ 25° C. The doctor wants putty that can be extruded into the wound and flow into all the interstices. The FDA is used to reviewing products that are entirely homogeneous. These competing desires are difficult to execute in practice. In the collagen matrix, the cetyl ester can range up to 3% to thicken the matrix so oil does not "weep" out. The sea salt can be adjusted to the concentrations described herein to maintain the putty consistency. In an embodiment, the material percent changes are very small and the phase stability/viscosity changes are large. Skilled artisans recognize that small changes may be necessary when natural products change during different harvesting seasons. During processing and packaging, the product is kept chilled to prevent weeping so that absolute consistency is maintained. Once filled into unit dose packs, the doctor can knead the flexible package to achieve temporary homogeneity and have putty-like flow.

In an embodiment of the present disclosure in which fish collagen is present, the composition comprises MCT oil, FFA, Monolaurin, cetyl esters, thickener, such as beeswax, crude coconut oil, ascorbyl palmitate, red palm concentrate, hemp oil, cod liver oil, fish collagen and ground sea salt. In an embodiment, the MCT is present in an amount ranging from about 6 wt % to about 10 wt %, FFA is present in an amount from about 1.0 wt % to about 1.7 wt %, cetyl esters are present in an amount from about 1.8 wt % to about 2.5 wt %, monolaurin is present in an amount ranging from about 3 wt % to about 6 wt %; thickening agent, such as beeswax, is present in an amount ranging from about 2 wt % to about 8 wt %, crude coconut oil is present in an amount ranging from about 5 wt % to about 15 wt %, red palm concentrate is present in an amount ranging from about 0.1 wt % to about 0.3 wt %. hemp oil is present in an amount ranging from about 9 wt % to about 15 wt %, cod liver oil is present in an amount ranging from about 9 wt % to about 15 wt %, ascorbyl palmitate is present in an amount ranging from about 0.2 wt % to about 1 wt %, fish collagen is present in an amount ranging from about 40 wt % to about 45 wt %, and ground sea salt ranging from about 0.7 wt % to about 1.2 wt %, wherein the sum of the weights of the above-identified ingredients ranges from about 90 wt % to about 100 wt % of said composition. Additional ingredients may be present, as described hereinbelow. For example, in an embodiment, process aids, such as triethyl citrate and/or ethyl linoleate, are present in an amount in total ranging from about 3 wt % to about 5 wt %. However, the total of the weights of the components equals 100 wt % of the composition. In an embodiment, the weight ratio of hemp oil to cod liver oil ranges from about 1:1 to about 1.5:1 and in another embodiment it is about 1:1. In an embodiment, the weight ratio of MCT to FFA ranges from about 4:1 to about 10:1. Moreover, in another embodiment, the weight ratio of monolaurin to cetyl esters ranges from about 1.5:1 to about 2.5:1, and in another embodiment, about 2:1. In an embodiment, the weight ratio of the sums of the weights of all of the triglycerides to fish collagen ranges from about 0.9 to about 1.1:1, and in another embodiment, at about 1:1. In another embodiment, the composition comprises crude coconut oil in an amount ranging from about 10 wt % to about 12 wt %, MCT in an amount ranging from about 7 wt % to about 9 wt %, hemp oil in an amount ranging from about 10 wt % to about 14 wt %, cod liver oil in an amount ranging from about 10 wt % to about 14 wt %, monolaurin in an amount ranging from about 4 wt % to about 5 wt %, cetyl esters in an amount ranging from about 2 wt % to about 3 wt %, FFA ranging from about 1.1 wt % to about 1.5 wt %. the thickening agent, such as beeswax, ranging from about 3 wt % to about 5 wt %, fish collagen ranging from about 40 wt % to about 42 wt %, sea salt, ranging from about 0.8 wt % to about 1.0 wt %, and red palm concentrate at about 0.2 wt %, wherein the sum total of the above-identified ingredients ranges from about 90 to about 100% of the composition. In an embodiment, the viscosity of this composition ranges from about 60,000 cP to about 90,000 cP at 25° C., in another embodiment from about from about 65,000 cP to about 80,000 cP and in a further embodiment about 70,000 cP. As used herein, any composition of the present disclosure which falls within the scope of this embodiment will be identified as composition D.

Both the composition with and without collagen are anhydrous.

In both the compositions with and without collagen, the cetyl esters, which are a waxy compound, forms an odor occlusive film over the skin. It and the MCT help reduce the fish odor. Without wishing to be bound, it is believed that the MCT drags most of the polyunsaturated triglycerides into the skin, but not all. Further, it is believed that the cetyl esters form a silky-smooth film over the residual polyunsaturated fatty acid triglycerides, protecting them from oxidation. Furthermore, it is believed that the oxidized off odors cannot pass through the cetyl ester film to reach the nose. In an embodiment in both types of compositions containing fish collagen and where fish collagen is not present, the composition may contain, fragrances or perfumes to further conceal the rancid fishy smell, However, if present, the perfumes or fragrance are present in less than about 2 wt %, such as for example, from about 0.5 wt % to about 1.5 wt %.

As indicated hereinabove, the topical compositions of the present disclosure substantially eliminate the rancid fish odor of the cod liver oil. Without wishing to be bound, it is believed that the fishy odor, not the rancid odor, is caused by the presence of trimethylamine. It is believed that the concentration of trimethylamine in the present compositions described herein is greatly reduced relative to that which is present in cod liver oil. In an embodiment, the concentration of trimethylamine in the present composition, whether collagen is present or not is less than 10 ppm.

In compositions of the present disclosure, described hereinabove, where collagen is present or is not present, in an embodiment a mixture is provided of omega fatty acids in combination with MCT+ vegetable oil, such as coconut oil wherein the sum of the weights of MCT and vegetable oil, such as coconut oil, when present is greater than 25% of the total triglyceride weight. As described hereinabove, it is believed that the MCT drags the long chain fats through the stratum corneum. The compositions of the present disclosure, are capable of driving longer fats (definition: $C \geq C_{14}$) through the stratum corneum without leaving oxidizable fats on the surface to create rancid skin odor, regardless of whether fish collagen is present or not. This is effected by making the sum of MCT+vegetable oil, such as coconut oil ($C<C_{14}$) greater than 25% of the total triglycerides (sum of all triglyceride chain lengths) so that the solvent action of $C<C14$ drags $C \geq C14$ through the stratum corneum into the dermis.

This is a table of exemplary ratios of 4 exemplary products in the present disclosure:

| | MCT + Coconut Oil | Sum Triglycerides | Lower/Higher Ratio |
|---|---|---|---|
| Collagen Matrix CN | 18% | 42% | 43% |
| Omega Oil BY | 30% | 98% | 31% |
| Lidocaine Lavage BZ | 46.64% | 97% | 48% |
| Hydrocolloid BX | 47.50% | 97.84% | 49% |

Additionally, adding Cetyl esters provides a semi-occlusive wax coating that prevents any remaining surface unsaturated triglycerides from oxidation before absorption. This distinction is important because once an omega-3 triglyceride oxidizes (rancid smell); it is no longer an essential fatty acid. It becomes some other oxidized long chain compound.

The composition of the present disclosure whether containing fish collagen or not, can be used as a carrier for drugs useful for treating skin conditions or wounds, especially analgesics in pain killing effective amounts. For example, the compositions of the present disclosure may contain a medicament which numbs tissue and reduces pain associated with the skin condition or wound. When present, the drug is present in an amount to be effective for its indicated efficacy. Thus, for example, when lidocaine is the drug, it is present in an amount to reduce the pain of the skin condition or wound. For example, in an embodiment, it is presented in an amount ranging from about 0.5% to about 1.5% by weight of the composition.

The compositions described herein are topically applied to the skin. "Topical" administration means local, external administration to skin and/or to a wound. The composition may be topically administered directly to all or to part of the area of skin or the wound in need of treatment, or peripherally to the skin area or the wound.

A wide variety of optional components/ingredients may be included in the compositions of the present invention, regardless of whether fish collagen is present or not. For example, the compositions may include absorbents, abrasives, anticaking agents, antifoaming agents, antimicrobial agents, binders, biological additives, buffering agents, bulking agents, chemical additives, biocides, denaturants, cosmetic astringents, drug astringents, external analgesics, film formers, humectants, opacifying agents, fragrances, pigments, colorings, essential oils, skin sensates, emollients, skin soothing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in Harry's Cosmedcology, 7$^{th}$ Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2$^{nd}$.ed., deNavarre (Van Nostrand 1962-1965); and in The Handbook of Cosmetic Science and Technology, 1$^{st}$ Ed. Knowlton & Pearce (Elsevier 1993).

The compositions can be formulated as a gel, ointment, cream, balm, or lotion. It may be administered in any one of those forms or administered as an oil-impregnated wipe or spray, such as an aerosol spray, including a bag-on-valve aerosol spray. Topical administration can also be accomplished with a liquid spray, an aerosol, or via iontophoresis, or through the use of liposomes, microbubbles and/or microcapsules. Gels, ointments and creams may be formulated with additives, for example, with an aqueous or oily base with the addition of suitable thickening (e.g., wax, beeswax, PEG 4000, PEG 600, hard paraffin) and/or gelling agents (e.g., hydroxypropyl cellulose, carboxymethyl cellulose (CMC)). Lotions may be formulated with additives, such as an aqueous or oily base and can also generally contain one or more stabilizing agents (e.g., polyoxyethylene sorbitan monolaurate, carboxy methyl cellulose), oil soluble dispersing agents (e.g., sodium oleate, propylene glycol), suspending agents (e.g., methyl cellulose, chitosan, accacia, carboxymethyl cellulose, tragacanth, pectin), thickening agents, and/or coloring agents (e.g., dyes, lackes). In some embodiments, for example, the topical compositions can include pluronic gels, polaxamer gels, hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (carbopols). Embodiments may also include creams/ointments conventionally used for topical cosmetic or pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA. Oil soluble anti-oxidizers, such as Vitamin E, and astaxanthin, may also be present Oil soluble vitamins, such as Vitamin D can be added. Oil soluble fragrances such as vanilla, lemon oil and lavender and oil-soluble coloring agents may be added. In addition sebum can be added. Further, benzethonium chloride, methylbenzethonium chloride and benzalkonium chloride may be present.

The stabilized formulation can be applied directly to the skin or wound as a gel, ointment, liquid, cream, or the like as described above. Alternatively, the stabilized formulation is administered in the form of a wound dressing, wherein the composition of the present disclosure is applied onto a wound dressing and the wound dressing with the composition of the present disclosure is than applied to cover the area of the skin at the location of the skin condition or wound. As used herein, the terms "wound dressing" and "dressing" refer broadly to any substrate when prepared for, and applied to, a wound for protection, absorbance, drainage, improvement of cell environment, etc., and may include any one of the numerous types of substrates and/or backings that are commercially available, including films (e.g., polyurethane films), hydrocolloids (e.g., hydrophilic colloidal particles bound to polyurethane foam), hydrogels (e.g., cross-linked polymers containing about at least 60% water), foams (hydrophilic or hydrophobic), calcium alginates (e.g. non-woven composites of fibers from calcium alginate), silicone, collagen, keratin, and cellophane (e.g. cellulose with a plasticizer). For example, the stabilized formulation can be applied to the surface of, or incorporated into, a solid contacting layer such as a dressing gauze or matrix. Suitable gauze dressings may include, for example, dry woven or non-woven sponges, swabs, bandages and wraps with varying degrees of absorbency. Exemplary fabric composition may include, for example, cotton, polyester or rayon. In certain embodiments, gauzes and non-woven dressings may be available sterile or non-sterile in bulk and with or without an adhesive border. In certain embodiments the dressings also comprise one or more additional pharmaceutically active compound and/or carrier agent, including for example, saline, oil, zinc salts, petrolatum, xeroform and scarlet red.

Other additives that may be present in the formulations described herein whether containing collagen or not containing collagen include, for example, antioxidants and preservatives. Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid.

In embodiments of the present invention, the composition can comprise any one or more of therapeutically active compounds and pharmaceutically and/or cosmetically acceptable diluents, excipients or carriers. A composition that comprises the stabilized formulation can be formulated for topical application as described herein and sealed in an air tight container suitable for a single use. Such a composition can be used to treat any of the skin conditions and/or wounds and/or burns described herein, for example a skin condition and/or wound.

The compositions of the present invention are useful for treating wounds and skin conditions and burns. As used herein, a wound is defined as an injury to living tissue of the mammal in which the skin is cut or broken. It includes incisions, cuts, including paper cuts and shaving cuts. However, as defined herein, the wound may or may not be accompanied by bleeding. Examples of wounds treatable by the composition described herein include, but are not limited to, incisions (including surgical incisions), lacerations, abrasions (such as in dermabrasion and microdermabrasions), ulcers, and the like. In some embodiments, the wound is a diabetic wound ulcer.

In an embodiment, the composition with fish collagen is used as a hemostat for minor wounds. For example, after a femoral artery access procedure, as described in U.S. Pat. No. 8,353,929, the contents of which are incorporated by reference, the apparatus therein described an FIG. 22 can be used for closure of the wound, the fish collagen paste described herein replaces the powdered hemostat. In this embodiment, the paste configures to the irregularities caused by the mechanical skin compression by the closure device. The fish collagen absorbs blood and exudate and causes immediate hemostasis of the wounds described therein.

The wound may be the result of an accidental injury or be the consequence of a medical procedure. The wound may be a surgical incision. The wound may be an ischemic tissue flap, such as in the course of cosmetic surgery. The wound may be one caused in the course of other cosmetic surgery, such as dermabrasion, microdermabrasion, chemical peel, laser resurfacing, etc. The wound may be a chronic injury.

The compositions of the present invention are useful for treating chapped skin and other skin disorders. Examples of skin disorders include acne, psoriasis, eczema, dermatitis, alopecia, rosacea, burns, chapped skin, poison ivy, shingles and the like.

The term "acne" is meant to include any skin condition where a skin pore becomes blocked and/or thereby becomes inflamed. The term acne includes without limitation superficial acne, including comedones, inflamed papules, superficial cysts, and pustules; and deep acne, including deep inflamed modules and pus-filled cysts. Specific acne conditions can include, but are not limited to, acne vulgaris, acne comedo, papular acne, premenstrual acne, preadolescent acne, acne venenata, acne cosmetica, pomade acne, acne detergicans, acne excoriee, gram negative acne, acne rosacea, pseudofolliculitis barbae, folliculitis, perioral dermatitis, and hiddradenitis suppurativa. Acne is a common inflammatory pilosebaceous disease characterized by comedones, papules, pustules, inflamed nodules, superficial pus-filled cysts, and (in extreme cases) canalizing and deep, inflamed, sometimes purulent sacs. Acne involves an interaction between hormones, keratinization, sebum, and bacteria that somehow determines the course and severity of acne. It often begins at puberty, when the increase in androgens causes an increase in the size and activity of the pilosebaceous glands. The earliest microscopic change is thought to be intrafollicular hyperkeratosis, which leads to blockage of the pilosebaceous follicle with consequent formation of the comedo, composed of sebum, keratin, and microorganisms, particularly *Propionibacterium acnes*. Lipases from *P. acnes* break down triglycerides in the sebum to form free fatty acids (FFA), which irritate the follicular wall. Retention of sebaceous secretions and dilation of the follicle may lead to cyst formation.

Skin conditions also include, but are not limited to, dermatological conditions linked to disorders of keratinization involving differentiation and proliferation, in particular, acne vulgaris, comedonic or polymorphic acne, nodulocystic acne, acne conglobata, senile acne and secondary acnes such as solar, drug or occupational acne; for other types of keratinization disorders especially ichthyoses, ichthyosiform conditions, Darier's disease, palmoplantar keratoderma, leukoplakia and luecoplakiform conditions or lichen and lichen planus; dermatological disorders having an inflammatory or immunoallergic component, in particular, all forms of psoriases, either cutaneous, mucosal or ungual, and psoriatic rheumatism, and cutaneous atopy such as eczema or respiratory atopy, dry skin, inflammation of the skin, solar erythema, skin allergies or other skin disorders of the epidermis and dermis.

Psoriasis is a skin condition characterized by hyperplasia of keratinocytes resulting in thickening of the epidermis and the presence of red scaly plaques. The lesions in this chronic disease typically are subject to remissions and exacerbations. There are several patterns, of which plaque psoriasis is the most common. Guttate psoriasis, with raindrop shaped lesions scattered on the trunk and limbs, is the most frequent form in children, while pustular psoriasis is usually localized to the palms and soles. The classical inflammatory lesions vary from discrete erythematous papules and plaques covered with silvery scales, to scaly itching patches that bleed when the scales are removed. Psoriasis is a condition in which cell proliferation is increased up to 10 times the normal rate for an individual. The skin is the largest portion of the human body which is comprised of cells within three skin layers. Each of the skin layers is in a constant state of growth with the outer layer being formed of predominantly dead tissue which is naturally being discarded at a normal rate. Replacement of cells from underlying layers is accomplished by cell division and maturation where cells move upwardly and outwardly at a rate which varies dependent upon the age, sex, and/or health of an individual. Psoriasis causes an increased turnover of cells, which in turn increases the rate of cell growth and cell death. This increased rate of cell growth and cell death may result in injuries and/or disorders which accompany the increased synthesis of all tissue components and further elevate the strain placed upon skin or other tissue and the bio-synthetic capabilities of the cells within the affected area.

The terms eczema and dermatitis are generally used names for severe inflammation of the skin, usually with redness, swelling, oozing, rusting or scaling of lesions which are usually itchy. Eczema may take the form of contact dermatitis (due to skin contact with the cause) or atopic dermatitis in individuals who are "atopic" or allergic by nature. If the scalp is involved the disorder is known as seborrheic dermatitis. Dermatitis can be caused by chemicals, plants, shoes, clothing, metal compounds and even medicines used to treat dermatitis. In atopic dermatitis environmental temperature, humidity changes, bacterial skin infections, airborne allergens and garments, e.g., wool, may all bring about dermatitis. In an embodiment, the collagen paste described herein is used as a skin scrub. The ground sea salt and fish collagen gently abrade damaged and dead cells from the skin surface. Simultaneously, the oils are absorbed. The combination of mechanical removal of damaged cells and concurrent feeding of viable cells gives the skin a vibrant soft silky feel that is immediately apparent to the user.

Alopecia is a skin condition that results in the loss of hair on the scalp and elsewhere. It usually starts with one or more small, round, smooth patches and occurs in males and females of all ages. Loss of hair in one or several small spots is common, but it is possible to lose all scalp hair (alopecia totalis), or every hair on the body (alopecia universalis), which is rare.

The skin condition, rosacea is of an unknown origin. It usually affects the middle third of the face causing skin redness, prominent vascularization, papules, pustules and swelling, as well as a predisposition to flushing and blushing. However, rosacea can also occur on other parts of the body including the chest, neck, back, or scalp. The blood vessels near the skin dilate and become more visible there through, resulting in telangiectasia. The resulting papules and pustules resemble teenage acne, and are frequently mistaken for the same. Unlike acne, rosacea does not have blackheads or whiteheads. Rosacea, however, can occur in all age groups and in both sexes, where it tends to be more frequent in women but more severe in men. The flushing and blushing regions of the face are affected by rosacea. Emotional factors such as anxiety, embarrassment, or stress may evoke or aggravate rosacea. In addition, a flare-up may be caused by environmental or climate variances, and UV exposure is known to aggravate rosacea. Furthermore, diet is also known to aggravate rosacea. Spicy foods, alcoholic beverages, hot beverages, and smoking are known to cause flare-ups. Rosacea is not only an aesthetic complication. Rosacea is a chronic disease that has rarely been documented to reverse its progression. If untreated, the condition worsens and spreads. Untreated rosacea may cause a disfiguring nose condition called rhinophyma, which is characterized by a bulbous, red nose and inflamed cheeks. Severe rhinophyma may require surgery, an invasive procedure that may be avoided by timely treatment. Another problem of advanced rosacea is ocular. Persons afflicted with rosacea may experience conjunctivitis, a burning and grittiness of the eyes. If untreated, it may lead to serious complications such as rosacea keratitis, which damages the cornea and may impair vision.

Burns involve a type of skin integrity rupture. Burns represent one of the most painful processes that can be established in this tissue, needing the establishment of a coordinated therapy to help its recovery and pain treatment. Burns can be caused by several factors, among which, exposure to high or low temperatures, exposure to chemical compounds, by electricity, by exposure to radiation and mechanical friction. Burn severity and its risk are evaluated according to the amount of affected tissue and depth reached. The amount of affected tissue is represented by the percentage of burned corporeal surface (BCS). In this type of evaluation, burns can be divided into small, moderate, large, or massive burns, where regions inferior to 15% of BCS, from 15% up to 49% of BCS, from 50% up to 69% of BCS and over 70% of BCS, respectively. The extension of the affected area is determined through Lund-Browder scheme, which takes into consideration the burn proportion, in accordance with the age of the burned patient. Another rule that is most used for determining the extension of the affected area is that known as Wallace Rule or Rule of Nines, a technique less efficient than the foregoing, however, easy to memorize, being very much employed in emergency cases. This rule applies a value equaling nine or nine multiple to the affected parts, being 9% for each superior member, 9% for the head, 18% for each inferior member, 18% for each torso face and 1% for the genitalia.

The classification as first, second and third degree corresponds to burn depth. The first-degree injury corresponds to the burn that affects the skin most external layer (epidermis), not producing hemodynamic alterations, however the affected region is found hyperemic in absence of blisters or phlyctenae. This type of injury can be observed in erythemae resulting from sunrays or heated water. The second-degree injury affects either the epidermis as part of the dermis and is mainly characterized by the formation of blisters or phlyctenae, as those resulting from scalding or thermal injury resulting from overheated liquid. The third-degree injury endangers the totality of skin layers (epidermis and dermis) and, in many cases, can affect other tissues, as the subcutaneous cellular tissue, muscular tissue and bone tissue. Third-degree burns are considered as the most severe of all thermal injuries, producing deforming injuries. For being deeper, it eliminates the nerve endings responsible for shooting the painful message. These types of burns need transplanting for recomposing destroyed tissues, since the structures and organelles necessary for the natural recovery process, were eliminated. Since burns are wounds that involve the skin, they develop afore mentioned complex process of regeneration and recomposition of injured tissue. The speed or grade of re-epithelization of the affected region is small the greater the area involved is, considerably increasing the recovery time, when the injuries start to cover a body surface over 10% or 15%.

Immediately after the burn trauma, an inflammatory process develops wherein various agents are delivered, occurring deposition of fibrins and platelets activated on the wound surface. A matrix rich in organic material is yielded, able to enclosure bacteria and other strange substances, which frequently aggravates the case, due to sepsis that can follow trauma. During this inflammatory process a great quantity of exudates crop out of the burned region, leading the patient to an intense loss of liquids, which, depending on the burn extension and depth, can cause a severe dehydration case. The inflammatory process extends to adjacent tissues, factor that endangers the functions of these tissues initially intact.

Extensive and deep burns cause alterations that are extended far beyond the affected local, such as anatomic, metabolic, physiological, endocrinology and immune alterations, requiring special care. Significant fluid losses, delivery of inflammatory multi-mediators and contamination by bacteria, occur. When disseminated in central organs through circulation, bacteria and inflammatory mediators can cause cardiac endangerment, failure of gastrointestinal mucous integrity and in extreme cases, multi-organic failure.

Hemodynamic alterations that occur after severe thermal injuries include decrease of cardiac output and reduced volume of circulating plasma, contributing all to a hypovolemic shock. Inflammatory mediators (including cytokines, prostaglandin, nitric oxide and superoxide ions) have been implicated in causing further damage to tissues. It is believed that despite local benefit, such mediators induce undesirable effects when reaching significantly high levels. As an example, a greater damage to tissues can be caused by delivery of proteolitic enzymes and superoxide ions of macrophages and activated leucocytes.

Thus, burns are skin conditions that develop unbalance in a series of natural organic mechanisms, not limited to endangered tissues only, but involve numerous organs that can be affected. Additionally, large thermal injuries induce to a sharp increase in basal metabolic rate. Large nitrogen corporeal losses, observed in burned patients, mainly occur due to protein exudation through burned skin and also by the fact that, under such catabolic stress situation, corporeal proteins can become the metabolic substrate used for production of 15 to 20% of total energy required by the organism. Further to these abnormalities, hormonal levels change with an increase in cathecolamines, cortisol and glucagons, in the presence of normal or slightly increased levels of insulin. These hormonal alterations promote increase of proteolysis and lipolysis. Thus, the entire complex process is characterized by imbalance. The quick recovery of the skin of a burned mammal is of utmost importance for recovery of his normal organic functions. In an embodiment lidocaine is added to the oil mixture and heated during processing until there is a single-phase fluid. Burn victims have an immediate inflammatory response to stop further damage. When an anti-inflammatory oil is applied, blood flow increases and can cause sharp pain as vascular blood pressure expands damaged vesicles. A low level of lidocaine (for example, about 0.8 wt %) is added to the composition of the present disclosure containing collagen or not containing collagen to mitigate the pain and allow blood flow to resume to the damaged area.

Other skin conditions can include dry/chapped skin. In addition, vaginal dryness and erectile dysfunction are also treatable by the present compositions. Without wishing to be bound, these are partially a function of circulation impairment. When the composition is absorbed in these site-sensitive areas, circulation increases by reducing inflammation in the lymph and venous systems. Blood flow increases.

In another embodiment, the compositions are directed to treating Peripheral artery disease (PAD), which is a narrowing of the peripheral arteries to the legs, stomach, arms, and head. After vascular surgery of a subject having peripheral arterial disease (PAD), a topical composition of any of the compositions described herein, can be applied to the area where the surgery took place. For example, if PAD is in the legs, after vascular surgery in the legs, the composition described herein are topically applied to the legs' lower leg skin to increase blood circulation at the skin surface. For example, the composition may be applied as a spray.

Thus, the methods disclosed herein are useful for treating or ameliorating the skin against the effects of environmental conditions. According to an aspect of the present invention, either one or both types of compositions. i.e., composition described herein with or without collagen or is (are) applied topically to at least the part of the body of the patient containing the chapped skin or other skin condition or wound.

Various treatments may be employed. Skin surfaces of the most concern tend to be those not typically covered by clothing such as facial skin surfaces, hand and arm skin surfaces, foot and leg skin surfaces, and neck and chest skin surfaces. In particular, facial skin surfaces, including the forehead, perioral, chin, periorbital, nose, and/or cheek skin surfaces, may be treated with the compositions described herein.

The treatment method may include applying the composition(s) to a previously identified area of skin in need of treatment, or an area where one seeks to prevent, treat or reduce the appearance of chapped skin or other skin disorders. Many regimens exist for the application of the composition(s). The composition(s) may be applied at least once a day, twice a day, or on a more frequent daily basis, during a treatment period, as prescribed by the physician. When applied twice daily, the first and second applications are separated by at least 1 to 12 hours.

Typically, the composition(s) may be applied in the morning and/or in the evening before bed.

The treatment period is ideally of sufficient time to provide an improvement in the appearance of the skin. The treatment period may be at least 1 week, and in some embodiments the treatment period may last about 4 weeks, 8 weeks, or 12 weeks or more. In certain embodiments, the treatment period will extend over multiple months (i.e., 3-12 months) or multiple years. In one embodiment the composition is applied at least once a day during a treatment period of at least 4 weeks, 8 weeks, or 12 weeks. In one embodiment the composition is applied twice a day during a treatment period of at least 4 weeks, 8 weeks, or 12 weeks.

Effective amounts of each of the compositions are applied topically to the area to be treated. The dose varies with the individual and the skin condition. The ideal dose is that dose that provides as much of the compositions as the skin will absorb. An excess amount of the compositions on the surface of the skin can turn rancid. A silky smooth, odorless finish remains on the skin for 24 hours. The dosage regimen for treating skin conditions and/or wounds is selected in accordance with a variety of factors, including the age, weight, sex, and medical condition of the patient, the severity of the condition, pharmacological considerations such as the activity, efficacy, pharmacokinetic and toxicology profiles of the particular composition used.

The doses may be administered in single or divided applications. The doses may be administered once, or application may be repeated. Application may be repeated weekly until skin and/or wound healing is promoted, or a repeat application may be made in the event that healing slows or is stalled. Doses may be applied 1-7 days apart, or more. In the case of a chronic skin condition or wound, repeat applications may be made, for example, one or more times per day, weekly, or bi-weekly, or monthly or in any other frequency for example if and when healing slows or is stalled. For some indications more frequent dosing such as hourly application may be employed.

In an embodiment, any of the compositions alone free of fish collagen may be applied to the wound or skin condition; in another embodiment, the composition comprising fish collagen, as described herein, may be applied to the skin condition or wound or a combination of one or more different compositions not containing collagen, as described herein or a combination of one or more composition comprised of fish collagen described herein, may be applied to the wound or skin condition, or a combination of compositions comprised of collagen, as described herein and a composition not containing collagen as described herein may be applied to the wound or skin condition.

In an embodiment, both types of compositions are applied to the wound or skin condition in a treatment regimen. In an embodiment, the analgesic composition is first applied topically to the area on the skin to be treated in an amount effective to numb the pain emanating from the situs of the wound, burn or skin condition. More specifically, the analgesic composition is applied topically thereto. The excess unabsorbed oil and slough is wiped away. The analgesic composition is allowed to stand on the wound or burn or skin condition until it numbs the breached surface. This usually takes about 15-30 minutes. In addition, it helps dislodge necrotic tissue associated with the skin condition or wound or burn. Without wishing to be bound, it is believed that the solvent action of the MCT helps loosen necrotic tissue. Since this composition is an oil, it is stored in a container where it can be squirted out. The squirting of the composition onto the wound also mechanically dislodges necrotic tissue. The loose necrotic tissue and any unabsorbed composition is wiped out of the wound bed loci or of the skin condition or the burn situs with a sterile gauze or wipe. Optionally, with a scalpel, additional necrotic tissue may be sharply debrided from the bed of the wound or skin condition or situs of the burn. As the wound begins to close and/or the skin condition begins to clear up and the site of the burn begins to heal, the need for sharp debridement is reduced as viable new tissue replaces pre-existing necrotic tissue.

Next, the collagen composition as described herein, is applied to the situs of the wound, skin condition or burn in therapeutically effective amounts to treat the wound, burn or skin condition and effect granulation. The collagen composition encourages granulation. Since this composition is so viscous, the application thereof will be deposited as stripes, i.e., separate spots on the wound or skin condition. However, the body heat softens the collagen containing composition until it flows into the irregularities of the wound bed surface or surface of the skin condition or situs of the burn and conjoins with adjacent stripes to form a contiguous coating of the entire wound bed surface or surface of the loci where the skin condition or burn is located. The collagen composition is covered, such as with gauze or a non-stick bandage or band-aid. Periodically, for example, once a week or sooner, the wound is inspected to see if it is fully granulated. If the wound is not fully granulated, then the old collagen composition is replaced with a new collagen composition and covered again. At the beginning of the treatment, the wound or skin condition is inspected more frequently; as the wound or skin condition starts to heal and granulate, the inspection and replacement of the collagen composition with fresh collagen composition is less frequent. One of ordinary skill in the art, such as a physician can make that determination based upon various factors, such as the severity of the wound, burn or the skin condition, the age of the patient, the health of the patient and the size of the wound, burn or skin condition including the depth thereof and the like. The process of replacing the old collagen composition with new collagen composition is repeated until the situs of wound or skin condition or burn is fully granulated. Once the wound or skin condition or burn is fully granulated, the skin protectant composition, as described herein is applied to the situs of the wound bed surface or surface of the skin condition or burn. The skin protectant composition is topically applied thereto. It covers completely the situs of the wound, burn or skin condition and the intact skin adjacent to the area, such as the periwound, in an amount effective to protect the situs from infection and/or ROS species and/or to retard the growth of pathogens, such as bacteria. In an embodiment, the situs is saturated with a skin protectant composition. Either skin protectant A or B, as defined herein, may be utilized. However, skin protectant A is preferably used when granulation is present. Any excess oil and slough is wiped away. Then, the hydrocolloid composition, as described herein, is applied, to cover the area on which the skin protectant was applied. As described hereinabove, the hydrocolloid composition is a flexible sheet laminated with a plastic film over the sticky side and then inserted into a sealed pouch. After the application of the hydrocolloid composition, the user opens the pouch, peels off the film and places the hydrocolloid composition over the skin protectant composition, which is covering the situs of the wound, burn or skin condition. A therapeutically effective amount of the hydrocolloid composition is applied to the situs. The hydrocolloid composition covers completely the area to which the skin protectant compositon is applied and an area adjacent thereto, such as the periwound, for example, or in another embodiment, the area that borders or is adjacent to and in close proximity to the situs, for example, an area up to 6 inches in diameter around the situs. Periodically, the wound is inspected and, if the skilled medical practioner so determines, the skin protectant composition and the hydrocolloid composition are reapplied as before. Again, the frequency of removing and reapplying the skin protectant composition and the hydrocolloid composition is determined by the physician, and is dependent upon many factors, including the health and age of the patient, the size of the wound or skin condition or burn and the drainage from the wound, skin condition or burn, the sex of the patient, and the like. Thus, this hydrocolloid composition is a sustained release composition or a controlled release composition releasing the oil mixture over a period of time. This hydrocolloid composition absorbs and exudates; as it absorbs and exudates, oil is released. Thus, this hydrocolloid, functions to regulate oil release, regulated by the body's own exudate production. Once the wound has closed, then skin protectant B can be used instead of skin protectant A.

The process of removing the old skin protectant and hydrocolloid composition is repeated until the wound has healed and remodeling is complete. Typically, the hydrocolloid and skin protectant change occurs about once a week. And typically, it takes about two years for the wound to remodel, although the length of time for complete healing and remodeling will vary depending upon various factors, such as the size of the wound, the age and health of the patient, and the like.

Prior to the first step or after the last step, the skin protectant is applied to an area proximate to the skin condition or wound but not on the skin condition or wound. It is placed on a proximate area which is about 2 times the diameter of the size of the wound or skin condition up to about six inches from the skin condition or wound and then over the entire area approximate thereto. For example, if the wound or skin condition or burn is on a limb or finger or toe, then the skin protectant is applied topically over substantially the remainder of the limb, finger, or toe, respectfully. If it is on the shoulder, back or stomach then the skin protectant may be applied topically over substantially the rest of the shoulder, back, or stomach, respectively. The function thereof is to exfoliate old dead and dying skin in the proximate area of the wound or skin condition to bring new, viable skin condition to the surface. Without wishing to be bound, it is believed that as this composition is absorbed, the anti-inflammatory omega-3 oils help reduce inflammation in the vascular system. The vascular system, particularly the microcapillaries, relaxes to allow greater blood flow throughout the skin. The increased blood flow helps heal the wound more rapidly.

As described hereinabove, the weight ratio of the weight of MCT to the weight of the unsaturated triglycerides for some compositions, such as the hydrocolloid composition or the skin protectant A and B is greater than 0.8, while in other compositions, such as the collagen composition and the analgesic composition, the ratio is less than 0.8. It was found that the 0.8 value is an inflection point. More specifically, it was determined that at ratios <0.8, the product is sticky and has a characteristic fish odor; at ratios >0.8, the oil entered the dermis and is increasingly silky smooth and odor-free.

The manipulation of the ratio is driven by MCT, hemp and Cod Liver Oils. So, if more omega3 is added, it is stinky and sticky; if more MCT is added, it is silky smooth and odor-free.

Omega oils (omega3, omega6 & omega9) are important precursors to body-produced chemicals that impact wound healing and skin health. But when the omegas are increased, the blended oil is offensive in use. Adding MCT ameliorates but does not totally resolve this issue. What the inventors found after extensive testing was the 0.8 ratio criticality.

There are very useful and practical results of identifying the 0.8 criticality. When the ratio is less than 0.8 (e.g. analgesic composition and Collagen composition), there is more omega oil, needed for wound bed granulation (where there is less concern about odor and stickiness). The ideal ratio range of omega6-to-omega3 ranges from about 1.0 to about 3.0, and in another embodiment, from about 1 to about 2.0. The high omega concentration keeps the wound bed moist, further encouraging granulation. Thus, low ratios are helpful for wound bed granulation.

The process is so gentle, depending on drainage, that even daily dressing changes (by the patient) are contemplated. Autolytic debridement occurs naturally.

But once the situs, e.g., wound bed, is filled with new granulation, the wound needs to close. This requires a dry surface of the situs to help draw the periwound or skin together and create contiguous outer skin across the wound surface. To do this, the ratio has to be >0.8 to make the oils penetrate, allow moisture to escape and to keep the site odor-free (patient-indicator of healthy skin).

With respect to the treatment factor, depending on the skin condition new treatment may vary. If the skin appears to have underlying infection, and anhydrous oil with red palm concentrate is excess of 0.12% is used to treat the affected skin. As described herein, the cartenoids partitions partly into the skin and partly concentrates on the surface. Surface cartenoids become pro-oxidants. Reactive oxygen species (ROS) are created that help reduce the pathogen cartenoids, acting like anti-oxidants, quench any ROS that this to enter the skin. Thus, the surface is sanitized and the subsurface tissue is unharmed.

Without wishing to be bound, it is believed that the short chain length (C8/C10 triglyceride) and polyunsaturated oils are rapidly absorbed into the skin. The long chain, omega-3 polyunsaturated fats (PUFA) is enzymatically modified by the body to make compounds useful in normal body functions. The PUFA are also naturally anti-inflammatory compounds. As such they reduce resistance in the intradermal capillaries that drain the dermis. Swelling is reduced and surface circulation increases. [There is a visible blush color on treated skin and an associated temperature rise as blood flow increases.] The C8/10 fats also are rapidly absorbed and are useful in normal metabolism.

Without wishing to be bound, it is believed that the monolaurin is a process aid for helping PUFA be rapidly absorbed into the dermis and thus not get oxidized on the skin surface.

Further, without wishing to be bound, Cetyl esters are a wax that does not get absorbed and is not subject to oxidation. It covers slowly absorbed unsaturated fats (like C18:1) to help prevent their oxidation. There is some C18:0 fat in the cod liver oil. It becomes part of the waxy cover layer.

As an advantage of the compositions comprising red palm concentrate, with its carotenoids, the composition will stain necrotic tissue differently than healthy tissue; this enables the doctor to find the wound or skin condition, and to focus on treatment of only the viable tissue.

Because of the simplicity of the process, the physician can train the patient to execute the process at home.

An embodiment of the present application is directed to a kit comprised of separate containers containing hydrocolloid composition, the collagen composition, the analgesic composition, and the skin protectant compositions, either skin protectant A or skin protectant B or both. In another embodiment, the container comprising each composition is a squeeze container, preferably one which is tapered with the tip being capable of being cut away. The kit is accompanied by instructions on how to treat the wound or skin conditions, as described herein.

The collagen composition can also be used for treating burns. Burns are very painful and are first treated with the analgesic-containing oil as described. After the alleviation of the pain, for example, 15-30 minutes, then the collagen composition is placed topically in the wound bed. The periwound treatment with Skin Protectant A and/or B is postponed for 1-3 treatments. Immediate treatment increases blood flow and induces pain. After a period, as of time determined by the physician, such as when healing has begun, the burn site is treated as any other wound, as described herein.

Without wishing to be bound, it is believed that the collagen matrix collagen composition described herein incorporates the oil with fish collagen that allows collagen administration without adding moisture to the wound. The butter-like texture allows the collagen to flow into the interstices of complex wound cavities.

It is believed that the sea salt has a special role in that it makes wound exudate electrically conductive. Periwound charge is negative; wound bed electrical charge is positive. Opposite charges attract which tends to pull the periwound over the wound bed and close the wound.

It is also believed that the periwound/wound bed interface is fragile because periwound skin is attacked by the enzymes in wound exudate, a root cause of wound expansion. Without wishing to be bound, it is further believed that the fish collagen absorbs wound exudate; the C8/C10 fatty acid lowers the pH to inhibit enzymes such as MMP (matrix metalloprotease protein). The net effect is to adjust the wound exudate to be more conducive to healing.

Without wishing to be bound, it is believed that C12 triglyceride helps control moisture loss. It is also believed that the monolaurin helps control the bacterial burden in the wound bed. The wound should not be sterile, the bioburden should be balanced. Bacteria create the enzymes that help the healing process.

The collagen matrix of the present disclosure is best added as a unit dose, so the practitioner can quantify wound volume over time. It can however be added from a jar, multi-use tube or other bulk dispenser.

Each product can be used independent of the other, but there is a synergy when used together.

The C8/C10 triglyceride increases circulation in the skin independently of all else. This benefit is particularly important after the wound has healed as blood flow into and out of the lower extremity helps prevent future skin breakdowns.

The collagen matrix is a rich source of collagen in the wound that helps rebuild skin structure in well-known ways. Applying it as a whipped-butter-like anhydrous product increases the mass of collagen that can be filled into the wound volume.

The synergy comes when all four compositions: analgesic composition, collagen composition skin protectant, composition and hydrocolloid composition products are used as a system. The collagen helps provide structure in the wound bed and situs of the burn or skin condition. The sum of all the oils increases blood flow to the lower extremities, the periwound and the situs of the burn, skin condition and wound bed. The C8/C10 fatty acids, carotenoids and monolaurin help control pathogen populations while still retaining the bacterial activity needed to produce beneficial autolytic enzymes. The sea salt continuously allows opposite charged surface skin to migrate towards the wound bed and accelerate wound closing.

Packaging also can affect the odor of cod liver oil mixtures. A package has to be oxygen free inside the container and not allow oxygen to migrate through the container.

An aerosol can is a particularly valuable container because the propellant atomizes the oil into very small droplets that can be spread over the skin without pooling of oil. This helps accelerate absorption into the skin to further limit the omega3 fats' exposure to oxygen.

The compositions of the present disclosure, whether containing collagen or not, can also be used as a carrier for other drugs besides analgesics, as long as the drug is oil soluble or lipophilic. The term "lipophilic" as used herein implies that the drug is entirely being purely lipophilic or has both a hydrophilic and lipophilic character, but more lipophilic character than hydrophilic character. The term lipophilic therefore encompasses solubilities which range from exclusive solubility in non-polar, water-immiscible organic solvents, to complexes having solubility both in these solvents and non-aqueous water immiscible solvents. The gradation of lipophilicity of the compositions of the present invention can be established by reference to partition coefficients using n-octanol/water, or n-octanol/buffer, or n-octanol/saline (King and Blau, J. Nucl. Med., 21, 147-152 (1980); Oldendorf, ibid, 19, 1182 (1978) and Proc. Soc. Exp. Biol. Med., 147, 813-816 (1974)). In general, those drugs having n-octanol/saline partition coefficients greater than about 10 and especially 100 are useful drugs for which the for the present compositions, whether containing fish collagen or not, can be carriers. Besides lidocaine, other drugs include benzethonium chloride, methylbenzethonium chloride and benzalkonium chloride. What is key is that the API (Active Pharmaceutical Agent) is lipophilic. Non-inclusive examples include lipophilic salts such as Amphotericin B and itraconazole. What is key is that the oil system herein is a mixture of formulation components that can alter the stratum corneum to improve transdermal penetration.

The following non-limiting examples further illustrate the invention.

Example 1

In Example 1, the various components listed below, including triglycerides and beeswax, except the sea salt and the fish collagen are mixed thoroughly with other triglycerides and free fatty acids at 60° C. to form an oil melt, which is a homogenous mixture. Then, the sea salt and fish collagen are mixed together once the oil melt is formed and homogenous. There is 44% fish collagen and 42.5% oil.

The Table below lists each ingredient with the weight percent of various chain lengths and then calculates the weighted average of each triglyceride chain length.

| Example 1 | weight % | | cod liver | super olein | C8/10 | coconut | palm oil | hemp | weighted sum |
|---|---|---|---|---|---|---|---|---|---|
| red palm super olein | 8.4% | C6:0 | | | 0 | | | | 0.00 |
| palm oil | | C8:0 | | 0.034 | 59.7 | 7.3 | | | 6.57 |
| C8/10 fat (MCT) | 11.0% | C10:0 | | 0 | 40.1 | 5.8 | | | 4.41 |
| crude coconut oil | | C12:0 | | 0.173 | 0.1 | 49.1 | 0.2 | | 0.03 |
| C8/10 FFA | 1.0% | C14:0 | 3.6 | 0.961 | | 19.4 | 1.1 | 0.04 | 0.50 |
| hemp oil | 11.5% | C15:0 | | | | | | | 0.00 |
| cod liver oil | 11.5% | C16:0 | 10.4 | 42.465 | | 8.7 | 44 | 16.5 | 6.66 |
| | | C17:0 | | | | | | | 0.00 |
| triethyl citrate | 2.0% | C18:0 | 2.6 | 0.395 | | 2.6 | 4.5 | 2.5 | 0.62 |
| ethyl linoleate | 2.0% | C20:0 | | | | | 0.4 | 0.65 | 0.07 |
| red palm concentrate | 0.1% | C22:0 | | 0.059 | | | | 0.23 | 0.03 |
| fish collagen | 44.0% | C23:0 | | 0.022 | | | | | 0.00 |
| Sea salt | 1.0% | C24:0 | | 0.067 | | | | 0.1 | 0.02 |
| | | C14.1 | | | | | | | 0.00 |
| Cetyl esters NF | | C16.1 | 6.5 | | | | | 0.13 | 0.76 |
| monolaurin | 4.0% | C17.1 | | | | | | | 0.00 |
| beeswax | 3.5% | C18:1 | 20.6 | 44.616 | | | 39.2 | 14 | 7.73 |
| ascorbyl palmitate | | C20:1 | 11 | | | | | 0.37 | 1.31 |
| | | C22:1 | 8.4 | | | | | 0.15 | 0.98 |
| total | 100.0% | C24:1 | | | | | | | 0.00 |
| | | C18:2 | 1.5 | 10.372 | | 0.7 | 10.1 | 56.5 | 7.54 |
| sum oil | 42.4% | C20:2 | | | | | | 0.05 | 0.01 |
| | | g-18:3 | | | | | | 0.85 | 0.10 |
| | | a-C18:3 | | 0.257 | | | 0.4 | 18 | 2.09 |
| | | C20:3 | | | | | | | 0.00 |
| | | C18:4 | 2.4 | | | | | | 0.28 |
| | | C20:4 | | | | | | | 0.00 |
| | | C20:5 | 9.3 | | | | | | 1.07 |
| | | C22:5 | | | | | | | 0.00 |

-continued

| Example 1 | weight % | | cod liver | super olein | C8/10 | coconut | palm oil | hemp | weighted sum |
|---|---|---|---|---|---|---|---|---|---|
| | | C22:6 | 11.9 | | | | | | 1.37 |
| | | | | | | | Triglyceride/Fish Collagen | | 0.96 |
| | | | | | | | (C8:0 + C10:0 + C12:0)/C18:1 | | 1.42 |
| | | | | | (C8:0 + C10:0 + C12:0)/(sum all monounsaturated triglycerides) | | | | 1.02 |

Separately, various weight ratios can be examined for important relationships.

In Example 1, two important ratios are: (C8:0+C10:0+C12:0)/oleic acid:1=1.42 and weight of MCT/(sum of the weight of all mono unsaturated triglycerides)=1.02.

That is, there are more MCT than monounsaturated compounds and more, specifically, than oleic triglyceride. The ratio of sum triglycerides/fish collagen=0.96.

Example 2

In Example 2, the topical composition was prepared as in Example 1, except that coconut oil replaced palm oil and cetyl esters NF replaced half the monolaurin. The fish collagen and sum oils did not change from Example 1. The results are tabulated hereinbelow.

| Example 2 | weight % | | cod liver | super olein | C8/10 | coconut | palm oil | hemp | weighted sum |
|---|---|---|---|---|---|---|---|---|---|
| red palm super olein | | C6:0 | | | | 0 | | | 0.00 |
| palm oil | | C8:0 | | 0.034 | 59.7 | 7.3 | | | 7.18 |
| C8/10 fat | 11.0% | C10:0 | | 0 | 40.1 | 5.8 | | | 4.90 |
| crude coconut oil | 8.4% | C12:0 | | 0.173 | 0.1 | 49.1 | 0.2 | | 4.14 |
| C8/10 FFA | 1.0% | C14:0 | 3.6 | 0.961 | | 19.4 | 1.1 | 0.04 | 2.05 |
| hemp oil | 11.5% | C15:0 | | | | | | | 0.00 |
| cod liver oil | 11.5% | C16:0 | 10.4 | 42.465 | | 8.7 | 44 | 16.5 | 3.82 |
| | | C17:0 | | | | | | | 0.00 |
| triethyl citrate | 2.0% | C18:0 | 2.6 | 0.395 | | 2.6 | 4.5 | 2.5 | 0.80 |
| ethyl linoleate | 2.0% | C20:0 | | | | | 0.4 | 0.65 | 0.07 |
| red palm concentrate | 0.1% | C22:0 | | 0.059 | | | | 0.23 | 0.03 |
| fish collagen | 44.0% | C23:0 | | 0.022 | | | | | 0.00 |
| Sea salt | 1.0% | C24:0 | | 0.067 | | | | 0.1 | 0.01 |
| | | C14:1 | | | | | | | 0.00 |
| Cetyl esters NF | 2.0% | C16:1 | 6.5 | | | | | 0.13 | 0.76 |
| monolaurin | 2.0% | C17:1 | | | | | | | 0.00 |
| beeswax | 3.5% | C18:1 | 20.6 | 44.616 | | | 39.2 | 14 | 3.98 |
| ascorbyl palmitate | | C20:1 | 11 | | | | | 0.37 | 1.31 |
| | | C22:1 | 8.4 | | | | | 0.15 | 0.98 |
| total | 100.0% | C24:1 | | | | | | | 0.00 |
| | | C18:2 | 1.5 | 10.372 | | 0.7 | 10.1 | 56.5 | 6.73 |
| sum triglyceride | 42.4% | C20:2 | | | | | | 0.05 | 0.01 |
| | | g-18:3 | | | | | | 0.85 | 0.10 |
| | | a-C18:3 | | 0.257 | | | 0.4 | 18 | 2.07 |
| | | C20:3 | | | | | | | 0.00 |
| | | C18:4 | 2.4 | | | | | | 0.28 |
| | | C20:4 | | | | | | | 0.00 |
| | | C20:5 | 9.3 | | | | | | 1.07 |
| | | C22:5 | | | | | | | 0.00 |
| | | C22:6 | 11.9 | | | | | | 1.37 |
| | | | | | | | Triglyceride/Fish Collagen | | 0.96 |
| | | | | | | | (C8:0 + C10:0 + C12:0)/C18:1 | | 4.07 |
| | | | | | (C8:0 + C10:0 + C12:0)/(sum all monounsaturated triglycerides) | | | | 2.31 |

Example 1 has beeswax and monolaurin waxes. These waxes form two eutectics, the upper eutectic temperature is 45.6° C. The lower eutectic temperature (as cloud point) is 32.8° C., a difference of 12.8° C.

The almost 13° C. difference in melting points defines a processing window in which one eutectic is liquid and the other is solid. In this intermediate "window," the paste can be pumped into filling machines and fed into individual-use vials.

If a thickening agent, e.g., beeswax, or its equivalent, is not used as a thickening agent, then there is no window and vial filling is infeasible. What is required is a wax system that has at least two eutectic temperatures separated by >5°.

In Example 2, the same two important ratios are: wt of MCT/oleic acid: =4.07 and sum (C8:0+C10:0+C12:0)/sum (all mono unsaturated triglycerides)=2.31. The ratio of all triglycerides to fish collagen was 0.96.

Replacing red palm super olein with coconut oil increases C12:0 and reduces C18:1. Thus, the change from palm to coconut more than doubles the ratio of MCT to unsaturated triglycerides. This change is important because monounsaturated triglycerides are room temperature liquids and they tend to weep out of oil/collagen anhydrous mixtures. MCT is also a room temperature liquid but it is absorbed by the fish collagen matrix and does not weep out. Thus, the ratio of MCT to monounsaturated triglycerides is greater than 1.0 to prevent weeping out oil during storage and distribution.

In Example 2, there are also two melting point temperatures. The upper melting point temperature, e.g., eutectic temperature is 48.9° C., and the lower melting point temperature is 25° C., a difference of 23.9° C.

The Example 2 window is about double the Example 1 window. This means that it is easier to control the paste temperature from feed tank-to-sealed vial with the Example 2 product. As shown below, the waxes have different melting ranges.

|  | Melting Temperature |
|---|---|
| Beeswax | 62-64° C. |
| Monolaurin | 60-66° C. |
| Cetyl Esters NF | 43-47° C. |
| Ascorbyl Palmitate | 116° C. |

Skilled artisans would anticipate about the same melting point with beeswax and monolaurin and possibly a lower melting point with Cetyl Esters NF.

The addition of Cetyl Esters increased the upper melting point temperature and simultaneously lowered the lower melting point temperature. Ascorbyl Palmitate is a fatty acid ester with a ring structure head. The melting point is considerably higher than linear fatty acid esters.

Example 3

The procedure of Example 1 was repeated, except no fish collagen is added. The procedure is outlined hereinbelow. The monolaurin/cetyl ester mixture is heated and cooled. The lower cloud point was measured as 25° C. To the same mixture, 3.5% beeswax was added, and the upper cloud point was determined. The Cloud Point and eutectic point is not the same thing, but the Cloud Point difference and the eutectic point difference (window size) are relatively the same.

| Example 3 | percent |
|---|---|
| MCT Oil | 11.0% |
| C8 FFA | 1.0% |
| Monolaurin | 2.0% |
| Cetyl Esters | 2.0% |
| Red Palm Concentrate | 0.1% |
| Trietnyl Citrate | 2.0% |
| Ethyl linoleate | 2.0% |
| RBD Palm Oil - CP6 | 8.4% |
| Hemp Oil | 11.5% |
| Liver Oil | 11.5% |
| Heat to 140 F. in hot water bath | |
| record temperature every 30 seconds | |
| note when mix is cloudy | |
| cool to 100 f. | |
| add beeswax | |
| Beeswax | 3.5% |
| Reheat to 160 F. | |
| record temperature every 30 seconds | |
| note when mix is cloudy | |
| cool to 100 F. | |

The upper cloud point was determined to be 49.1° C.

Example 4

The Example 3 recipe was repeated, with and without Cetyl Esters. The upper cloud point was 45.6° C.; the lower cloud point was 33.1° C.

From the results of Examples 3 and 4, the following conclusions are drawn:

Although it is reasonable that a mixture of waxes with different melting ranges in a triglyceride melt would have different cloud points, it is surprising that adding a lower melting point wax would increase the upper melting point e.g., upper eutectic cloud point, and simultaneously lower the lower melting point, e.g., the lower eutectic cloud point. This results affects the process for filling the vials.

1. The Product can be easily maintained at a set point temperature in a filler feed tank just below the upper melting point, e.g., upper eutectic cloud point.
2. The temperature should not be above the upper melting point as the frozen beeswax which is holding oil in the pores becomes liquid and flows out of the collagen during pump shearing.
3. As product is pumped through vial filling machines (1-2 g/vial), narrow, flexible, reciprocating feed hoses cool the product below the lower melting point.
   a. The hoses can be traced and insulated, but machine stops allow the product to either heat or cool too much.
   b. Overheated product will separate in the vials, signaling instability to regulators and users.
   c. Underheated products will not flow easily into the vial and vials will be under-filled.
4. A wider window allows introduction of intermediate temperature product into the feed pump. Unavoidable cooling still occurs, but not so when the product drops below the lower melting point temperature.

Example 5

Example 3 is repeated, except coconut oil replaces palm oil. It is noticed that there is a reduction in weeping and the upper cloud point was 46° C. and lower eutectic temperatures was 35° C.

| Example 5 | Percent |
|---|---|
| MCT Oil | 11.0% |
| C8 FFA | 1.0% |
| Monolaurin | 2.0% |
| Cetyl Esters | 2.0% |
| Red Palm Concentrate | 0.1% |
| Triethyl Citrate | 2.0% |
| Ethyl Linoleate | 2.0% |
| Crude Coconut Oil | 8.4% |
| Hemp Oil | 11.5% |
| Liver Oil | 11.5% |
| Heat mixture to 140° F. in hot water bath | |
| Record Temperature every 30 Seconds | |
| Note when mixture is cloudy | |
| Cool to 100° F. | |
| Add Beeswax | |
| Beeswax | 3.5% |
| Reheat to 160° F. | |
| Record Temperature Every 30 Seconds | |
| Note when mixture is cloudy | |
| Cool to 100° F. | |

Example 6

In Example 6, fish collagen was mixed with individual oil components (50:50 w/w) and then stored for 15 hours @ 48.9° C. to induce weeping. The various oils are depicted below in the table.

| C8/10-to-C > 18 Calculated Ratio | | | | | | | | |
|---|---|---|---|---|---|---|---|---|
| | % | % | % | % | % | % | % | % |
| C8/10 | 6 | 8 | 8 | 6 | 6 | 8 | 5 | 6 |
| Crude Coconut Oil | 12 | 12 | 12 | 12 | 12 | 10 | 12 | 10 |

-continued

| C8/10-to-C > 18 Calculated Ratio | | | | | | | | |
|---|---|---|---|---|---|---|---|---|
| | % | % | % | % | % | % | % | % |
| Hempseed Oil | 8 | 16 | 12 | 12 | 16 | 8 | 8 | 8 |
| Cod Liver Oil | 16 | 8 | 12 | 12 | 8 | 16 | 16 | 16 |
| Ascorbyl Palmitate | 0 | 0 | 0 | 2 | 2 | 0 | 3 | 3 |
| C8-10 to C > 18 Ratio | 1.1 | 2.6 | 1.8 | 1.4 | 2.1 | 1.3 | 1.0 | 1.1 |

The results are depicted below.
Oil Weeping [50:50 w/w with Spray-Dried Fish Collagen]
  C8/10 triglyceride: Gritty texture; spot weeping
  Crude coconut oil: Smooth; no weeping
  RBD palm Oil CP6: Smooth; no Weeping
  Hempseed Oil: Smooth; no weeping
  Cod Liver Oil: Smooth; substantial weeping
As shown, the C8/10 mixture has the texture of "wet sand" and is not pumpable. Without wishing to be bound, it is believed that the collagen absorbs the C8/10 directly and does not store the oil in the pores. Excess oil weeps out, but does not form puddles, but rather "dots" of free oil at the base of the test beaker.

Coconut, palm and hempseed have a smooth, no-grit texture that is easily pumped. There is no weeping. Without wishing to be bound, it is believed that the C12-C18 triglycerides enter into the collagen pores and remain there (in the absence of pump shear). The long chain triglycerides (C14-18) are stored in the collagen pores and are stable (in the absence of pump shear).

Cod liver oil is slightly sticky and oozes free oil that collects as a second phase at the base of the test beaker. It is believed that the 43% of cod liver oil ("CLO") that is very long chain triglycerides (C>18) are not completely absorbed by the collagen and do not readily enter the collagen pores. These long chain compounds are the root cause of weeping and stickiness.

The C8/10 is a "triglyceride solvent". The C8/10 role is to solubilize the very long chain triglycerides and make them flow into the collagen pores. Once in the pores, the C8/10 transfers from the pores directly into the collagen matrix.

Ascorbyl palmitate is a lipid-soluble Vitamin C molecule.

Example 7

Example 7 compared crude coconut oil to RBD Palm Oil CP6 for upper and lower eutectic temperatures using the Example 3 oil formula with monolaurin alone, then reheated with the addition of cetyl esters, then reheated with the addition of white beeswax. There were two formulas, one with RBD palm and a second with Crude Coconut Oil. The oils were both 8.4%.

The oil fraction of the oil/collagen mixture was heated to clarity and then cooled with gentle mixing until the Cloud Point (onset of turbidity) was noted.

| Cloud Point (° C.) | | | |
|---|---|---|---|
| | Coconut Oil | RBD Palm Oil | Difference |
| Monolaurin | 35.8 | | |
| Monolaurin + Cetyl Ester | 35.6 | 33.3 | 2.3 |
| Monolaurin + Cetyl Ester + beeswax | 51.7 | 45.6 | 6.1 |
| Upper Eutectic-lower eutectic | 16.1 31% | 12.3 | |

Crude coconut oil (not the same as RBD coconut oil) increased the upper/lower eutectic temperature 31%. A larger difference enlarges the processing window. Crude coconut oil unexpectedly widened the processing window. The target pumping temperature is 49° C. (~120° F.), above the lower eutectic and below the upper eutectic temperature.

Example 8

Example 8 indirectly measured the time required to fill the collagen pores (10 minutes).

When blended hot oil is gently mixed with ambient fish collagen, the powder melds with the hot oil. The temperature is maintained above the upper eutectic temperature during slow collagen addition to allow low surface tension oil to displace air in the collagen pores. What was discovered is that cooled-viscosity increases with hot mixing time and then is stable with more mixing, indicating that the pores are full. When cool, the wax mixture thickens the oily fluid within the pores. The phenomenon of completely filling the pores, made the cooled as-used product too thick to dispense from 2 ml single-use flexible vials.

The % fish collagen was reduced from Example 1 (from 44% to 40%); but this had the effect of reducing the macro pore volume while increasing the macro oil addition (to keep the material balance in balance). The sum triglycerides/fish collagen was 1.1.

The composition and the procedure are outlined below:

| Collagen Matrix CG | |
|---|---|
| | Weight % |
| Weigh @ ambient Temperature | |
| MCT Oil | 8.0% |
| C8 FFA | 1.0% |
| Monolaurin | 4.0% |
| Cetyl Esters | 2.0% |
| Beeswax | 3.5% |
| Triethyl citrate | 2.0% |
| Ethyl linoleate | 2.0% |
| Crude Coconut Oil | 12.0% |
| Red palm concentrate | 0.50% |
| Hemp oil | 16.0% |
| Cod Liver Oil | 8.0% |
| Heat to T = 160 F. | |
| Add collagen and sea salt @ T >130 F. | |
| Ground Sea Salt | 1.0% |
| Fish Collagen | 40.0% |
| Add ascorbyl palmitate | |
| Ascorbyl palmitate | 0.0% |
| Mix 10 minutes | |
| Pump to filler @ T = 130 F. | |
| Total | 100.0% |
| Sum Triglycerides/fish collagen = 1.1 | |

The results are as follows: The weight ratio of the weight of MCT (C8-10 triglycerides) to the weight of oleic acid (C>18) is 2.6. Oil does not weep out of the matrix after 15 hours @ 48.9° C. The flexible vials can be filled commercially @ 48.9° C. The ambient filled vials can be extruded with gentle pressure from the thumb and forefinger.

If 2% Ascorbyl Palmitate replaces 2% crude coconut oil, the practical results are the same except that Vitamin C is added to the Vitamin A, beta carotene (Vitamin A precursor) and lycopene (from the red palm oil concentrate). The C8-10/C>18 ratio declines slightly but rounds to 2.6.

The results show the following:
1. Low surface tension oil was made to penetrate deep within the spray-dried fish collagen pores.
2. A multi-component wax system was invented to allow complete hot oil penetration, warm high-shear vial-filling and no cold-weeping during distribution.

3. Rancid-fat off odors were prevented.
4. There is no need for special mixing equipment, rather, standard double agitator kettles are adequate for processing.
5. The product can withstand electron beam sterilization, an FDA requirement for wound fillers.

Example 9

The following composition is prepared as indicated:

| Omega Oil BV | | |
|---|---|---|
| | Weight % | lot weight 18 kg |
| MCT Oil | 30.0% | 5.400 |
| C8 FFA | 0.3% | 0.054 |
| RBD Palm Oil | 13.8% | 2.484 |
| Hemp Oil | 27.0% | 4.860 |
| Cod Liver Oil | 27.0% | 4.860 |
| Monolaurin | 0.6% | 0.108 |
| Cetyl esters NF | 1.0% | 0.180 |
| Begin Heating (13 Hz agitator setting) | | |
| Set Point @ "7"; off @ 130 F. | | |
| Mix 15 minutes; take turbidity sample | | |
| Drain into 24 qt SS stock pot | | |
| When cool, add fragrance | | |
| Lavender Oil | 0.1% | 0.018 |
| Lemon oil | 0.2% | 0.036 |
| Empty into 6 gal pail | | |
| Total | 100.0% | 18.0000 kg |

This experiment is repeated, but without cetyl ester. In a single variable experiment with and without cetyl esters (Omega Oil BV), the skin-after-oil-rub-in without cetyl esters had a strong fish odor. The same formula with cetyl esters had no skin odor.

Example 10

The following composition is prepared:

| Collagen Matrix CK | |
|---|---|
| | Weight % |
| Weigh @ ambient Temperature | |
| MCT Oil | 8.0% |
| C8 FFA | 1.5% |
| Monolaurin | 4.0% |
| Cetyl Esters | 2.0% |
| Beeswax | 4.0% |
| Triethyl citrate | 2.0% |
| Ethyl linoleate | 2.0% |
| Crude Coconut Oil | 10.0% |
| Red palm concentrate | 0.10% |
| Hemp oil | 12.0% |
| Cod Liver Oil | 12.0% |
| Turn heat off @ 135° F. | |
| Mix until all lumps disappear; maintain 130° F. | |
| Ground Sea Salt | 1.0% |
| Fish Collagen | 41.4% |
| Total | 100.0% |
| Sum triglycerides/fish collagen = 1.01 | |

Collagen Matrix CK has reduced collagen, increased beeswax, equal hemp and cod liver oil and reduced red palm concentrate versus Collagen Matrix CG. The sum of total triglycerides to fish collagen is 1.01. The slight rebalancing was done to improve stability and reduce high temperature weeping.

What was unexpected was that the 25° C. product, aged overnight, could be whipped into "whipped butter" using a standard whisk and a kitchen mixer. The result made the product more stable and reduced the viscosity to make it more pumpable.

The package was changed to a stick pack, a vertical form-fill-seal wrapped around a continuously extruded cylinder of collagen matrix. The product could be filled easily, stay supple throughout distribution, survive freeze/thaw stress test and then flow into the wound interstices with just thumb/forefinger pressure.

What sets this product apart is a mixture of cod liver oil, hemp oil, and waxes with different melting points such that the oil fraction has an upper eutectic temperature at least 5° C. greater than a lower eutectic temperature. The sum of the weight of triglycerides/to the weight of fish collagen is 1:1. A further distinction is this is an anhydrous drug/device combination product.

The formula is a combination device (fish collagen) and an active drug product (OTC Skin Protectant with cod liver oil between 5% and 13.56%).

The product performs as a facial scrub to exfoliate dead and dying skin and then leave the remaining skin "glowing." That is, the dry collagen and sea salt gently remove dead and dying skin whilst the oils are absorbed into the skin without leaving an objectionable odor behind.

Third party evaluators affirmed the rejuvenation of the skin.

Example 11

Example 11 is an OTC Topical Analgesic with lidocaine as the active ingredient. The composition is a carrier for the active pharmaceutical ingredient. It is a mixture of cod liver oil, hemp oil, MCT, cetyl esters and free fatty acid. It is prepared as follows:

| Lavage Oil BZ | |
|---|---|
| | Weight % |
| MCT Oil | 32.0% |
| C8 FFA | 0.3% |
| Monolaurin | 0.6% |
| Cetyl Esters NF | 1.0% |
| Lidocaine | 0.8% |
| Crude Coconut Oil | 14.64% |
| Red Palm concentrate | 0.26% |
| Hemp Oil | 25.2% |
| Cod Liver Oil | 25.2% |
| Begin Heating (13 Hz agitator setting) | |
| Set Point @ "7"; off @ 130 F. | |
| Mix 15 minutes; take turbidity sample | |
| Drain Into 24 qt SS stock pot | |
| Empty into 6 gal pail | |
| Total | 100.00% |

This formula was tested for bacterial kill in a standardized test in a major university. More significantly, this product was tested on an ex vivo porcine skin wound biofilm model inoculated with *S. aureus* and allowed to mature for four days. Half of the explants were treated with an oil based product once per day for three days. Six explants from each group were collected daily and the total bacterial load was assessed. The results are depicted in FIG. 1.

In FIG. 1, day 0 represents the beginning of the experiment with no treatments given yet. The four day old infection was able to further expand in the untreated skins, while the skins treated with the formulation of Example 11 were decreased by approximately 3 logs. This reduction was maintained throughout the duration of the experiment. The averages represent some treated samples with no detectable bacteria and others with detectable bacteria. The differences seen were found to be statistically significant by Student's t-Test for each treatment day with $p \leq 1.1 \times 10^{-6}$.

A female patient fell from her horse and badly scraped her shoulder. Within two weeks of application of Lavage Oil BZ, the wounds healed without scarring. Healing of a normal healthy person is an expected event. Healing without scarring is unexpected.

A second event occurred when a patient had a severe case of poison ivy. Lavage Oil BZ was used to treat the rash and it resolved in 4 days. 4 days is a short time to heal a poison ivy rash.

A third event occurred with an outbreak of shingles. This was treated daily with Lavage BZ and was resolved in three days.

In a fourth event, a patient with autoimmune disease broke out with an ulcer. After three days treatment with Example 11 oil, the ulcer was resolved.

In a fourth experiment, biofilms are induced in a 96 count test cell and then treated with Lavage BZ and an appropriate control.

The biofilm was reduced by 1.3 logs in four days.

In a fifth experiment a patient tripped and ruptured a hamstring tendon. His entire leg turned purple. After 4 days of Example 11 application to the entire leg, the swelling ceased and the leg was no longer purple.

Example 12

An oil was produced similar to Lavage BZ, but without the active ingredient lidocaine.

The oil is mixed @ 12% (W/W) with traditional, well known hydrocolloid gelling compounds, comprising, for example, pectin or an acid pectin that kept the skin pH @-5.5, the pH of the acid mantle. The procedure was prepared as indicated in the table below.

| Hydrocolloid BX | |
| --- | --- |
| | Weight % |
| MCT Oil | 31.00% |
| C8 FFA | 0.30% |
| Monolaurin | 0.60% |
| Red Palm concentrate | 0.26% |
| Cetyl Esters | 1.00% |
| Crude Coconut Oil | 15.44% |
| Hemp Oil | 25.70% |
| Cod Liver Oil | 25.70% |
| | Begin Heating (13 Hz agitator setting) |
| | Set Point @ "7"; off @ 130 F. |
| | Mix 15 minutes; take turbidity sample |
| | Drain into 24 qt SS stock pot |
| | Empty into 6 gal pail |
| Total | 100.00% |

The composition is mixed with the composition containing hydrocolloid gelling compound obtained from Sarasota Medical Products, Inc. in Sarasota, FL to provide a composition comprised of about 88% hydrocolloid. (hereinafter "hydrocolloid composition"). This hydrocolloid composition was placed over a wound for 7 days. There was no bacterial growth in the hydrocolloid dressing.

The combination of MCT, monolaurin, hemp oil and cod liver oil red palm concentrate, crude coconut oil and acid pectin helped reduce the bioburden in the dressing.

Example 13

Example 10, Collagen Matrix CK was used to treat an infected breast cancer after surgery that ended up as a tunneled wound. The wound was completely resolved in two weeks.

What is unexpected is that the collagen dressing with the inventive oil blend can heal an infected wound.

Example 14

In Example 14, the oil blend was used as a spray for intact skin, with no active drug ingredient. It was prepared as indicated hereinbelow.

| Omega Oil BY | |
| --- | --- |
| | Weight % |
| RBD Palm Oil | 14.0% |
| MCT Oil | 30.0% |
| Hemp Oil | 27.0% |
| Cod Liver Oil | 27.0% |
| C8 FFA | 0.3% |
| Monolaurin | 0.6% |
| Cetyl esters NF | 1.0% |
| | Begin Heating (13 Hz agitator setting) |
| | Set Point @ "7"; off @ 130 F. |
| | Mix 15 minutes; take turbidity sample |
| | Drain into 24 qt SS stock pot |
| | When cool, add fragrance |
| Lavender Oil | 0.02% |
| Lemon oil | 0.08% |
| | Empty into partial drum |
| Total | 100.00% |

Omega Oil BY does not have red palm concentrate. The oil is sprayed as fine droplets from a bag-on-valve spray can onto intact skin.

The oils are absorbed within seconds, the monolaurin and Cetyl Esters form an odor-occlusive film over the skin that prevents off odors from escaping.

The Cetyl Esters leaves a silky-smooth, semi-occlusive finish and prevents oil odor escape.

A 75 year old female kicked a dishwasher door by accident, creating a 3 inch×1 inch purple bruise that did not heal in a month. Treatment with Example 14 oil resolved the bruise in 7 days.

Example 15

Crude coconut oil (not refined, bleached and deodorized coconut oil) was used to replace the palm oil in the oil mixtures. The cod liver oil was reduced to meet the OTC Skin Protectant monograph (5% to 13.56% w/w). The total MCT (e.g. MCT added+MCT fraction of crude coconut oil) and free fatty acid were increased.

The table below lists the ingredients and the procedure for making same:

| Lavage Oil CA-Professional | |
|---|---|
| | Weight % |
| MCT Oil | 30.0% |
| C8 FFA | 0.4% |
| Monolaurin | 0.6% |
| Cetyl Esters NF | 1.0% |
| Lidocaine | 1.0% |
| Ascorbyl Palmitte | 2.0% |
| Crude Coconut Oil | 25.50% |
| Red Palm concentrate | 1.00% |
| Hemp Oil | 25.5% |
| Cod Liver Oil | 13.0% |
| | Begin Heating (13 Hz agitator setting) |
| | Set Point @ "7"; off @ 130 F. |
| | Mix 15 minutes; take turbidity sample |
| | Drain into 24 qt SS stock pot |
| | Empty into 6 gal pail |
| Total | 100.00% |

This composition was tested for bacterial kill in a standardized test in a major university. More significantly, this product was tested on an ex vivo porcine skin wound biofilm model inoculated with *S. aureus* and allowed to mature for four days. Half of the explants were treated with an oil based product once per day for three days. Six explants from each group were collected daily and the total bacterial load was assessed.

The 3 log kill of Example 11 increased to a 4 log kill.

Example 16

The Omega Oil BX is a formula that meets the OTC requirement for a Skin Protectant.

The ingredients of the formulation and the preparation thereof is summarized in the following table:

| Omega Oil BX | |
|---|---|
| | Weight % |
| Crude Coconut Oil | 30.0% |
| MCT Oil | 30.0% |
| Hemp Oil | 25.0% |
| Cod Liver Oil | 13.0% |
| C8 FFA | 0.3% |
| Monolaurin | 0.6% |
| Cetyl esters NF | 1.0% |
| | Begin Heating (13 Hz agitator setting) |
| | Set Point @ "7"; off @ 130 F. |
| | Mix 15 minutes; take turbidity sample |
| | Drain into 24 qt SS stock pot |
| | When cool, add fragrance |
| Lavender Oil | 0.02% |
| Lemon oil | 0.08% |
| | Empty into partial drum |
| Total | 100.00% |

This composition was tested for bacterial kill in a standardized test in a major university. More significantly, this product was tested on an ex vivo porcine skin wound biofilm model inoculated with *S. aureus* and allowed to mature for four days. Half of the explants were treated with an oil based product once per day for three days. Six explants from each group were collected daily and the total bacterial load was assessed.

It also achieved a 2 log bacterial kill in the standardized test. The hemp oil was increased, changing the Omega3 to omega6 ratio. Consumers preferred the odor profile.

Example 17

Another formulation is prepared with the ingredients listed in the table below and prepared as indicated in the table below:

| Collagen Matrix CL-1.3 | |
|---|---|
| | Weight % |
| Weigh @ ambient Temperature | |
| MCT Oil | 8.0% |
| C8 FFA | 1.3% |
| Monolaurin | 4.0% |
| Cetyl Esters | 2.0% |
| Beeswax | 4.0% |
| Triethyl citrate | 2.0% |
| Ethyl linoleate | 2.0% |
| Crude Coconut Oil | 10.0% |
| Ascorbyl Palmitate | 0.5% |
| Red palm concentrate | 0.30% |
| Hemp oil | 12.0% |
| Cod Liver Oil | 12.0% |
| Turn heat off @ 145° F. | |
| Transfer melt into mixer @ T ≥ 160° F. | |
| Add collagen, then sea salt | |
| Fish Collagen | 41.4% |
| Ground Sea Salt | 0.5% |
| Total | 100.0% |
| Total triglycerides/fish collagen= | 1.01 |

Matrix CL-1.3 has 0.5% medium-grind Sea Salt. The salt precipitated from the anhydrous matrix when pumped around corners through commercial piping in a filling machine. The sea salt was then more finely ground. Collagen Matrix CL-1.3 with very finely ground sea salt did not completely pass the 48.9° C./15 hour stress test. In this test, a 1.3 ounce glass jar is placed in a 48.9° C. incubator for 15 hours. The bottom of the jar is inspected for seepage. If there is seepage, the composition failed; if not, the composition passed. The results are that oil seeped out of the Matrix to the bottom of the testing container. In addition, the cod liver oil (@12%) was defined as an OTC Skin Protectant active ingredient by the US FDA. This required additional antioxidants to insure cod liver oil ("CLO") was not oxidized during distribution (to retain its 12% target assay). Ascorbyl palmitate was added and Red palm concentrate (a natural source of Vitamin A precursor and lycopene) was added to increase the antioxidant efficacy during distribution. The sea salt was reduced to 0.5% to balance the formula. The sum triglyceride to fish collagen ratio is 1.01.

Collagen Matrix CL-1.3 had zero oil weeping after the 48.9° C./15 hour thermal stress test. The reduction in salt and the addition of Ascorbyl Palmitate's effect on stability was unexpected and required a sea salt level study be conducted (as Example 18).

Example 18

Experiment 18 consists of three formulations, prepared as indicated below, with the ingredients listed:

| Collagen Matrix CL.6 | Weight % | Collagen Matrix CL.9 | Weight % | Collagen Matrix CL.3 | Weight % |
|---|---|---|---|---|---|
| Weigh @ ambient Temperature | | Weigh @ ambient Temperature | | Weigh @ ambient Temperature | |
| MCT Oil | 8.0% | MCT Oil | 8.0% | MCT Oil | 8.0% |
| C8 FFA | 1.2% | C8 FFA | 0.9% | C8 FFA | 1.5% |
| Monolaurin | 4.0% | Monolaurin | 4.0% | Monolaurin | 4.0% |
| Cetyl Esters | 2.0% | Cetyl Esters | 2.0% | Cetyl Esters | 2.0% |
| Beeswax | 4.0% | Beeswax | 4.0% | Beeswax | 4.0% |
| Triethyl citrate | 2.0% | Triethyl citrate | 2.0% | Triethyl citrate | 2.0% |
| Ethyl linoleate | 2.0% | Ethyl linoleate | 2.0% | Ethyl linoleate | 2.0% |
| Crude Coconut Oil | 10.0% | Crude Coconut Oil | 10.0% | Crude Coconut Oil | 10.0% |
| Ascorbyl Palmitate | 0.5% | Ascorbyl Palmitate | 0.5% | Ascorbyl Palmitate | 0.5% |
| Red palm concentrate | 0.30% | Red palm concentrate | 0.30% | Red palm concentrate | 0.30% |
| Hemp oil | 12.0% | Hemp oil | 12.0% | Hemp oil | 12.0% |
| Cod Liver Oil | 12.0% | Cod Liver Oil | 12.0% | Cod Liver Oil | 12.0% |
| Turn heat off @ 145° F. | | Turn heat off @ 145° F. | | Turn heat off @ 145° F. | |
| Transfer melt into mixer @ T ≥ 160° F. | | Transfer melt into mixer @ T ≥ 160° F. | | Transfer melt into mixer @ T ≥ 160° F. | |
| Add collagen, then sea salt | | Add collagen, then sea salt | | Add collagen, then sea salt | |
| Fish Collagen | 41.4% | Fish Collagen | 41.4% | Fish Collagen | 41.4% |
| Ground Sea Salt | 0.6% | Ground Sea Salt | 0.9% | Ground Sea Salt | 0.3% |
| Total | 100.0% | Total | 100.0% | Total | 100.0% |
| Mix low speed with paddle mixer blade until all limps disappear | | Mix low speed with paddle mixer blade until all limps disappear | | Mix low speed with paddle mixer blade until all limps disappear | |
| Maintain > 120° F. | | Maintain > 120° F. | | Maintain > 120° F. | |
| Refrigerate overnight | | Refrigerate overnight | | Refrigerate overnight | |
| Whip 2 minute (low) and 3 minutes (high) | | Whip 2 minute (low) and 3 minutes (high) | | Whip 2 minute (low) and 3 minutes (high) | |
| Transfer Into Storage Drum | | Transfer Into Storage Drum | | Transfer Into Storage Drum | |

In Example 18, Ascorbyl Palmitate and red palm concentrate were held constant. Sea Salt varied from 0.3% to 0.6% to 0.9%. Caprylic acid was reduced to keep the formula balanced. The process was unchanged: mix/heat liquids until melted; fold in fish collagen and then finely ground sea salt; let cool overnight; mix vigorously for 5 minutes. In the example, one sample is left at ambient temperature for 15 hours; a second sample was exposed to freeze/thaw conditions (refrigerated for 4 hours, then stored at ambient for 15 hours a third sample was exposed to 48.9° C./15 hours. The oil seepage was evaluated.

Surprisingly, the 0.3% sea salt showed weeping and the 0.6% and 0.9% sea salt did not show weeping. This was the opposite of what was expected.

The specific gravity is ~0.8. The viscosity is 25,000 cP.

Example 19

The Example 17 formula was replicated except the 0.5% Ascorbyl Palmitate was eliminated and replaced with +0.5% C8 FFA (total FFA=1.8%).

After completing the 15 hour heat stress test described in Example 17, there was weeping oil on the bottom of the clear test jar. Ascorbyl Palmitate prevented heat related oil weeping.

Example 20

Example 20 took 200 g of the oil/wax mixture of Example 17, but with no Ascorbyl Palmitate and heated it until the melt was clear. The melt was allowed to cool with very gentle mixing (beaker swirl) until the cloud point was observed and recorded. Then the Ascorbyl Palmitate was incrementally added (+0.1% per increment) and the melt point after each add was determined. The 0% Ascorbyl Palmitate cloud point was 64.4° C.

Figure 2:
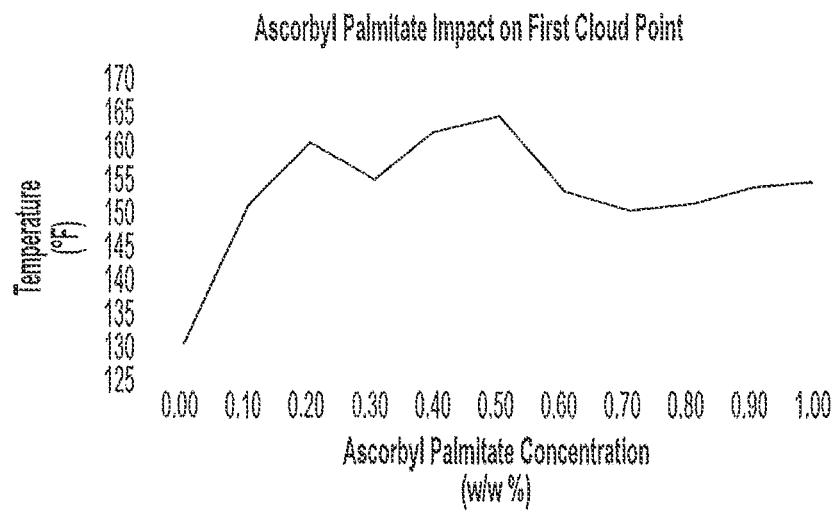
FIG. 2 is a graphical depiction of the effect of the addition of Ascorbyl palmitate on the cloud point of the formulation of Example 20.

FIG. 2 depicts the increase in the cloud point as a function of the concentration of the Ascorbyl Palmitate. As shown in FIG. 2, the cloud point increased immediately when Ascorbyl Palmitate was added. At 0.5%, the cloud point reached a maximum (73.3° C.). Thereafter, the cloud point dropped to an average of 66.8° C. with increasing Ascorbyl Palmitate.

When Ascorbyl Palmitate gels, it is denser than the liquid oil and sinks.

As shown by the data in Examples 17-20, the mixture of Ascorbyl Palmitate with the oils of Example 17 lowers the melting point of Ascorbyl Palmitate. But Ascorbyl Palmitate precipitates as a gel before the beeswax eutectic is reached; Ascorbyl Palmitate precipitates, coating the outside of the porous, solid fish collagen. The Ascorbyl palmitate cloud point is not a eutectic point, because it forms a gel with the oil mixture and is not a waxy eutectic point solid as with beeswax, monolaurin and cetyl ester.

Without wishing to be bound, it is believed that, the low surface tension of the oil mixture allows the molten fraction to enter the pores and displace the gas in the pores. Hot MCT transfers from the pores to the body of the fish collagen before the first eutectic is reached. When cooled below the first and second eutectic, the waxes freeze in the pores, blocking molten oil from seeping out.

When the Example 17 collagen matrix is fully cooled to ~27° C. the mixtures hardens. When vigorously mixed in an inert gas environment, the temperature rises and the specific gravity declines to ~0.8. The cooled, whipped mixture is an easily pumped, easily extruded paste.

There was no oil weeping at temperatures greater than the second eutectic temperature. In addition, it was found that less salt made the formulation unstable and more salt made it stable.

Without wishing to be bound, it is believed that the first precipitation of a ring fatty ester (Ascorbyl Palmitate) is sterically hindered and thus occurs on the outside of the porous collagen.

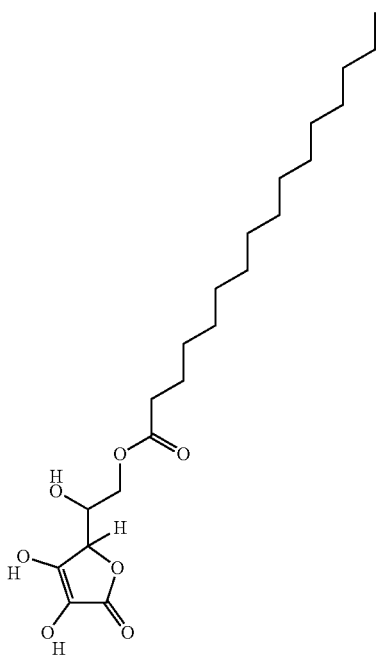

Then the subsequent precipitation of linear fatty esters (beeswax, monolaurin, Cetyl Esters NF) are NOT sterically hindered and enter the pores of the spray dried fish collagen. Beeswax

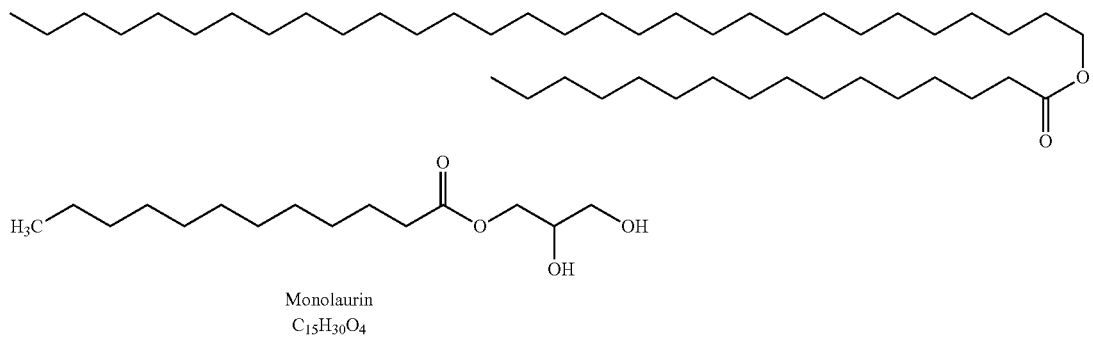

Monolaurin
$C_{15}H_{30}O_4$

An example of Cetyl esters is below.

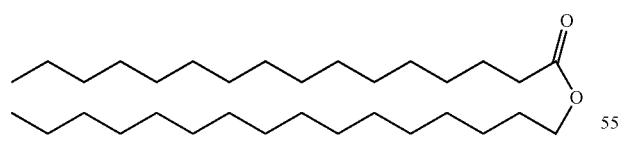

Finally, when the cooled mixture is vigorously mixed, the coated outsides of all the fish collagen spheres come into contact with each other such that, after cooling, there is agglomeration from the sticky external Ascorbyl Palmitate that holds entrained inert gas in the granule-to-granule interstices and keeps weeping oil trapped within the fish collagen pores.

Figure 3:
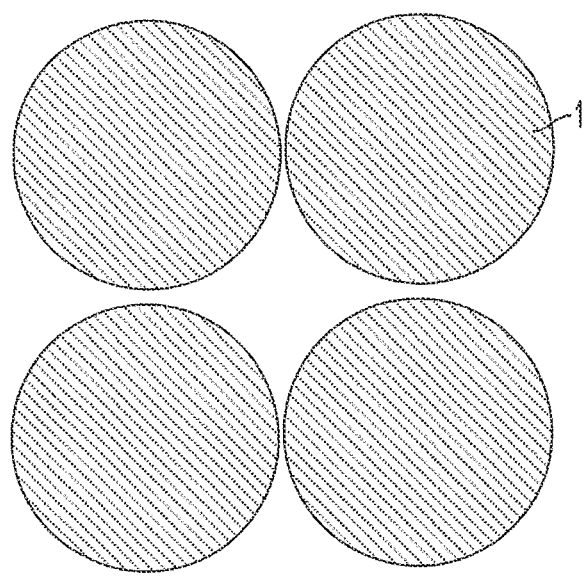
FIGS. 3-7 depict schematically the effect on salt and oil seepage.
Figure 4:
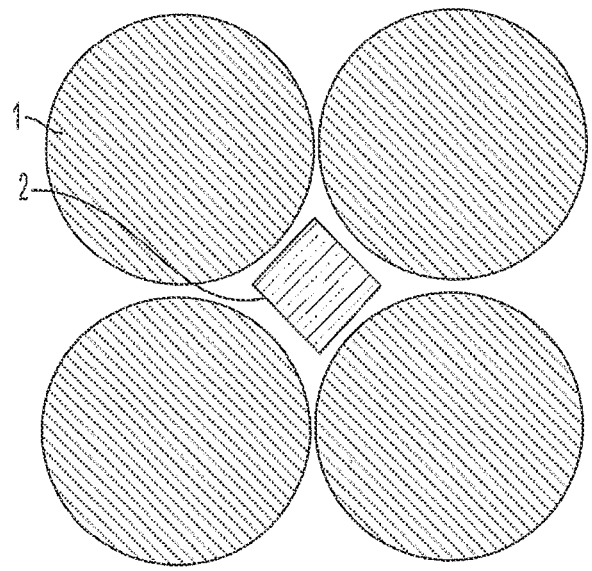
Figure 5:
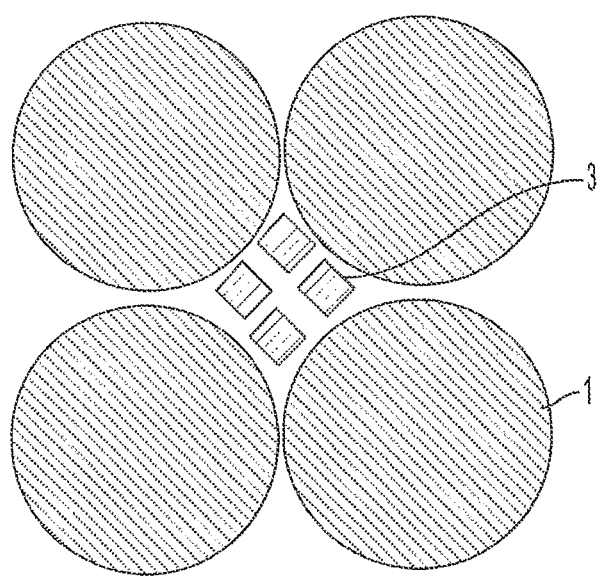
Figure 6:
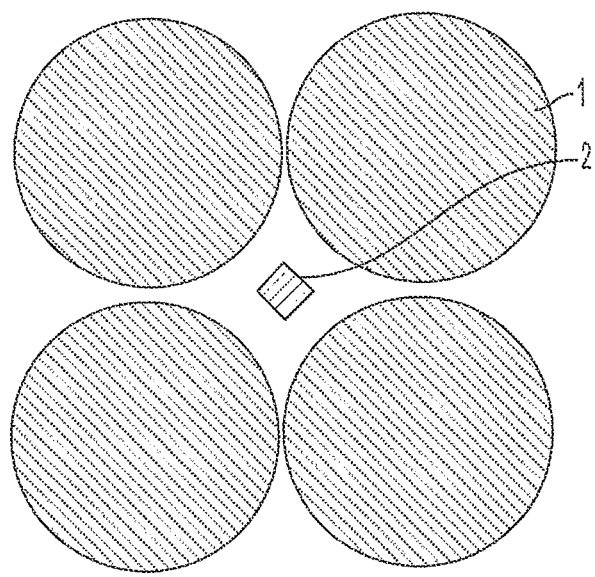
Figure 7:
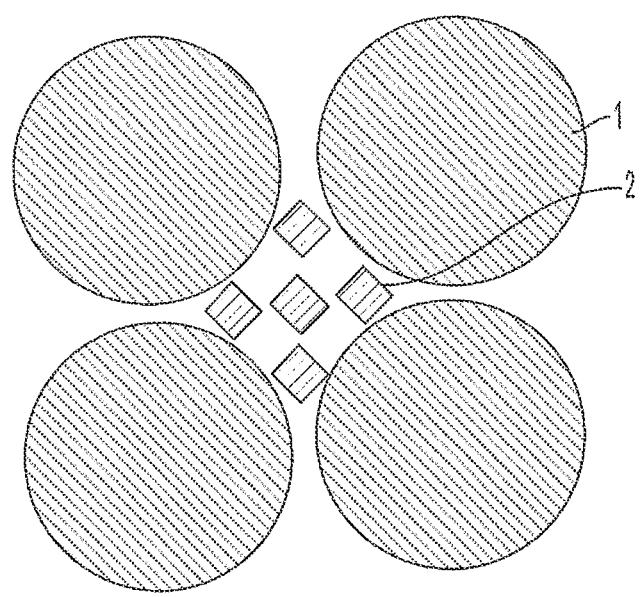

Without wishing to be bound, it is believed that the sea salt effect is explained as follows. The collagen (1) is spherical. When stacked in an oil base, there are large interstices between spheres, as depicted in FIG. 3. When coarse cubic salt crystals (2) are added, the interstices are expanded, creating pathways for leakage, as shown in FIG. 4. When the salt is finally ground (3), the interstices are not stretched and are attached to the surface of the collagen spheres by surface-precipitated Ascorbyl Palmitate. This fills the void interstices and impedes seepage, as shown in FIG. 5. When the salt (2) level is low, the interstices are not filled and there is seepage, as shown in FIG. 6. If the salt (2) level is too high, then the spheres are stretched apart and there is leakage, as shown in FIG. 7.

Sea salt affects seepage stability mechanically. The ideal particle size and weight % are interactive and unobvious.

Example 21

A formulation is prepared as indicated hereinbelow:

| | Collagen Matrix CM Weight % |
|---|---|
| Weigh @ ambient Temperature | |
| MCT Oil | 8.0% |
| C8 FFA | 1.0% |
| Monolaurin | 4.0% |
| Cetyl Esters | 2.0% |
| Beeswax | 4.0% |
| Triethyl citrate | 2.0% |
| Ethyl linoleate | 2.0% |
| Crude Coconut Oil | 10.0% |
| Ascorbyl Palmitate | 0.5% |

-continued

| | Collagen Matrix CM Weight % |
|---|---|
| Red palm concentrate | 0.20% |
| Hemp oil | 12.0% |
| Cod Liver Oil | 12.0% |
| Turn heat off @ 160° F. | |
| Transfer melt into mixer @ T ≥ 160° F. | |
| Add collagen, then sea salt | |
| Fish Collagen | 41.4% |
| Ground Sea Salt | 0.9% |
| Total | 100.0% |
| sum of the weight of triglyceride/fish collagen= | 1.01 |
| Mix low speed with paddle mixer blade until all lumps disappear | |
| Maintain > 120° F. | |
| Cool overnight | |

-continued

| Collagen Matrix CM | |
|---|---|
| | Weight % |
| Whip 2 minute (low) and 3 minutes (high) Transfer into Storage Drum Fill into vials | |

The following changes were made to the formulation:
The red palm oil was reduced from 0.3 to 0.2%.
The ground sea salt was increased from 0.5% to 0.9%.
The C8 FFA was reduced from 1.3% to 1.0%.
The red palm concentrate was reduced to change the matrix color from apricot to canary yellow.
The sea salt was adjusted to match the isotonic salt level in the human body.
The C8 FFA was reduced to balance the formula. The weight of total triglycerides/wt of fish collagen ratio is 1.01.
The Ascorbyl Palmitate and red palm concentrate (primarily beta carotene and lycopene) together represent a mixture of antioxidants designed to help protect the poly-unsaturated fatty acids (PUFA), particularly the PUFA in the over the counter ("OTC") active ingredient cod liver oil. The C8 FFA will help keep the wound bed pH slightly acidic. The ground sea salt will help maintain the isotonic nature of the wound bed.
Finely ground sea salt improves the seepage stability during high temperature excursions during distribution.

Example 22

The Example 22 oil mixture is designed to temporarily protect and temporarily relieve pain in minor cuts, scrapes and burns. Example 22 uses crude coconut oil. Lidocaine and C8 free fatty acids are optional ingredients. The freeze/thaw turbidity of Example 22=0.2 NTU. A lidocaine concentration @ 1.0% with a corresponding MCT decrease has a turbidity=0.5 NTU.

| Lavage Oil CA-Professional | |
|---|---|
| | Weight % |
| MCT Oil | 30.0% |
| C8 FFA | 0.4% |
| Monolaurin | 0.6% |
| Cetyl Esters NF | 1.0% |
| Lidocaine | 1.0% |
| Ascorbyl Palmitte | 2.0% |
| Crude Coconut Oil | 25.50% |
| Red Palm concentrate | 1.00% |
| Hemp Oil | 25.5% |
| Cod Liver Oil | 13.0% |
| Begin Heating (13 Hz agitator setting) Set Point @ "7"; off @ 130 F. Mix 15 minutes; take turbidity sample Drain into 24 qt SS stock pot Empty into 6 gal pail | |
| Total | 100.00% |

The Example 22 oil is expressed from a 4 ml oxygen barrier vial such that oil velocity and MCT solvent action help dislodge necrotic tissue and biofilm from the open wound. The oil mixture helps transport oils and any active ingredients into the wound bed.
After a short wait, necrotic tissue and slough is wiped from the wound bed using 4×4 gauze. Lidocaine will temporarily relieve the pain of mechanical slough removal.

The wound bed absorbs MCT and absorbed components but rejects long chain fats. The longchain fats coat the granule bed with a semi-occlusive film, helping moderate water loss.
Since the oil mixture is anhydrous, C8 free fatty acid (FFA) is protonated. Bacterial cells will allow the FFA to penetrate through the lipid bilayer. Once inside the aqueous portion of the cell, the FFA will partition and help lower cell pH. Cell growth is inhibited.

Example 23

Example 23 is an oil mixture designed to be a 12% component of a hydrocolloid, replacing mineral oil in the hydrocolloid. The oil is slow-released to the wound bed surface over 7 days.

| Hydrocolloid BX | |
|---|---|
| | Weight % |
| MCT Oil | 31.00% |
| C8 FFA | 0.30% |
| Monolaurin | 0.60% |
| Red Palm concentrate | 0.26% |
| Cetyl Esters | 1.00% |
| Crude Coconut Oil | 15.44% |
| Hemp Oil | 25.70% |
| Cod Liver Oil | 25.70% |
| Begin Heating (13 Hz agitator setting) Set Point @ "7"; off @ 130 F. Mix 15 minutes; take turbidity sample Drain into 24 qt SS stock pot Empty into 6 gal pail | |
| Total | 100.00% |

The oil mixture is added to a standard (skin pH=7) CMC/pectin hydrocolloid @12% w/w, replacing mineral oil. The pectin is an optional ingredient with a pH≤the pH of the acid mantle. Acidic pectin and alkaline CMC (carboxymethyl cellulose) create a buffer with absorbed exudate @ pH=5.5±1.0.
Virgin palm oil is used to coat the periwound to help prevent periwound maceration.

Example 24

Example 24 adds an optional foam layer between the hydrocolloid skin contact layer and the foam. The addition of a hydrophilic foam backing allows highly exudating wounds to be treated with a hydrocolloid.
The stability issues of the single-phase oils are straight-forward to someone skilled in the art. When fish collagen is added to the oils, the solution is considerably more complex and not obvious. There are three conflicting technical objectives:
Seepage Control
Ascorbyl palmitate is added to glue the collagen spheres tightly together to fix the cross-sectional area of all seepage pathways.
Sea Salt is ground to plug the interstices and minimize the remaining cross-sectional area of all seepage pathways.
Flowability
Nitrogen gas is whipped into the stiff, ambient temperature matrix to form flexible encapsulated gas bubbles that can flex when pumped or extruded.
Different waxes are added to create dual melting points separated by at least 5° C. such that both melting points are frozen during product distribution, but the lower melting points melts when spread onto the "hot" wound bed.

Efficacy

Fish collagen >40% helps to build structure in the wound bed.

Cod Liver Oil between 5% and 13.56% temporarily protects the raw skin of the wound bed.

The technical task is analogous to finding the "sweet spot" where three non-concentric circles overlap, and then enlarging said sweet spot until the sweet spot is large enough to be operated within commercially.

Example 25

The following composition is prepared as follows.

| | Collagen Matrix CP Weight % |
|---|---|
| Weigh @ ambient Temperature | |
| MCT Oil | 7.4% |
| C8 FFA | 1.6% |
| Monolaurin | 4.0% |
| Cetyl Esters | 2.0% |
| Beeswax | 4.0% |
| Triethyl citrate | 2.0% |
| Ethyl linoleate | 2.0% |
| Crude Coconut Oil | 10.0% |
| Ascorbyl Palmitate | 0.5% |
| Red palm concentrate | 0.20% |
| Hemp oil | 12.0% |
| Cod Liver Oil | 12.0% |
| Turn heat off @ 160° F. | |
| Add collagen with gentle mixing | |
| Fish Collagen | 41.4% |
| Pour into 8 × 4 liter containers | |
| Cool overnight | |
| Transfer to whipping bowl | |
| Calculate net weight and add sea salt | |
| Ground Sea Salt | 0.9% |
| Total | 100.0% |
| Blend 2 minute (low) and whip 3 minutes (high) | |
| Transfer into 25 liter SS Storage Drum | |
| Fill into vials | |
| Triglyceride/fish collagen= | 1.0000 |

The results are as follows: There was considerable seepage in the 120° F. stress test.

Example 26

The following example is prepared with the following composition:

| Collagen Matrix CR | |
|---|---|
| | Weight % |
| Weigh @ ambient Temperature | |
| MCT Oil | 8.00% |
| C8 FFA | 1.30% |
| Monolaurin | 4.30% |
| Cetyl Esters | 2.00% |
| Beeswax | 4.00% |
| Triethyl citrate | 2.00% |
| Ethyl linoleate | 2.00% |
| Crude Coconut Oil | 10.00% |
| Ascorbyl Palmitate | 0.50% |

-continued

| Collagen Matrix CR | |
|---|---|
| | Weight % |
| Red palm concentrate | 0.20% |
| Hemp oil | 12.00% |
| Cod Liver Oil | 11.40% |
| Turn heat off @ 160° F. | |
| Add collagen with gentle mixing | |
| Fish Collagen | 41.40% |
| Pour into 8 × 4 liter containers | |
| Cool overnight | |
| Transfer to whipping bowl | |
| Calculate net weight and add sea salt | |
| Ground Sea Salt | 0.90% |
| Total | 100.00% |
| Blend 2 minute (low) and whip 3 minutes (high) | |
| Transfer into 25 liter SS Storage Drum | |
| Fill into vials | |
| Triglyceride/fish collagen= | 1.0000 |

The results of this experiment are:
Viscosity was 65,000 cP
There was no seepage in the 120° F. stress test.
There is no odor on the skin.
MCT oil increased to 8%
The product is a flowable paste.
Red Palm Concentrate is greater than 0.12% w/w
The product has 4 distinct eutectic temperatures"
122°—Ascorbyl Palmitate freezes
112° F.—Beeswax freezes
98.5° F.—monolaurin/Cetyl Esters NF freeze
about 75° F.—coconut oil freezes The adjustment of the CLO, C8 FFA and monolaurin, as indicated in this example, resulted in the third eutectic temperature to drop from just above human body temperature (98.6° F.) to just below. This small change is trivial in terms of product stability, but critical in product functionality.

At higher temperatures, the Matrix does not flow into the wound bed irregularities.

At a temperature just below body temperature, the Matrix softens and comes into intimate contact with all wound bed surfaces.

This molding to the wound surfaces is in distinct contrast to skin substitutes that are applied as physical sheets and do not touch all surfaces when applied.

Figure 8:
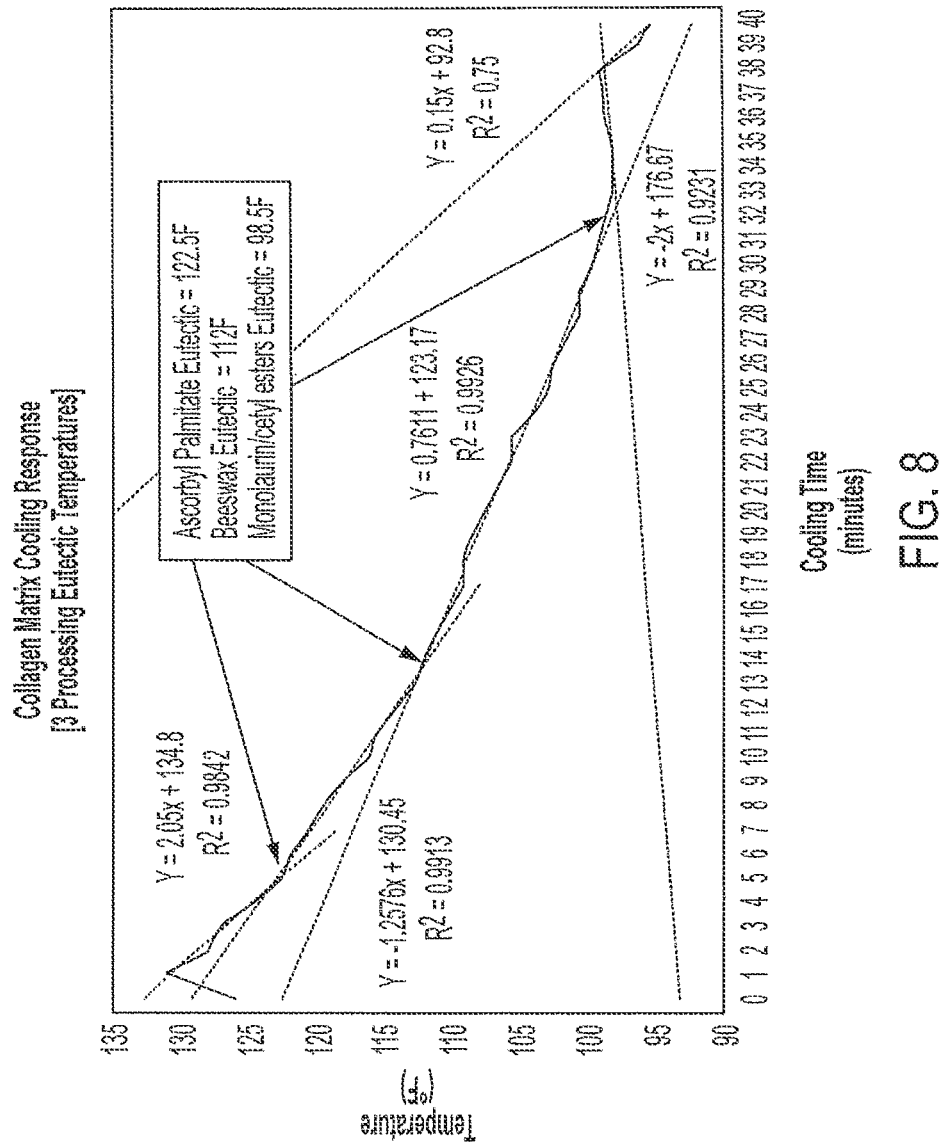
FIG. 8 is a graph of the cooling response of the pharmaceutical composition comprised of collagen of Example 26, showing three of the four eutectic temperatures of the composition.

FIG. 8 illustrates the collagen Matrix Cooling Response and shows three of the four eutectic temperatures. This graph was obtained by methods known in the art to the skilled artisan:

The composition is mixed at a temperature sufficient to melt the wax ester ingredients (Ascorbyl palmitate, beeswax, monolaurin & Cetyl Esters NF). The mixture is gently stirred at a constant rate while the surface temperature is measured every minute. A run chart of temperature versus cooling time is plotted. Zones of linear cooling rate are identified by fitting best-fit lines (maximum $R^2$). The eutectic temperature is where two best-fit lines intersect (as shown in the chart).

The fourth eutectic temperature (coconut oil) is difficult to measure because its freezing point is approximately that of laboratory temperature and it takes several days to congeal. Nevertheless the change in viscosity after freezing is obvious.

The differences with Example 24 are:

MCT oil increased to 8%

FFA reduced to 1.3%

Monolaurin increased to 4.3%

CLO reduced to 11.4%

The triglyceride/fish collagen ration is 1.000

These apparently very small differences are critical:

Filling temperature is increased to 100° F.

Slightly higher reduces viscosity, but @ 110 F, the gas comes out of the whipped matrix and viscosity jumps to >500,000 cP ("hard cheese")

CLO reduced to reduce high-seepage triglyceride

MCT increased to increase oil absorbed directly by fish collagen

FFA increased to lower viscosity

Wax increased to plug pores.

Triglyceride/fish collagen ratio optimized @ 1.000

The collagen composition with its various eutectic temperatures stabilize the Collagen Matrix to make it shelf stable and help its functionality. Without wishing to be bound, the melt is infused into the collagen pores. Ascorbyl palmitate (0.5%) freezes, partially locking melt into each pore. Beeswax (4%) freezes, further locking in melt plus covering each collagen granule with wax. Monolaurin and Cetyl Esters NF (6.3%) freeze. The collagen pores are sealed; the pores are expanded by the enlarged crystals. Each pore is swelled (more spherical shaped). Liquid oils are physically trapped inside the pores by the frozen waxes. As a result, liquid oils cannot ooze out and collect at the base of the container. The oozing out of the liquid oils is a pronounced defect in the prior art. Finally, coconut oil (10%) freezes, effectively tying each spherical, fat-infused collagen particle into a flowable paste.

Example 27

The following composition comprised of hydrocolloid is prepared as follows:

| Component | Weight % |
| --- | --- |
| MCT Oil | 4.8 |
| Crude Coconut Oil | 4.8 |
| Hemp Oil | 1.2 |
| Cod Liver Oil | 1.2 |
| Carboxymethylcellulose | 50.0 |
| Other components such as process aids, tackifiers, water | 38 |

The above components are placed into a 13 HZ agitator with heater at ambient temperature. The mixture is heated with stirring to 130° F. When the temperature reaches 130° F., the sample is mixed for another 15 minutes. The turbidity is measured. The liquid from the resulting mixture was drained into a 24 quart stock pot, and collected into q 6 gallon pail.

The weight ratio of MCT/Sum of unsaturated triglycerides is 2.0; the weight ratio of omega 6 fatty acid to omega 3 fatty acid is 1.51.

Example 28

The following composition comprised of the following compounds was prepared:

| Chemical | Weight % |
| --- | --- |
| MCT Oil | 32 |
| C8 FFA | 0.3 |
| Monolaurin | 0.6 |
| Cetyl Ester | 1.0 |
| Lidocaine | 0.8 |
| RBD Palm Oil | 14.6 |
| Hemp Oil | 25.2 |
| Cod Liver Oil | 25.2 |

The above compounds were placed into a 13 HZ agitator with heater at ambient temperature. The mixture was heated with stirring to 130° F. When the temperature reached 130° F., the sample was mixed for another 15 minutes. The turbidity was measured. The liquid from the resulting mixture was drained into a 24 quart stock pot, and collected into a 6 gallon pail.

The weight ratio of MCT/Sum of unsaturated triglycerides is 0.66 the weight ratio of omega 6 fatty acid to omega 3 fatty acid is 1.6.

For breached skin the MCT/Sum of unsaturated triglycerides is between 0.5 and 0.75 because odor and slow migration into the skin of omega3 and omega6 is a benefit to healing open wounds.

Example 29

The following composition comprised of the following compounds was prepared:

| Chemical | Weight % |
| --- | --- |
| MCT Oil | 40 |
| C8 FFA | 0.3 |
| RBD Palm Oil | 18 |
| Crude coconut oil | 20 |
| Hemp Oil | 10 |
| Cod Liver Oil | 10 |
| Monolaurin | 0.6 |
| Cetyl Ester | 1.0 |
| Lavender Oil | 0.02 |
| Lemon Oil | 0.08 |

The above compounds were placed into a 13 HZ agitator with heater at ambient temperature. The mixture was heated with stirring to 130° F. When the temperature reached 130° F., the sample was mixed for another 15 minutes. The turbidity was measured. The liquid from the resulting mixture was drained into a 24 quart stock pot and allowed to cool. When the mixture was cooled to run temperature, the fragrance of lavender oil and lemon oil were added and mixed. After the composition is homogenous, the mixture was collected into a 6 gallon pail.

The weight ratio of MCT/Sum of unsaturated triglycerides is 1.1 the weight ratio of omega 6 fatty acid to omega 3 fatty acid is 1.5.

Example 30

The following composition comprised of the following compounds was prepared:

| Chemical | Weight % |
| --- | --- |
| MCT Oil | 40 |
| C8 FFA | 0.3 |
| Red Palm Concentrate | 0.10 |
| RBD Palm Oil | 20 |
| Crude coconut oil | 18 |
| Hemp Oil | 10 |
| Cod Liver Oil | 10 |
| Monolaurin | 0.6 |
| Cetyl Ester | 1.0 |

The above compounds were placed into a 13 HZ agitator with heater at ambient temperature. The mixture was heated with stirring to 130° F. When the temperature reached 130° F., the sample was mixed for another 15 minutes. The turbidity was measured. The liquid from the resulting mixture was drained into a 24 quart stock pot, and collected into a 6 gallon pail.

The weight ratio of MCT/Sum of unsaturated triglycerides is 1.0 the weight ratio of omega 6 fatty acid to omega 3 fatty acid is 1.9.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:

1. An anhydrous topical composition comprising an omega fatty acid product, the omega fatty acid product comprising:
   about 5% to about 30% cod liver oil by weight;
   about 5% to about 30% hempseed oil by weight;
   about 0.5% to about 1.5% analgesic by weight;
   0.3% to 1.6% C8 free fatty acid (FFA) by weight;
   wherein the cod liver oil, the hempseed oil, or both comprise a weight ratio of omega-6 fatty acid to omega-3 fatty acid of at least 1.0 to at most 3.0; and
   wherein the omega fatty acid product further comprises a nonoxidizing semi-occlusive film, whereby after being disposed about at least one portion of a skin condition, a surrounding periwound, or both, and wherein a protonation of the C8 FFA causes inhibition of bacterial cell growth.

2. The anhydrous topical composition of claim 1, wherein the omega fatty acid product additionally comprises red palm concentrate.

3. The anhydrous topical composition of claim 1, wherein the omega fatty acid product is anti-inflammatory.

4. The anhydrous topical composition of claim 3, wherein the omega fatty acid product is configured to reduce resistance to blood drainage in the wound, thereby increasing blood flow to the wound.

5. The anhydrous topical composition of claim 4, wherein the omega fatty acid product is configured to reduce swelling.

6. The anhydrous topical composition of claim 1, wherein the omega fatty acid product inhibits pain when applied to the wound.

7. The anhydrous topical composition of claim 6, wherein the omega fatty acid product is configured to inhibit pain during slough removal, debris removal, or both from the wound.

8. The anhydrous topical composition of claim 1, wherein the analgesic is hydrophobic.

9. The anhydrous topical composition of claim 8, wherein the analgesic is lidocaine.

10. The anhydrous topical composition of claim 1, wherein the omega fatty acid product is oil soluble.

11. The anhydrous topical composition of claim 1, wherein the nonoxidizing semi-occlusive film comprises cetyl esters.

12. The anhydrous topical composition of claim 11, wherein the omega fatty acid product comprises no odor.

13. The anhydrous topical composition of claim 1, wherein the omega fatty acid product further comprises about 20% to about 50% medium chain triglycerides (hereinafter "MCT") by weight.

14. The anhydrous topical composition of claim 13, wherein the omega fatty acid product comprises a weight ratio of the MCT to cod liver oil, hempseed oil, or both of 0.66.

* * * * *